US009644037B2

(12) United States Patent
Pfister et al.

(10) Patent No.: US 9,644,037 B2
(45) Date of Patent: May 9, 2017

(54) ANTIBODIES THAT SPECIFICALLY BIND ATAXIA TELANGIECTASIA-MUTATED AND RAD3-RELATED KINASE PHOSPHORYLATED AT POSITION 1989 AND THEIR USE

(71) Applicant: THE UNITED STATES OF AMERICA, AS REPRESENTED BY THE SECRETARY, DEPARTMENT OF HEALTH AND HUMAN SERVICES, Washington, DC (US)

(72) Inventors: Thomas D. Pfister, Toronto (CA); Allison M. Marrero, Gaithersburg, MD (US); Ralph E. Parchment, Hagerstown, MD (US); James H. Doroshow, Bethesda, MD (US); Robert J. Kinders, Frederick, MD (US)

(73) Assignee: THE UNITED STATES OF AMERICA, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/027,997

(22) PCT Filed: Oct. 8, 2014

(86) PCT No.: PCT/US2014/059759
§ 371 (c)(1),
(2) Date: Apr. 7, 2016

(87) PCT Pub. No.: WO2015/057461
PCT Pub. Date: Apr. 23, 2015

(65) Prior Publication Data
US 2016/0251447 A1    Sep. 1, 2016

Related U.S. Application Data

(60) Provisional application No. 61/893,070, filed on Oct. 18, 2013.

(51) Int. Cl.
| | | |
|---|---|---|
| C07K 16/00 | (2006.01) |
| G01N 33/53 | (2006.01) |
| C07K 16/40 | (2006.01) |
| C12Q 1/48 | (2006.01) |
| G01N 33/573 | (2006.01) |
| G01N 33/68 | (2006.01) |
| C12N 5/16 | (2006.01) |

(52) U.S. Cl.
CPC ............. *C07K 16/40* (2013.01); *C12N 5/16* (2013.01); *C12Q 1/485* (2013.01); *G01N 33/573* (2013.01); *G01N 33/6896* (2013.01); *C07K 2317/54* (2013.01); *C07K 2317/55* (2013.01); *C07K 2317/565* (2013.01); *C07K 2317/622* (2013.01); *C12N 2501/06* (2013.01); *C12Y 207/11001* (2013.01); *G01N 2333/91205* (2013.01); *G01N 2440/14* (2013.01); *G01N 2500/04* (2013.01); *G01N 2500/10* (2013.01); *G01N 2800/2814* (2013.01); *G01N 2800/52* (2013.01)

(58) Field of Classification Search
None
See application file for complete search history.

(56) References Cited

U.S. PATENT DOCUMENTS

| 6,348,311 B1 | 2/2002 | Kastan et al. |
| 2003/0077661 A1 | 4/2003 | Kastan et al. |
| 2007/0166764 A1 | 7/2007 | Livingstone et al. |
| 2009/0298093 A1 | 12/2009 | Polakiewicz et al. |

FOREIGN PATENT DOCUMENTS

| EP | 1 184 665 A1 | 3/2002 |
| WO | WO 98/55602 A1 | 12/1998 |
| WO | WO 2007/015840 A2 | 2/2007 |
| WO | WO 2007/127335 A2 | 11/2007 |
| WO | WO 2009/021137 A2 | 2/2009 |

OTHER PUBLICATIONS

International Search Report from parent PCT Application No. PCT/US2014/059759, 4 pages (mailed Apr. 9, 2015).
GeneTex®: ATR (phosphor Thr1989) antibody (Nov. 21, 2013).
Jossé et al., "ATR inhibitors VE-821 and VX-970 sensitize cancer cells to topoisomerase I inhibitors by disabling DNA replication initiation and fork elongation responses," *Cancer Research* 74(23):6968-6979 (Dec. 1, 2014).
Kozlov et al., "Involvement of novel autophosphorylation sites in ATM activation," *The EMBO Journal* 25:3504-3514 (2006).
Liu et al., "Nek1 kinase associates with ATR-ATRIP and primes ATR for efficient DNA damage signaling," *PNAS* 110(6):2175-2180 (Feb. 5, 2013).
Marrero et al., "Use of a DNA damage multiplex immunofluorescence assay to monitor pharmacodynamic markers following in vitro exposure to therapeutic," *Mol Cancer Ther* 12(11 Suppl):PR11, 1 page, (Abstract)(released online Oct. 9, 2013).

(Continued)

*Primary Examiner* — Mark Halvorson
(74) *Attorney, Agent, or Firm* — Klarquist Sparkman, LLP

(57) ABSTRACT

Monoclonal antibodies that specifically bind ataxia telangiectasia-mutated and RAD3-related kinase phosphorylated at position 1989 (pT1989 ATR), antigen binding fragments, conjugates thereof, and the use of these antibodies, antigen binding fragments and conjugates are disclosed herein. Also disclosed are nucleic acids encoding these antibodies, vectors including these antibodies, and isolated host cells transformed with these nucleic acids and vectors. Methods are also disclosed for using these antibodies, such as to detect pT1989 ATR, or to determine the dose of an agent of use to treat a subject. The antibodies are also of use for identifying ATR inhibitors.

40 Claims, 20 Drawing Sheets

(56) References Cited

OTHER PUBLICATIONS

Nam et al., "Thr-1989 Phosphorylation is a marker of active ataxia telangiectasia-mutated and Rad3-related (ATR) kinase," *The Journal of Biological Chemistry* 286(33): 28707-28714 (Aug. 19, 2011).
Wagner and Kaufmann, "Prospects for the use of ATR inhibitors to treat cancer," *Pharmaceuticals* 3:1311-1334 (2010).
Written Opinion from parent PCT Application No. PCT/US2014/059759, 5 pages (mailed Apr. 9, 2015).

```
   1 MGEHGLELAS MIPALRELGS ATPEEYNTVV QKPRQILCQF IDRILTDVNV VAVELVKKTD
  61 SQPTSVMLLD FIQHIMKSSP LMFVNVSGSH EAKGSCIEFS NWIITRLLRI AATPSCHLLH
 121 KKICEVICSL LFLFKSKSPA IFGVLTKELL QLFEDLVYLH RRNVMGHAVE WPVVMSRFLS
 181 QLDEHMGYLQ SAPLQLMSMQ NLEFIEVTLL MVLTRIIAIV FFRRQELLLW QIGCVLLEYG
 241 SPKIKSLAIS FLTELFQLGG LPAQPASTFF SSFLELLKHL VEMDTDQLKL YEEPLSKLIK
 301 TLFPFEAEAY RNIEPVYLNM LLEKLCVMFE DGVLMRLKSD LLKAALCHLL QYFLKFVPAG
 361 YESALQVRKV YVRNICKALL DVLGIEVDAE YLLGPLYAAL KMESMEIEE IQCQTQQENL
 421 SSNSDGISPK RRRLSSSLNP SKRAPKQTEE IKHVDMNQKS ILWSALKQKA ESLQISLEYS
 481 GLKNPVIEML EGIAVVLQLT ALCTVHCSHQ NMNCRTFKDC QHKSKKKPSV VITWMSLDFY
 541 TKVLKSCRSL LESVQKLDLE ATIDKVVKIY DALIYMQVNS SFEDHILEDL CGMLSLPWIY
 601 SHSDDGCLKL TTFAANLLTL SCRISDSYSP QAQSRCVFLL TLFPRRIFLE WRTAVYNWAL
 661 QSSHEVIRAS CVSGFFILLQ QQNSCNRVPK ILIDKVKDDS DIVKKEFASI LGQLVCTLHG
 721 MFYLTSSLTE PFSEHGHVDL FCRNLKATSQ HECSSSQLKA SVCKPFLFLL KKKIPSPVKL
 781 AFIDNLHHLC KHLDFREDET DVKAVLGTLL NLMEDPDKDV RVAFSGNIKH ILESLDSEDG
 841 FIKELFVLRM KEAYTHAQIS RNNELKDTLI LTTGDIGRAA KGDLVPFALL HLLHCLLSKS
 901 ASVSGAAYTE IRALVAAKSV KLQSFFSQYK KPICQFLVES LHSSQMTALP NTPCQNADVR
 961 KQDVAHQREM ALNTLSEIAN VFDFPDLNRF LTRTLQVLLP DLAAKASPAA SALIRTLGKQ
1021 LNVNRREILI NNFKYIFSHL VCSCSKDELE RALHYLKNET EIELGSLLRQ DFQGLHNELL
1081 LRIGEHYQQV FNGLSILASF ASSDDPYQGP RDIISPELMA DYLQPKLLGI LAFFNMQLLS
1141 SSVGIEDKKM ALNSLMSLMK LMGPKHVSSV RVKMMTTLRT GLRFKDDFPE LCCRAWDCFV
1201 RCLDHACLGS LLSHVIVALL PLIHIQPKET AAIFHYLIIE NRDAVQDFLH EIYFLPDHPE
1261 LKKIKAVLQE YRKETSESTD LQTTLQLSMK AIQHENVDVR IHALTSLKET LYKNQEKLIK
1321 YATDSETVEP IISQLVTVLL KGCQDANSQA RLLCGECLGE LGAIDPGRLD FSTTETQGKD
1381 FTFVTGVEDS SFAYGLLMEL TRAYLAYADN SRAQDSAAYA IQELLSIYDC REMETNGPGH
1441 QLWRRFPEHV REILEPHLNT RYKSSQKSTD WSGVKKPIYL SKLGSNFAEW SASWAGYLIT
1501 KVRHDLASKI FTCCSIMMKH DFKVTIYLLP HILVYVLLGC NQEDQQEVYA EIMAVLKHDD
1561 QHTINTQDIA SDLCQLSTQT VFSMLDHLTQ WARHKFQALK AEKCPHSKSN RNKVDSMVST
1621 VDYEDQSVT RFLDLIPQDT LAVASFRSKA YTRAVMHFES FITEKKQNIQ EHLGFLQKLY
1681 AAMHEPDGVA GVSAIRKAEP SLKEQILEHE SLGLLRDATA CYDRAIQLEP DQIHYHGVV
1741 KSMLGLGQLS TVITQVNGVH ANRSEWTDEL NTYRVEAAWK LSQWDLVENY LAADGKSTTW
1801 SVRLGQLLLS AKKRDITAFY DSLKLVRAEQ IVPLSAASFE RGSYQRGYEY IVRLHMLCEL
1861 EHSIKPLFQH SPGDSSQEDS LNWVARLEMT QNSYRAKEPI LALRRALLSL NKRPDYNEMV
1921 GECWLQSARV ARKAGHHQTA YNALLNAGES RLAELYVERA KWLWSKGDVH QALIVLQKGV
1981 ELCFPENETP PEGKNMLIHG RAMLLVGRFM EETANFESNA IMKKYKDVTA CLPEWEDGHF
2041 YLAKYYDKLM PMVTDNKMEK QGDLIRYIVL HFGRSLQYGN QFIYQSMPRM LTLWLDYGTK
2101 AYEWEKAGRS DRVQMRNDLG KINKVITEHT NYLAPYQFLT AFSQLISRIC HSHDEVFVVL
2161 MEIIAKVFLA YPQQAMWMMT AVSKSSYPMR VNRCKEILNK AIHMKKSLEK FVGDATRLTD
2221 KLLELCNKPV DGSSSTLSMS THFKMLKKLV EEATFSEILI PLQSVMIPTL PSILGTHANH
2281 ASHEPFPGHW AYIAGFDDMV EILASLQKPK KISLKGSDGK FYIMMCKPKD DLRKDCRLME
2341 FNSLINKCLR KDAESRRREL HIRTYAVIPL NDECGIIEWV NNTAGLRPIL TKLYKEKGVY
2401 MTGKELRQCM LPKSAALSEK LKVFREFLLP RHPPIFHEWF LRTFPDPTSW YSSRSAYCRS
2461 TAVMSMVGYI LGLGDRHGEN ILFDSLTGEC VHVDFNCLFN KGETFEVPEI VPFRLTHNMV
2521 NGMGPMGTEG LFRRACEVTM RLMRDQREPL MSVLKTFLHD PLVEWSKPVK GHSKAPLNET
2581 GEVVNEKAKT HVLDIEQRLQ GVIKTRNRVT GLPLSIEGHV HYLIQEATDE NLLCQMYLGW
2641 TPYM
```

FIG. 1 ap  (aa1983-1997): CFPENE-pT-PPEGKNML
bp  (aa1984-1997): FPENE-pT-PPEGKNML-C
anp (aa1983-1997): CFPENETPPEGKNML
bnp (aa1984-1997): FPENETPPEGKNML-C

Displaying 23 - 138 of 239 residues:

| | | Q | T | | V | L | M | T | Q | S | P | S | S | Y | S | A | A | V | G | G | T | V |
|---|---|---|---|---|---|---|---|---|---|---|---|---|---|---|---|---|---|---|---|---|---|---|
| Query protein sequence | | | | | | | | | | | | | | | | | | | | | | |
| Chothia numbering | L1 | L2 | L3 | L4 | L5 | L6 | L7 | L8 | L9 | L10 | L11 | L12 | L13 | L14 | L15 | L16 | L17 | L18 | L19 | L20 |
| Chothia+ numbering | L1 | L2 | L3 | L4 | L5 | L6 | L7 | L8 | L9 | L10 | L11 | L12 | L13 | L14 | L15 | L16 | L17 | L18 | L19 | L20 |
| Kabat numbering | L1 | L2 | L3 | L4 | L5 | L6 | L7 | L8 | L9 | L10 | L11 | L12 | L13 | L14 | L15 | L16 | L17 | L18 | L19 | L20 |

REGIONS CHOTHIA: LFR1
ABM: LFR1
KABAT: LFR1
CONTACT: LFR1

| T | C | Q | A | S | Q | L | V | S | Q | Y | K | N | A | W | L | A | S | T | N | Q | K | P | G |
|---|---|---|---|---|---|---|---|---|---|---|---|---|---|---|---|---|---|---|---|---|---|---|---|
| L21 | | | | L26 | L27 | L28 | L29 | L30 | L30A | L30B | L31 | L32 | L33 | L34 | L35 | L36 | L37 | L38 | L39 | L40 | L41 |
| L21 | | | | L26 | L27 | L28 | L29 | L30 | L30A | L30B | L31 | L32 | L33 | L34 | L35 | L36 | L37 | L38 | L39 | L40 | L41 |
| L21 | | | | L26 | L27 | L27A | L27B | L28 | L29 | L30 | L31 | L32 | L33 | L34 | L35 | L36 | L37 | L38 | L39 | L40 | L41 |

| L22 | L23 | L24 | L25 |
| L22 | L23 | L24 | L25 |
| L22 | L23 | L24 | L25 |

LFR2

| Q | R | P | K | L | L | I | Y | K | A | S | T | L | A | S | G | V | P | S | R | F | S | G | G |
|---|---|---|---|---|---|---|---|---|---|---|---|---|---|---|---|---|---|---|---|---|---|---|---|
| L42 | L43 | L44 | L45 | L46 | L47 | L48 | L49 | L50 | L51 | L52 | L53 | L54 | L55 | L56 | L57 | L58 | L59 | L60 | L61 | L62 | L63 | L64 |
| L42 | L43 | L44 | L45 | L46 | L47 | L48 | L49 | L50 | L51 | L52 | L53 | L54 | L55 | L56 | L57 | L58 | L59 | L60 | L61 | L62 | L63 | L64 |
| L42 | L43 | L44 | L45 | L46 | L47 | L48 | L49 | L50 | L51 | L52 | L53 | L54 | L55 | L56 | L57 | L58 | L59 | L60 | L61 | L62 | L63 | L64 |

FIG. 15A     FIG. 15B     FIG. 15C
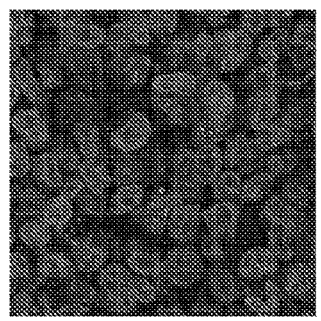
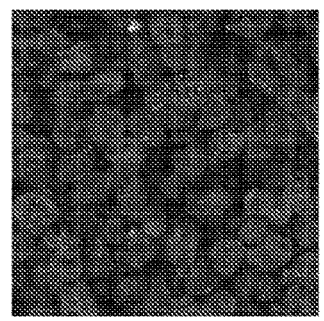
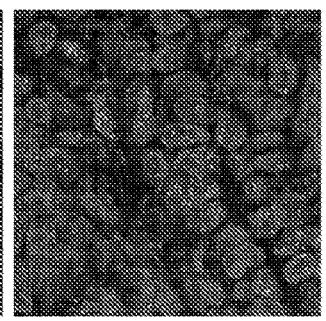
FIG. 15D
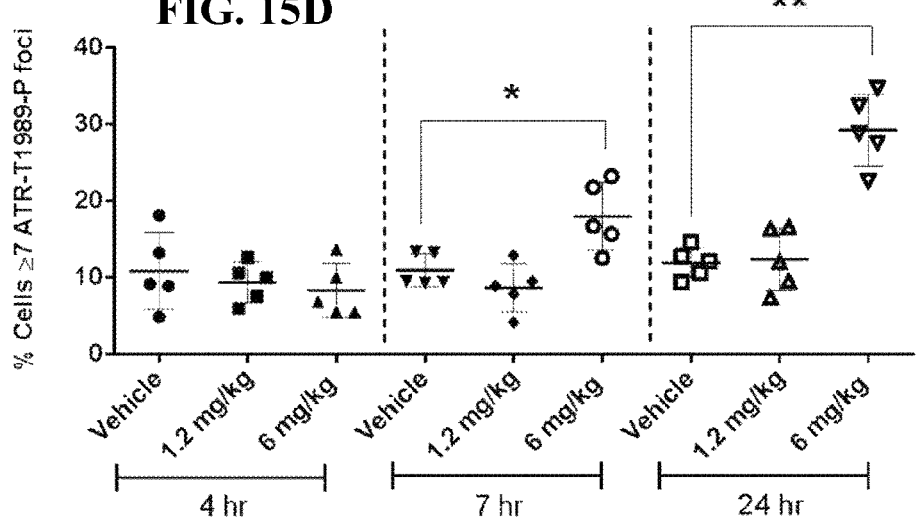

SEQUENCE LISTING

<160> NUMBER OF SEQ ID NOS: 9

<210> SEQ ID NO 1
<211> LENGTH: 2644
<212> TYPE: PRT
<213> ORGANISM: Homo sapiens

<400> SEQUENCE: 1

Met Gly Glu His Gly Leu Glu Leu Ala Ser Met Ile Pro Ala Leu Arg
1               5                   10                  15

-continued

```
Glu Leu Gly Ser Ala Thr Pro Glu Glu Tyr Asn Thr Val Val Gln Lys
             20                  25                  30

Pro Arg Gln Ile Leu Cys Gln Phe Ile Asp Arg Ile Leu Thr Asp Val
         35                  40                  45

Asn Val Val Ala Val Glu Leu Val Lys Lys Thr Asp Ser Gln Pro Thr
 50                  55                  60

Ser Val Met Leu Leu Asp Phe Ile Gln His Ile Met Lys Ser Ser Pro
65                  70                  75                  80

Leu Met Phe Val Asn Val Ser Gly Ser His Glu Ala Lys Gly Ser Cys
                 85                  90                  95

Ile Glu Phe Ser Asn Trp Ile Ile Thr Arg Leu Leu Arg Ile Ala Ala
             100                 105                 110

Thr Pro Ser Cys His Leu Leu His Lys Lys Ile Cys Glu Val Ile Cys
         115                 120                 125

Ser Leu Leu Phe Leu Phe Lys Ser Lys Ser Pro Ala Ile Phe Gly Val
130                 135                 140

Leu Thr Lys Glu Leu Leu Gln Leu Phe Glu Asp Leu Val Tyr Leu His
145                 150                 155                 160

Arg Arg Asn Val Met Gly His Ala Val Glu Trp Pro Val Val Met Ser
                 165                 170                 175

Arg Phe Leu Ser Gln Leu Asp Glu His Met Gly Tyr Leu Gln Ser Ala
             180                 185                 190

Pro Leu Gln Leu Met Ser Met Gln Asn Leu Glu Phe Ile Glu Val Thr
         195                 200                 205

Leu Leu Met Val Leu Thr Arg Ile Ile Ala Ile Val Phe Phe Arg Arg
210                 215                 220

Gln Glu Leu Leu Leu Trp Gln Ile Gly Cys Val Leu Leu Glu Tyr Gly
225                 230                 235                 240

Ser Pro Lys Ile Lys Ser Leu Ala Ile Ser Phe Leu Thr Glu Leu Phe
                 245                 250                 255

Gln Leu Gly Gly Leu Pro Ala Gln Pro Ala Ser Thr Phe Phe Ser Ser
             260                 265                 270

Phe Leu Glu Leu Leu Lys His Leu Val Glu Met Asp Thr Asp Gln Leu
         275                 280                 285

Lys Leu Tyr Glu Glu Pro Leu Ser Lys Leu Ile Lys Thr Leu Phe Pro
290                 295                 300

Phe Glu Ala Glu Ala Tyr Arg Asn Ile Glu Pro Val Tyr Leu Asn Met
305                 310                 315                 320

Leu Leu Glu Lys Leu Cys Val Met Phe Glu Asp Gly Val Leu Met Arg
                 325                 330                 335

Leu Lys Ser Asp Leu Leu Lys Ala Ala Leu Cys His Leu Leu Gln Tyr
             340                 345                 350

Phe Leu Lys Phe Val Pro Ala Gly Tyr Glu Ser Ala Leu Gln Val Arg
         355                 360                 365

Lys Val Tyr Val Arg Asn Ile Cys Lys Ala Leu Leu Asp Val Leu Gly
370                 375                 380

Ile Glu Val Asp Ala Glu Tyr Leu Leu Gly Pro Leu Tyr Ala Ala Leu
385                 390                 395                 400

Lys Met Glu Ser Met Glu Ile Ile Glu Ile Gln Cys Gln Thr Gln
                 405                 410                 415

Gln Glu Asn Leu Ser Ser Asn Ser Asp Gly Ile Ser Pro Lys Arg Arg
             420                 425                 430

Arg Leu Ser Ser Ser Leu Asn Pro Ser Lys Arg Ala Pro Lys Gln Thr
```

```
                435                 440                 445
Glu Glu Ile Lys His Val Asp Met Asn Gln Lys Ser Ile Leu Trp Ser
450                 455                 460
Ala Leu Lys Gln Lys Ala Glu Ser Leu Gln Ile Ser Leu Glu Tyr Ser
465                 470                 475                 480
Gly Leu Lys Asn Pro Val Ile Glu Met Leu Glu Gly Ile Ala Val Val
                485                 490                 495
Leu Gln Leu Thr Ala Leu Cys Thr Val His Cys Ser His Gln Asn Met
                500                 505                 510
Asn Cys Arg Thr Phe Lys Asp Cys Gln His Lys Ser Lys Lys Lys Pro
            515                 520                 525
Ser Val Val Ile Thr Trp Met Ser Leu Asp Phe Tyr Thr Lys Val Leu
530                 535                 540
Lys Ser Cys Arg Ser Leu Leu Glu Ser Val Gln Lys Leu Asp Leu Glu
545                 550                 555                 560
Ala Thr Ile Asp Lys Val Val Lys Ile Tyr Asp Ala Leu Ile Tyr Met
                565                 570                 575
Gln Val Asn Ser Ser Phe Glu Asp His Ile Leu Glu Asp Leu Cys Gly
            580                 585                 590
Met Leu Ser Leu Pro Trp Ile Tyr Ser His Ser Asp Asp Gly Cys Leu
            595                 600                 605
Lys Leu Thr Thr Phe Ala Ala Asn Leu Leu Thr Leu Ser Cys Arg Ile
            610                 615                 620
Ser Asp Ser Tyr Ser Pro Gln Ala Gln Ser Arg Cys Val Phe Leu Leu
625                 630                 635                 640
Thr Leu Phe Pro Arg Arg Ile Phe Leu Glu Trp Arg Thr Ala Val Tyr
                645                 650                 655
Asn Trp Ala Leu Gln Ser Ser His Glu Val Ile Arg Ala Ser Cys Val
                660                 665                 670
Ser Gly Phe Phe Ile Leu Leu Gln Gln Asn Ser Cys Asn Arg Val
            675                 680                 685
Pro Lys Ile Leu Ile Asp Lys Val Lys Asp Asp Ser Asp Ile Val Lys
            690                 695                 700
Lys Glu Phe Ala Ser Ile Leu Gly Gln Leu Val Cys Thr Leu His Gly
705                 710                 715                 720
Met Phe Tyr Leu Thr Ser Ser Leu Thr Glu Pro Phe Ser Glu His Gly
                725                 730                 735
His Val Asp Leu Phe Cys Arg Asn Leu Lys Ala Thr Ser Gln His Glu
                740                 745                 750
Cys Ser Ser Ser Gln Leu Lys Ala Ser Val Cys Lys Pro Phe Leu Phe
            755                 760                 765
Leu Leu Lys Lys Lys Ile Pro Ser Pro Val Lys Leu Ala Phe Ile Asp
            770                 775                 780
Asn Leu His His Leu Cys Lys His Leu Asp Phe Arg Glu Asp Glu Thr
785                 790                 795                 800
Asp Val Lys Ala Val Leu Gly Thr Leu Leu Asn Leu Met Glu Asp Pro
                805                 810                 815
Asp Lys Asp Val Arg Val Ala Phe Ser Gly Asn Ile Lys His Ile Leu
            820                 825                 830
Glu Ser Leu Asp Ser Glu Asp Gly Phe Ile Lys Glu Leu Phe Val Leu
            835                 840                 845
Arg Met Lys Glu Ala Tyr Thr His Ala Gln Ile Ser Arg Asn Asn Glu
            850                 855                 860
```

```
Leu Lys Asp Thr Leu Ile Leu Thr Thr Gly Asp Ile Gly Arg Ala Ala
865                 870                 875                 880

Lys Gly Asp Leu Val Pro Phe Ala Leu Leu His Leu Leu His Cys Leu
            885                 890                 895

Leu Ser Lys Ser Ala Ser Val Ser Gly Ala Ala Tyr Thr Glu Ile Arg
        900                 905                 910

Ala Leu Val Ala Ala Lys Ser Val Lys Leu Gln Ser Phe Phe Ser Gln
            915                 920                 925

Tyr Lys Lys Pro Ile Cys Gln Phe Leu Val Glu Ser Leu His Ser Ser
        930                 935                 940

Gln Met Thr Ala Leu Pro Asn Thr Pro Cys Gln Asn Ala Asp Val Arg
945                 950                 955                 960

Lys Gln Asp Val Ala His Gln Arg Glu Met Ala Leu Asn Thr Leu Ser
            965                 970                 975

Glu Ile Ala Asn Val Phe Asp Phe Pro Asp Leu Asn Arg Phe Leu Thr
            980                 985                 990

Arg Thr Leu Gln Val Leu Leu Pro  Asp Leu Ala Ala Lys  Ala Ser Pro
            995                 1000                1005

Ala Ala  Ser Ala Leu Ile Arg  Thr Leu Gly Lys Gln  Leu Asn Val
1010                1015                1020

Asn Arg  Arg Glu Ile Leu Ile  Asn Asn Phe Lys Tyr  Ile Phe Ser
1025                1030                1035

His Leu  Val Cys Ser Cys Ser  Lys Asp Glu Leu Glu  Arg Ala Leu
1040                1045                1050

His Tyr  Leu Lys Asn Glu Thr  Glu Ile Glu Leu Gly  Ser Leu Leu
1055                1060                1065

Arg Gln  Asp Phe Gln Gly Leu  His Asn Glu Leu Leu  Leu Arg Ile
1070                1075                1080

Gly Glu  His Tyr Gln Gln Val  Phe Asn Gly Leu Ser  Ile Leu Ala
1085                1090                1095

Ser Phe  Ala Ser Ser Asp Asp  Pro Tyr Gln Gly Pro  Arg Asp Ile
1100                1105                1110

Ile Ser  Pro Glu Leu Met Ala  Asp Tyr Leu Gln Pro  Lys Leu Leu
1115                1120                1125

Gly Ile  Leu Ala Phe Phe Asn  Met Gln Leu Leu Ser  Ser Ser Val
1130                1135                1140

Gly Ile  Glu Asp Lys Lys Met  Ala Leu Asn Ser Leu  Met Ser Leu
1145                1150                1155

Met Lys  Leu Met Gly Pro Lys  His Val Ser Ser Val  Arg Val Lys
1160                1165                1170

Met Met  Thr Thr Leu Arg Thr  Gly Leu Arg Phe Lys  Asp Asp Phe
1175                1180                1185

Pro Glu  Leu Cys Cys Arg Ala  Trp Asp Cys Phe Val  Arg Cys Leu
1190                1195                1200

Asp His  Ala Cys Leu Gly Ser  Leu Leu Ser His Val  Ile Val Ala
1205                1210                1215

Leu Leu  Pro Leu Ile His Ile  Gln Pro Lys Glu Thr  Ala Ala Ile
1220                1225                1230

Phe His  Tyr Leu Ile Ile Glu  Asn Arg Asp Ala Val  Gln Asp Phe
1235                1240                1245

Leu His  Glu Ile Tyr Phe Leu  Pro Asp His Pro Glu  Leu Lys Lys
1250                1255                1260
```

-continued

```
Ile Lys Ala Val Leu Gln Glu Tyr Arg Lys Glu Thr Ser Glu Ser
    1265                1270                1275

Thr Asp Leu Gln Thr Thr Leu Gln Leu Ser Met Lys Ala Ile Gln
    1280                1285                1290

His Glu Asn Val Asp Val Arg Ile His Ala Leu Thr Ser Leu Lys
    1295                1300                1305

Glu Thr Leu Tyr Lys Asn Gln Glu Lys Leu Ile Lys Tyr Ala Thr
    1310                1315                1320

Asp Ser Glu Thr Val Glu Pro Ile Ile Ser Gln Leu Val Thr Val
    1325                1330                1335

Leu Leu Lys Gly Cys Gln Asp Ala Asn Ser Gln Ala Arg Leu Leu
    1340                1345                1350

Cys Gly Glu Cys Leu Gly Glu Leu Gly Ala Ile Asp Pro Gly Arg
    1355                1360                1365

Leu Asp Phe Ser Thr Thr Glu Thr Gln Gly Lys Asp Phe Thr Phe
    1370                1375                1380

Val Thr Gly Val Glu Asp Ser Ser Phe Ala Tyr Gly Leu Leu Met
    1385                1390                1395

Glu Leu Thr Arg Ala Tyr Leu Ala Tyr Ala Asp Asn Ser Arg Ala
    1400                1405                1410

Gln Asp Ser Ala Ala Tyr Ala Ile Gln Glu Leu Leu Ser Ile Tyr
    1415                1420                1425

Asp Cys Arg Glu Met Glu Thr Asn Gly Pro Gly His Gln Leu Trp
    1430                1435                1440

Arg Arg Phe Pro Glu His Val Arg Glu Ile Leu Glu Pro His Leu
    1445                1450                1455

Asn Thr Arg Tyr Lys Ser Ser Gln Lys Ser Thr Asp Trp Ser Gly
    1460                1465                1470

Val Lys Lys Pro Ile Tyr Leu Ser Lys Leu Gly Ser Asn Phe Ala
    1475                1480                1485

Glu Trp Ser Ala Ser Trp Ala Gly Tyr Leu Ile Thr Lys Val Arg
    1490                1495                1500

His Asp Leu Ala Ser Lys Ile Phe Thr Cys Cys Ser Ile Met Met
    1505                1510                1515

Lys His Asp Phe Lys Val Thr Ile Tyr Leu Leu Pro His Ile Leu
    1520                1525                1530

Val Tyr Val Leu Leu Gly Cys Asn Gln Glu Asp Gln Gln Glu Val
    1535                1540                1545

Tyr Ala Glu Ile Met Ala Val Leu Lys His Asp Asp Gln His Thr
    1550                1555                1560

Ile Asn Thr Gln Asp Ile Ala Ser Asp Leu Cys Gln Leu Ser Thr
    1565                1570                1575

Gln Thr Val Phe Ser Met Leu Asp His Leu Thr Gln Trp Ala Arg
    1580                1585                1590

His Lys Phe Gln Ala Leu Lys Ala Glu Lys Cys Pro His Ser Lys
    1595                1600                1605

Ser Asn Arg Asn Lys Val Asp Ser Met Val Ser Thr Val Asp Tyr
    1610                1615                1620

Glu Asp Tyr Gln Ser Val Thr Arg Phe Leu Asp Leu Ile Pro Gln
    1625                1630                1635

Asp Thr Leu Ala Val Ala Ser Phe Arg Ser Lys Ala Tyr Thr Arg
    1640                1645                1650

Ala Val Met His Phe Glu Ser Phe Ile Thr Glu Lys Lys Gln Asn
```

-continued

```
            1655                1660                1665
Ile Gln Glu His Leu Gly Phe Leu Gln Lys Leu Tyr Ala Ala Met
    1670                1675                1680
His Glu Pro Asp Gly Val Ala Gly Val Ser Ala Ile Arg Lys Ala
    1685                1690                1695
Glu Pro Ser Leu Lys Glu Gln Ile Leu Glu His Glu Ser Leu Gly
    1700                1705                1710
Leu Leu Arg Asp Ala Thr Ala Cys Tyr Asp Arg Ala Ile Gln Leu
    1715                1720                1725
Glu Pro Asp Gln Ile Ile His Tyr His Gly Val Val Lys Ser Met
    1730                1735                1740
Leu Gly Leu Gly Gln Leu Ser Thr Val Ile Thr Gln Val Asn Gly
    1745                1750                1755
Val His Ala Asn Arg Ser Glu Trp Thr Asp Glu Leu Asn Thr Tyr
    1760                1765                1770
Arg Val Glu Ala Ala Trp Lys Leu Ser Gln Trp Asp Leu Val Glu
    1775                1780                1785
Asn Tyr Leu Ala Ala Asp Gly Lys Ser Thr Thr Trp Ser Val Arg
    1790                1795                1800
Leu Gly Gln Leu Leu Leu Ser Ala Lys Lys Arg Asp Ile Thr Ala
    1805                1810                1815
Phe Tyr Asp Ser Leu Lys Leu Val Arg Ala Glu Gln Ile Val Pro
    1820                1825                1830
Leu Ser Ala Ala Ser Phe Glu Arg Gly Ser Tyr Gln Arg Gly Tyr
    1835                1840                1845
Glu Tyr Ile Val Arg Leu His Met Leu Cys Glu Leu Glu His Ser
    1850                1855                1860
Ile Lys Pro Leu Phe Gln His Ser Pro Gly Asp Ser Ser Gln Glu
    1865                1870                1875
Asp Ser Leu Asn Trp Val Ala Arg Leu Glu Met Thr Gln Asn Ser
    1880                1885                1890
Tyr Arg Ala Lys Glu Pro Ile Leu Ala Leu Arg Arg Ala Leu Leu
    1895                1900                1905
Ser Leu Asn Lys Arg Pro Asp Tyr Asn Glu Met Val Gly Glu Cys
    1910                1915                1920
Trp Leu Gln Ser Ala Arg Val Ala Arg Lys Ala Gly His His Gln
    1925                1930                1935
Thr Ala Tyr Asn Ala Leu Leu Asn Ala Gly Glu Ser Arg Leu Ala
    1940                1945                1950
Glu Leu Tyr Val Glu Arg Ala Lys Trp Leu Trp Ser Lys Gly Asp
    1955                1960                1965
Val His Gln Ala Leu Ile Val Leu Gln Lys Gly Val Glu Leu Cys
    1970                1975                1980
Phe Pro Glu Asn Glu Thr Pro Pro Glu Gly Lys Asn Met Leu Ile
    1985                1990                1995
His Gly Arg Ala Met Leu Leu Val Gly Arg Phe Met Glu Glu Thr
    2000                2005                2010
Ala Asn Phe Glu Ser Asn Ala Ile Met Lys Lys Tyr Lys Asp Val
    2015                2020                2025
Thr Ala Cys Leu Pro Glu Trp Glu Asp Gly His Phe Tyr Leu Ala
    2030                2035                2040
Lys Tyr Tyr Asp Lys Leu Met Pro Met Val Thr Asp Asn Lys Met
    2045                2050                2055
```

-continued

```
Glu Lys Gln Gly Asp Leu Ile Arg Tyr Ile Val Leu His Phe Gly
    2060                2065                2070

Arg Ser Leu Gln Tyr Gly Asn Gln Phe Ile Tyr Gln Ser Met Pro
    2075                2080                2085

Arg Met Leu Thr Leu Trp Leu Asp Tyr Gly Thr Lys Ala Tyr Glu
    2090                2095                2100

Trp Glu Lys Ala Gly Arg Ser Asp Arg Val Gln Met Arg Asn Asp
    2105                2110                2115

Leu Gly Lys Ile Asn Lys Val Ile Thr Glu His Thr Asn Tyr Leu
    2120                2125                2130

Ala Pro Tyr Gln Phe Leu Thr Ala Phe Ser Gln Leu Ile Ser Arg
    2135                2140                2145

Ile Cys His Ser His Asp Glu Val Phe Val Leu Met Glu Ile
    2150                2155                2160

Ile Ala Lys Val Phe Leu Ala Tyr Pro Gln Gln Ala Met Trp Met
    2165                2170                2175

Met Thr Ala Val Ser Lys Ser Ser Tyr Pro Met Arg Val Asn Arg
    2180                2185                2190

Cys Lys Glu Ile Leu Asn Lys Ala Ile His Met Lys Lys Ser Leu
    2195                2200                2205

Glu Lys Phe Val Gly Asp Ala Thr Arg Leu Thr Asp Lys Leu Leu
    2210                2215                2220

Glu Leu Cys Asn Lys Pro Val Asp Gly Ser Ser Thr Leu Ser
    2225                2230                2235

Met Ser Thr His Phe Lys Met Leu Lys Lys Leu Val Glu Glu Ala
    2240                2245                2250

Thr Phe Ser Glu Ile Leu Ile Pro Leu Gln Ser Val Met Ile Pro
    2255                2260                2265

Thr Leu Pro Ser Ile Leu Gly Thr His Ala Asn His Ala Ser His
    2270                2275                2280

Glu Pro Phe Pro Gly His Trp Ala Tyr Ile Ala Gly Phe Asp Asp
    2285                2290                2295

Met Val Glu Ile Leu Ala Ser Leu Gln Lys Pro Lys Lys Ile Ser
    2300                2305                2310

Leu Lys Gly Ser Asp Gly Lys Phe Tyr Ile Met Met Cys Lys Pro
    2315                2320                2325

Lys Asp Asp Leu Arg Lys Asp Cys Arg Leu Met Glu Phe Asn Ser
    2330                2335                2340

Leu Ile Asn Lys Cys Leu Arg Lys Asp Ala Glu Ser Arg Arg Arg
    2345                2350                2355

Glu Leu His Ile Arg Thr Tyr Ala Val Ile Pro Leu Asn Asp Glu
    2360                2365                2370

Cys Gly Ile Ile Glu Trp Val Asn Asn Thr Ala Gly Leu Arg Pro
    2375                2380                2385

Ile Leu Thr Lys Leu Tyr Lys Glu Lys Gly Val Tyr Met Thr Gly
    2390                2395                2400

Lys Glu Leu Arg Gln Cys Met Leu Pro Lys Ser Ala Ala Leu Ser
    2405                2410                2415

Glu Lys Leu Lys Val Phe Arg Glu Phe Leu Leu Pro Arg His Pro
    2420                2425                2430

Pro Ile Phe His Glu Trp Phe Leu Arg Thr Phe Pro Asp Pro Thr
    2435                2440                2445
```

```
Ser Trp Tyr Ser Ser Arg Ser Ala Tyr Cys Arg Ser Thr Ala Val
    2450                2455                2460

Met Ser Met Val Gly Tyr Ile Leu Gly Leu Gly Asp Arg His Gly
    2465                2470                2475

Glu Asn Ile Leu Phe Asp Ser Leu Thr Gly Glu Cys Val His Val
    2480                2485                2490

Asp Phe Asn Cys Leu Phe Asn Lys Gly Glu Thr Phe Glu Val Pro
    2495                2500                2505

Glu Ile Val Pro Phe Arg Leu Thr His Asn Met Val Asn Gly Met
    2510                2515                2520

Gly Pro Met Gly Thr Glu Gly Leu Phe Arg Arg Ala Cys Glu Val
    2525                2530                2535

Thr Met Arg Leu Met Arg Asp Gln Arg Glu Pro Leu Met Ser Val
    2540                2545                2550

Leu Lys Thr Phe Leu His Asp Pro Leu Val Glu Trp Ser Lys Pro
    2555                2560                2565

Val Lys Gly His Ser Lys Ala Pro Leu Asn Glu Thr Gly Glu Val
    2570                2575                2580

Val Asn Glu Lys Ala Lys Thr His Val Leu Asp Ile Glu Gln Arg
    2585                2590                2595

Leu Gln Gly Val Ile Lys Thr Arg Asn Arg Val Thr Gly Leu Pro
    2600                2605                2610

Leu Ser Ile Glu Gly His Val His Tyr Leu Ile Gln Glu Ala Thr
    2615                2620                2625

Asp Glu Asn Leu Leu Cys Gln Met Tyr Leu Gly Trp Thr Pro Tyr
    2630                2635                2640

Met
```

<210> SEQ ID NO 2
<211> LENGTH: 15
<212> TYPE: PRT
<213> ORGANISM: Homo sapiens

<400> SEQUENCE: 2

```
Cys Phe Pro Glu Asn Glu Thr Pro Pro Glu Gly Lys Asn Met Leu
1               5                   10                  15
```

<210> SEQ ID NO 3
<211> LENGTH: 15
<212> TYPE: PRT
<213> ORGANISM: Homo sapiens

<400> SEQUENCE: 3

```
Phe Pro Glu Asn Glu Thr Pro Pro Glu Gly Lys Asn Met Leu Cys
1               5                   10                  15
```

<210> SEQ ID NO 4
<211> LENGTH: 15
<212> TYPE: PRT
<213> ORGANISM: Homo sapiens

<400> SEQUENCE: 4

```
Cys Phe Pro Glu Asn Glu Thr Pro Pro Glu Gly Lys Asn Met Leu
1               5                   10                  15
```

<210> SEQ ID NO 5
<211> LENGTH: 15
<212> TYPE: PRT
<213> ORGANISM: Homo sapiens

<400> SEQUENCE: 5

```
Phe Pro Glu Asn Glu Thr Pro Pro Glu Gly Lys Asn Met Leu Cys
1               5                   10                  15
```

<210> SEQ ID NO 6
<211> LENGTH: 455
<212> TYPE: PRT
<213> ORGANISM: Oryctolagus cuniculus

<400> SEQUENCE: 6

```
Glu Thr Gly Leu Arg Trp Leu Leu Val Ala Val Leu Lys Gly Val
1               5                   10                  15

Gln Cys Gln Ser Val Glu Ser Gly Gly Arg Leu Val Ala Pro Gly
                20                  25                  30

Thr Pro Leu Thr Leu Thr Cys Thr Val Ser Gly Ile Asp Leu Met Tyr
            35                  40                  45

Asn Ala Met Asn Trp Val Arg Gln Ala Pro Gly Lys Gly Leu Glu Phe
50                  55                  60

Ile Gly Met Ile Gly Ser Gly Gly Asn Thr Val Tyr Ala Ser Trp Ala
65                  70                  75                  80

Lys Gly Arg Phe Thr Ile Ser Lys Thr Ser Thr Val Gly Leu Lys
                85                  90                  95

Met Thr Ser Leu Thr Gln Glu Asp Thr Ala Thr Tyr Phe Cys Ala Arg
            100                 105                 110

Glu Gly Ser Gly Gly Ser Met Asp Phe Trp Gly Pro Gly Thr Leu Val
            115                 120                 125

Thr Val Ser Ser Gly Gln Pro Lys Ala Pro Ser Val Phe Pro Leu Ala
130                 135                 140

Pro Cys Cys Gly Asp Thr Pro Ser Ser Thr Val Thr Leu Gly Cys Leu
145                 150                 155                 160

Val Lys Gly Tyr Leu Pro Glu Pro Val Thr Val Thr Trp Asn Ser Gly
                165                 170                 175

Thr Leu Thr Asn Gly Val Arg Thr Phe Pro Ser Val Arg Gln Ser Ser
            180                 185                 190

Gly Leu Tyr Ser Leu Ser Ser Val Val Ser Val Thr Ser Ser Ser Gln
            195                 200                 205

Pro Val Thr Cys Asn Val Ala His Pro Ala Thr Asn Thr Lys Val Asp
        210                 215                 220

Lys Thr Val Ala Pro Ser Thr Cys Ser Lys Pro Thr Cys Pro Pro Pro
225                 230                 235                 240

Glu Leu Leu Gly Gly Pro Ser Val Phe Ile Phe Pro Pro Lys Pro Lys
                245                 250                 255

Asp Thr Leu Met Ile Ser Arg Thr Pro Glu Val Thr Cys Val Val
            260                 265                 270

Asp Val Ser Gln Asp Asp Pro Glu Val Gln Phe Thr Trp Tyr Ile Asn
            275                 280                 285

Asn Glu Gln Val Arg Thr Ala Arg Pro Pro Leu Arg Glu Gln Gln Phe
290                 295                 300

Asn Ser Thr Ile Arg Val Val Ser Thr Leu Pro Ile Ala His Gln Asp
305                 310                 315                 320

Trp Leu Arg Gly Lys Glu Phe Lys Cys Lys Val His Asn Lys Ala Leu
                325                 330                 335

Pro Ala Pro Ile Glu Lys Thr Ile Ser Lys Ala Arg Gly Gln Pro Leu
            340                 345                 350
```

```
Glu Pro Lys Val Tyr Thr Met Gly Pro Pro Arg Glu Leu Ser Ser
            355                 360                 365

Arg Ser Val Ser Leu Thr Cys Met Ile Asn Gly Phe Tyr Pro Ser Asp
    370                 375                 380

Ile Ser Val Glu Trp Glu Lys Asn Gly Lys Ala Glu Asp Asn Tyr Lys
385                 390                 395                 400

Thr Thr Pro Ala Val Leu Asp Ser Asp Gly Ser Tyr Phe Leu Tyr Ser
                405                 410                 415

Lys Leu Ser Val Pro Thr Ser Glu Trp Gln Arg Gly Asp Val Phe Thr
            420                 425                 430

Cys Ser Val Met His Glu Ala Leu His Asn His Tyr Thr Gln Lys Ser
            435                 440                 445

Ile Ser Arg Ser Pro Gly Lys
            450                 455

<210> SEQ ID NO 7
<211> LENGTH: 238
<212> TYPE: PRT
<213> ORGANISM: Oryctolagus cuniculus

<400> SEQUENCE: 7

Asp Thr Arg Ala Pro Thr Gln Leu Leu Gly Leu Leu Leu Leu Trp Leu
1               5                   10                  15

Pro Gly Ala Thr Phe Ala Leu Val Met Thr Gln Ser Pro Ser Ser Val
                20                  25                  30

Ser Ala Ala Val Gly Gly Thr Val Thr Ile Thr Cys Gln Ala Ser Gln
            35                  40                  45

Ser Leu Tyr Asn Asn Asn Tyr Leu Ala Trp Phe Gln Gln Lys Pro Gly
        50                  55                  60

Gln Arg Pro Lys Leu Leu Ile Tyr Lys Ala Ser Thr Leu Ala Ser Gly
65                  70                  75                  80

Val Pro Ser Arg Phe Lys Gly Ser Gly Ser Gly Thr Gln Phe Thr Leu
                85                  90                  95

Thr Ile Ser Asp Leu Glu Cys Glu Asp Ala Ala Thr Tyr Tyr Cys Leu
            100                 105                 110

Gly Glu Tyr Lys Asp Asn Val Asp Asp Gly Asn Ala Phe Gly Gly Gly
        115                 120                 125

Thr Glu Val Val Val Glu Gly Asp Pro Val Ala Pro Thr Val Leu Ile
130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
210                 215                 220

Gly Thr Thr Ser Val Val Gln Ser Phe Asn Arg Gly Asp Cys
225                 230                 235

<210> SEQ ID NO 8
<211> LENGTH: 1371
<212> TYPE: DNA
```

<213> ORGANISM: Oryctolagus cuniculus

<400> SEQUENCE: 8

```
atggagactg ggctgcgctg gcttctcctg gtcgctgtgc tcaaaggtgt ccagtgtcag    60
tcggtggagg agtccggggg tcgcctggtc gcccctggga cacccctgac actcacctgt   120
accgtctctg gaatcgacct catgtacaat gcaatgaact gggtccgcca ggctccaggg   180
aagggcctgg aattcatcgg aatgattggt agtggtggta atacagtcta tgcgagctgg   240
gcgaaaggcc gattcaccat ctccaaaacc tcgaccacgg tgggtctgaa gatgaccagt   300
ctgacacagg aggacacggc cacctatttc tgtgccagag agggtagtgg tggcagtatg   360
gacttctggg gcccaggcac cctggtcacc gtctcctcag ggcaacctaa ggctccatca   420
gtcttcccac tggcccccctg ctgcggggac acacccagct ccacggtgac cctgggctgc   480
ctggtcaaag ggtacctccc ggagccagtg accgtgacct ggaactcggg caccctcacc   540
aatggggtac gcaccttccc gtccgtccgg cagtcctcag gcctctactc gctgagcagc   600
gtggtgagcg tgacctcaag cagccagccc gtcacctgca acgtggccca cccagccacc   660
aacaccaaag tggacaagac cgttgcgccc tcgacatgca gcaagcccac gtgcccaccc   720
cctgaactcc tggggggacc gtctgtcttc atcttccccc caaaacccaa ggacaccctc   780
atgatctcac gcacccccga ggtcacatgc gtggtggtgg acgtgagcca ggatgacccc   840
gaggtgcagt tcacatggta cataaacaac gagcaggtgc gcaccgcccg ccgccgccta   900
cgggagcagc agttcaacag cacgatccgc gtggtcagca ccctcccccat cgcgcaccag   960
gactggctga ggggcaagga gttcaagtgc aaagtccaca acaaggcact cccggccccc  1020
atcgagaaaa ccatctccaa agccagaggg cagcccctgg agccgaaggt ctacaccatg  1080
ggccctcccc gggaggagct gagcagcagg tcggtcagcc tgacctgcat gatcaacggc  1140
ttctacccctt ccgacatctc ggtggagtgg gagaagaacg ggaaggcaga ggacaactac  1200
aagaccacgc cggccgtgct ggacagcgac ggctcctact tcctctacag caagctctca  1260
gtgcccacga gtgagtggca gcggggcgac gtcttcacct gctccgtgat gcacgaggcc  1320
ttgcacaacc actacacgca gaagtccatc tcccgctctc cgggtaaatg a            1371
```

<210> SEQ ID NO 9
<211> LENGTH: 720
<212> TYPE: DNA
<213> ORGANISM: Oryctolagus cuniculus

<400> SEQUENCE: 9

```
atggacacga gggcccccac tcagctgctg ggctcctgc tgctctggct cccaggtgcc    60
acatttgccc tggtgatgac ccagtctcca tcctccgtgt ctgcagctgt gggaggcaca   120
gtcaccatca cttgccaggc cagtcagagt ctttataata acaactactt agcctggttt   180
cagcagaaac cagggcagcg tcccaagctc ctgatctaca aggcatccac tctggcaagt   240
ggggtcccat cgcgcttcaa aggcagtgga tctgggacac agttcactct caccatcagc   300
gacctggagt gtgaagatgc tgccacttac tactgcctag cgaatataa ggataatgta   360
gatgatggta atgctttcgg cggagggacc gaggtggtgg tcgaaggtga tccagttgca   420
cctactgtcc tcatcttccc accagctgct gatcaggtgg caactggaac agtcaccatc   480
gtgtgtgtgg cgaataaata ctttcccgat gtcaccgtca cctgggaggt ggatggcacc   540
acccaaacaa ctggcatcga gaacagtaaa acaccgcaga attctgcaga ttgtacctac   600
```

```
aacctcagca gcactctgac actgaccagc acacagtaca acagccacaa agagtacacc      660
tgcaaggtga cccagggcac gacctcagtc gtccagagct tcaatagggg tgactgttag      720
```

ANTIBODIES THAT SPECIFICALLY BIND ATAXIA TELANGIECTASIA-MUTATED AND RAD3-RELATED KINASE PHOSPHORYLATED AT POSITION 1989 AND THEIR USE

CROSS REFERENCE TO RELATED APPLICATIONS

This is a §371 U.S. national stage of International Application No. PCT/US2014/059759, filed Oct. 8, 2014, which was published in English under PCT Atricle 21(2), which claims the benefit of U.S. Provisional Application No. 61/893,070, filed Oct. 18, 2013, which is incorporated herein by reference.

FIELD OF THE DISCLOSURE

This is related to the field of kinases, particularly to antibodies that specifically bind ataxia telangiectasia-mutated and RAD3-related kinase phosphorylated at position 1989 (pT1989 ATR) and their use.

BACKGROUND

The DNA damage response coordinates cell cycle transitions, DNA replication, DNA repair, and apoptosis to guard against genomic instability. Three related kinases belonging to the PI3K-related protein kinase (PIKKs)⁻ family, ataxia telangiectasia-mutated (ATM), ATM and RAD3-related (ATR), and DNA-dependent protein kinase (DNA-PK), are involved in the DNA damage response. ATR is essential for viability in replicating human cells, and disruption of ATR in mice results in embryonic lethality (see, for example, Cortez et al., (2001) *Science* 294, 1713-1716). ATR regulates replication fork stability, restart of collapsed forks, and late-origin firing during S-phase. This kinase also activates the $G_2$ checkpoint to prevent entry into mitosis in the presence of damaged DNA (see, for example, Sancar et al., (2004) *Annu. Rev. Biochem.* 73, 39-85).

Hypomorphic mutations in ATR cause Seckel syndrome and ATR mutations have been associated with poor prognosis of tumors with microsatellite instability (O'Driscoll, (2003) *Nat. Genet.* 33, 497-501; Zighelboim et al., (2009) *J. Clin. Oncol.* 27, 3091-3096: Lewis et al., Genes Chromosomes Cancer 46, 1061-1068). A key function of ATR is activation of checkpoint kinase 1 (Chk1), leading to cell cycle arrest. Many anti-cancer therapeutics induce DNA damage and ATR is itself a drug target.

ATM, ATR and DNA-PK undergo autophosphorylation. Phosphorylation sites on ATM and DNA-PK are functionally significant and have been used as direct markers of activation (see, for example, Kozlov et al., (2006) *EMBO J.* 25, 3504-3514). Phosphorylation at the threonine at position 1989 (T1989) is important for ATR activation (Nam et al., (2011), *J. Biol. Chem.* 286: 28707-28714). There is a need for reagents that can be used to detect ATR phosphorylation at this position.

SUMMARY OF THE DISCLOSURE

Monoclonal antibodies that specifically bind ataxia telangiectasia-mutated and RAD3-related kinase phosphorylated at position 1989 (pT1989 ATR), antigen binding fragments, conjugates thereof, and the use of these antibodies, antigen binding fragments and conjugates are disclosed herein. In some embodiments, the isolated monoclonal antibody, or antigen binding fragment thereof, includes a heavy chain variable region and a light chain variable region, wherein the heavy chain variable region includes a heavy chain complementarity determining region (H-CDR)1, a H-CDR2, and a H-CDR3 of the heavy chain variable region set forth as SEQ ID NO: 6, and wherein the light chain variable domain includes a light chain complementarity determining region (L-CDR)1, a L-CDR2, and a L-CDR3 of the light chain variable region set forth as SEQ ID NO: 7. In additional embodiments, nucleic acids encoding are disclosed that encode these antibodies, as well as vectors expressing these nucleic acids, and isolated host cells transformed with these nucleic acids and vectors.

In further embodiments, methods are also disclosed for using these antibodies, such as to detect pT1989 ATR, or to determine if an agent is of use to treat a subject. The antibodies disclosed herein are also of use for identifying ATR inhibitors. The antibodies have enhanced affinity for pT1989 ATR.

The foregoing and other features and advantages of the invention will become more apparent from the following detailed description of a several embodiments which proceeds with reference to the accompanying figures.

BRIEF DESCRIPTION OF THE FIGURES

FIG. 1. Protein sequence (SEQ ID NO: 1) of human serine/threonine-protein kinase ATR (2644 amino acids, NP_001175.2).

FIG. 2. Peptide sequences, ap (SEQ ID NO: 2), by (SEQ ID NO: 3), anp (SEQ ID NO: 4) and bnp (SEQ ID NO: 5) used for immunization and/or screening.

FIG. 13A-13D shows the location of the CDRs, as identified using Kabat and Chothia. The CDR using two other identification systems (Enhanced Chothia (Chothia+) and Contact) are also shown. The Table presents the amino acid sequence of the heavy and light chains (SEQ ID NO: 6 and SEQ ID NO: 7), and provides the position numbers for each numbering schemes. In the bar graphs below the figure, the framework regions are represented with light grey bars (or no bar) and CDRs are represented by dark grey bars. The framework regions continue beyond the indicated bars, so that they abut each CDR and continue to the end of the sequence.

FIGS. 15A-15D show results from A2780 xenografts. Representative images of the pATR T1989 immunofluorescence assay in A2780 xenografts from mice treated for 24 hours with either (A) vehicle, (B) 1.2 mg/kg cisplatin or (C) 6.0 mg/kg cisplatin. (D) Quantitation of the percent of cells with ≥7 pATR T1989 foci per nucleus, results are mean±S.D. of an average of 10 representative fields per xenograft quadrant, 5 mice per group. Each point on the graph represents one xenograft.]

SEQUENCES

Figure 3A:
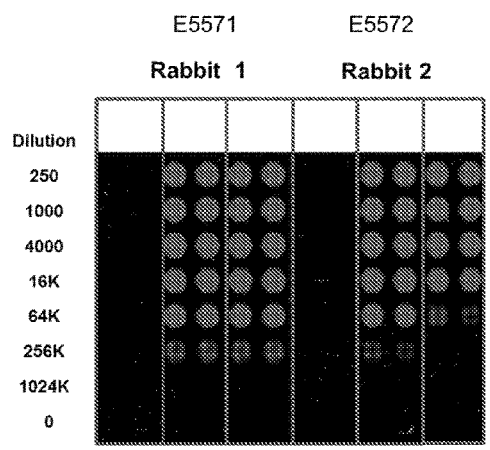
FIGS. 3A-3D. Rabbit bleed screening ELISA with phospho-peptides on 96 well plates. Fluorescence signal at 680 nm from Licor ODYSSEY® infrared scanner for (3A) ATR phospho-peptide A conjugated to bovine serum albumin (BSA), and (3B) ATR phospho-peptide B conjugated to bovine serum albumin (BSA). Dilution curve for (3C) ATR phospho-peptide A conjugated to bovine serum albumin (BSA) and (3D) ATR phospho-peptide B conjugated to bovine serum albumin (BSA).
Figure 3B:
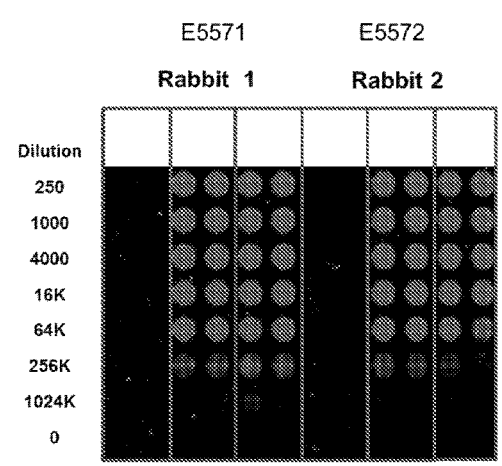
Figure 3C:
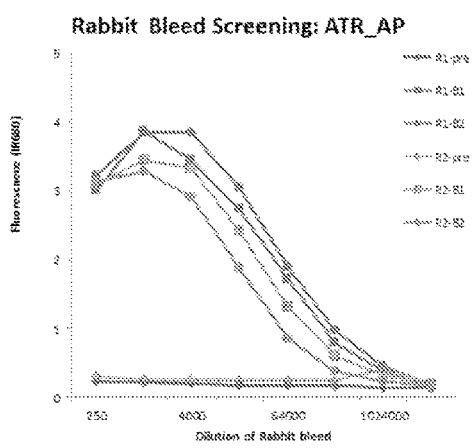
Figure 3D:
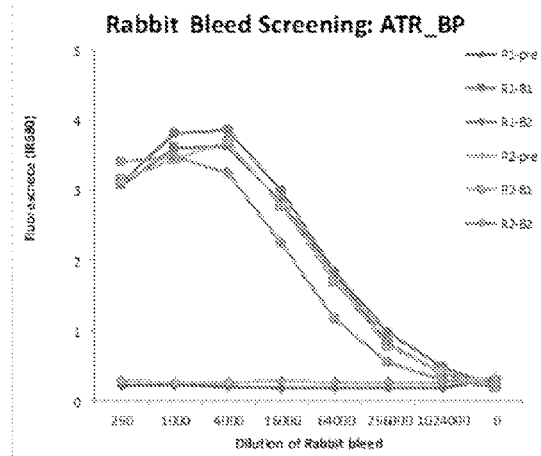
Figure 4A:
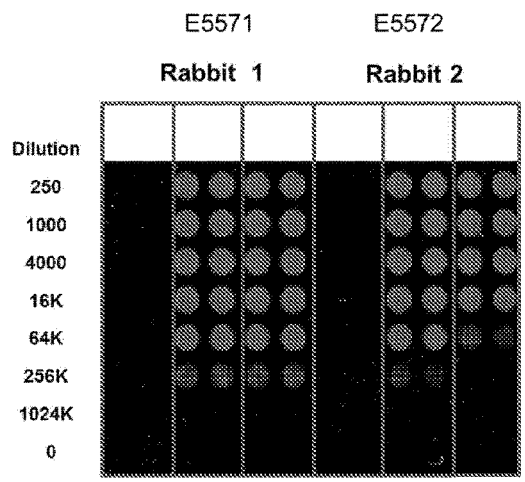
FIGS. 4A-4D. Rabbit bleed screen with phospho-peptides on 96 well plates. Fluorescence signal at 680 nm from Licor Odyssey infrared scanner for (4A) ATR phospho-peptide A conjugated to bovine serum albumin (BSA), and (4B) ATR phospho-peptide B conjugated to bovine serum albumin (BSA). Dilution curve for (4C) ATR phospho-peptide A conjugated to bovine serum albumin (BSA) and (4D) ATR phospho-peptide B conjugated to bovine serum albumin (BSA).
Figure 4B:
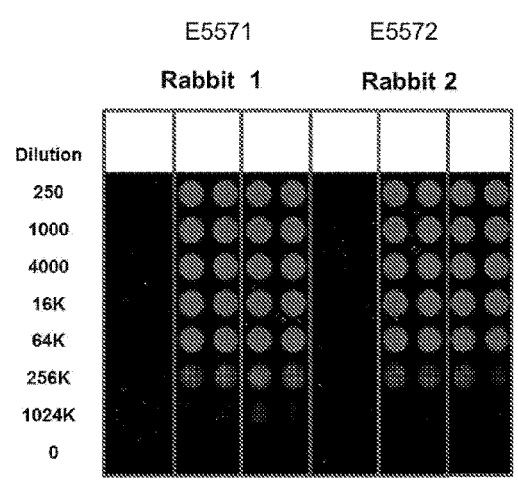
Figure 4C:
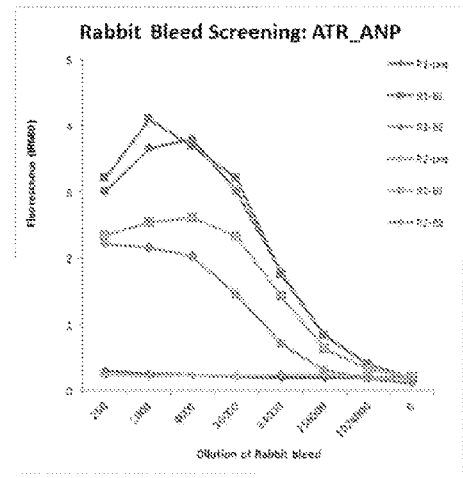
Figure 4D:
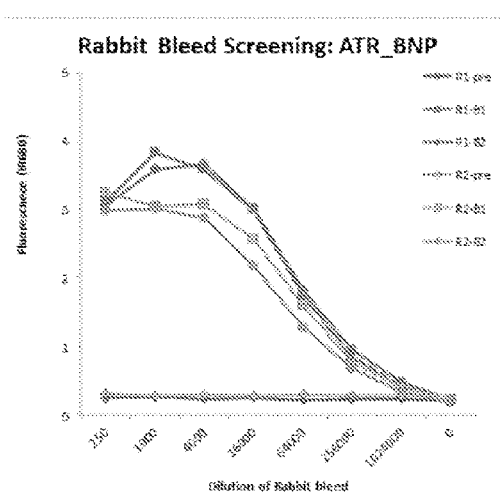

The nucleic and amino acid sequences listed are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [4239-91933-03 Sequence.txt, Apr. 5, 2016, 32.7 KB], which is incorporated by reference herein.

SEQ ID NO: 1 is the amino acid sequence of human ATR, see FIG. 1.

SEQ ID NOs: 2-5 are the amino acid sequences of human ATR peptides, see FIG. 2.

SEQ ID NO: 6 is the amino acid sequence of a heavy chain of an antibody that specifically binds pT1989 ATR.

SEQ ID NO: 7 is the amino acid sequence of a light chain of an antibody that specifically binds pT1989 ATR.

SEQ ID NO: 8 is the nucleic acid sequence of an exemplary nucleic acid molecule that encodes the heavy chain amino acid sequence set forth as SEQ ID NO: 6 SEQ ID NO: 9 is the nucleic acid sequence of an exemplary nucleic acid molecule that encodes the light chain amino acid sequence set forth as SEQ ID NO: 7.

DETAILED DESCRIPTION OF SEVERAL EMBODIMENTS

Monoclonal antibodies that specifically bind pT1989 ATR, antigen binding fragments of these antibodies, conjugates of these antibodies and antigen binding fragments, and the use of these antibodies, antigen binding fragments and conjugates are disclosed herein.

I. Summary of Terms

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, for example, "comprising an antibody" means "including an antibody" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

Administration: To provide or give to a subject an agent, for example, a chemotherapeutic agent or an antibody, by any effective route. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Agent: Any substance or any combination of substances that is useful for achieving an end or result; for example, a substance or combination of substances useful for decreasing or reducing tumor growth in a subject. Agents include effector molecules, detectable markers, antibodies, antigen binding fragments of antibodies, and chemical compounds such as, but not limited to, chemotherapeutic compounds.

Antibody: A polypeptide substantially encoded by an immunoglobulin gene or immunoglobulin genes, or antigen binding fragments thereof, which specifically binds and recognizes an analyte (antigen) such as pT1989 ATR or an antigenic fragment of pT1989 ATR. Immunoglobulin genes include the kappa, lambda, alpha, gamma, delta, epsilon and mu constant region genes, as well as the myriad immunoglobulin variable domain genes. The term "antibody," as used herein, also includes antigen binding fragments either produced by the modification of whole antibodies or those synthesized de novo using recombinant DNA methodologies.

Non-limiting examples of antibodies include, for example, intact immunoglobulins and variants and fragments thereof known in the art that retain specific binding affinity for the antigen. Antibodies also include genetically engineered forms such as chimeric antibodies (such as humanized murine antibodies) and heteroconjugate antibodies (such as bispecific antibodies). See also, *Pierce Catalog and Handbook,* 1994-1995 (Pierce Chemical Co., Rockford, Ill.); Kuby, J., *Immunology,* 3$^{rd}$ Ed., W.H. Freeman & Co., New York, 1997.

Examples of antigen binding fragments include: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable domain of the light chain and the variable domain of the heavy chain expressed as two chains; and (6) single chain antibody ("SCA"), a genetically engineered molecule containing the variable domain of the light chain, the variable domain of the heavy chain, linked by a suitable polypeptide linker as a genetically fused single chain molecule.

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science,* 242:423-426, 1988; Huston et al., *Proc. Natl. Acad. Sci.,* 85:5879-5883, 1988). In a dsFv the heavy and light chain variable chains have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.,* 90:6444-6448, 1993; Poljak et al., *Structure,* 2:1121-1123, 1994).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Typically, a naturally occurring antibody has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region (the regions are also known as "domains"). In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., *Nature,* 363:446-448, 1993; Sheriff et al., *Nat. Struct. Biol.,* 3:733-736, 1996). Light and heavy chain variable regions contain a "framework" region interrupted by three hypervariable regions, also called "complementarity-determining regions" or "CDRs" (see, e.g., Kabat et al., *Sequences of Proteins of Immunological Interest,* U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273, 927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the variable region of the heavy chain of the antibody in which it is found, whereas a $V_L$ CDR1 is the CDR1 from the variable region of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

References to "$V_H$" or "VH" refer to the variable domain of an immunoglobulin heavy chain, including that of an antigen binding fragment, such as Fv, scFv, dsFv or Fab. References to "$V_L$" or "VL" refer to the variable domain of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected, or a progeny thereof. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include chimeric, humanized and fully human monoclonal antibodies. In some examples monoclonal antibodies are isolated from a subject. The amino acid sequences of such isolated monoclonal antibodies can be determined. Monoclonal antibodies can have conservative amino acid substitutions which have substantially no effect on antigen binding or other immunoglobulin functions. (See, for example, Harlow & Lane, *Antibodies, A Laboratory Manual*, Cold Spring Harbor Publications, New York (1988).)

A "chimeric" antibody is an antibody including a framework region from one antibody and one or more CDRs from a heterologous antibody. The framework regions and the CDRs can be from antibodies from the same or different species.

A "humanized" antibody is an antibody including a human framework region and one or more CDRs from a non-human (such as a mouse, rat, or synthetic) immunoglobulin. The non-human antibody providing the CDRs is termed a "donor," and the human antibody providing the framework is termed an "acceptor." In one embodiment, all the CDRs are from the donor antibody in a humanized antibody. Constant regions need not be present, but if they are, they must be substantially identical to human antibody constant regions, such as at least about 85-90%, such as about 95% or more identical. Hence, all parts of a humanized antibody, except possibly the CDRs, are substantially identical to corresponding parts of natural human antibody sequences. A "humanized antibody" is an antibody including a humanized light chain and a humanized heavy chain. A humanized antibody binds to the same antigen as the donor antibody that provides the CDRs. The acceptor framework of a humanized immunoglobulin or antibody may have a limited number of substitutions by amino acids taken from the donor framework.

Humanized, chimeric or other monoclonal antibodies can have additional conservative amino acid substitutions, such as in the framework region, which have substantially no effect on antigen binding or other immunoglobulin functions. Humanized an chimeric immunoglobulins can be constructed by means of genetic engineering (for example, see U.S. Pat. No. 5,585,089).

Ataxia telangiectasia-mutated and Rad3-related (ATR) kinase: A member of the phosphoinositide 3-kinase related kinase (PIKK) family. ATR includes a kinase domain, a FAT domain and a FATC (FAT domain at the carboxy terminus) domain. The FAT domain is part of a long N-terminal region predicted to fold into alpha-helical HEAT repeats, each 37-47 amino acids long. ATR is a large kinase of 2644 amino acids in length, with a molecular weight of approximately 300 kD. ATR-interacting protein (ATRIP), the 85 kDa binding partner of ATR, binds to the N-terminus of ATR. ATR is an atypical kinase for checkpoint kinase 1 (Chk1), which has a role in cell cycle arrest, DNA repair, and apoptosis. ATR is essential for viability in replicating human cells, and can be activated by a variety of types of DNA damage. ATR is phosphorylated at the threonine at position 1989 (T1989) upon activation. An exemplary amino acid sequence for ATR is provided as GENBANK® Accession No. NP_001175.2, Sep. 29, 2013, incorporated by reference herein, and is shown in FIG. 1.

Binding affinity: Affinity of an antibody or antigen binding fragment thereof for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1 \times 10^{-8}$ M. In other embodiments, a high binding affinity is at least about $1.0 \times 10^{-9}$, at least about $5.0 \times 10^{-9}$, at least about $1.0 \times 10^{-10}$, at least about $5.0 \times 10^{-10}$, or at least about $1.0 \times 10^{-11}$.

Biological sample: A sample obtained from a subject. Biological samples include all clinical samples useful for detection of disease n subjects, including, but not limited to, cells, tissues, and bodily fluids, such as blood, derivatives and fractions of blood such as serum, cerebrospinal fluid; as well as biopsied or surgically removed tissue, for example tissues that are unfixed, frozen, or fixed in formalin or paraffin. In a particular example, a biological sample is obtained from a subject having or suspected of having a tumor; for example, a subject having or suspected of having breast, colorectal, lung, or skin cancer. In some examples, the subject has or is suspected of having a carcinoma.

Bispecific antibody: A recombinant molecule composed of two different antigen binding domains that consequently bind to two different antigenic epitopes. Bispecific antibodies include chemically or genetically linked molecules of two antigen-binding domains. The antigen binding domains can be linked using a linker. The antigen binding domains can be monoclonal antibodies, antigen-binding fragments (e.g., Fab, scFv), eAds, bispecific single chain antibodies or combinations thereof. A bispecific antibody can include one or more constant domains, but does not necessarily include a constant domain. An example of a bispecific antibody is a bispecific single chain antibody including a scFv that specifically binds to pT1989 ATR joined (via a peptide linker) to a scFv that specifically binds to an antigen other than pT1989 ATR.

Cell cycle: The series of events that takes place in a cell leading to its division and duplication (replication). The cell cycle can be divided into two brief periods: interphase-during which the cell grows, accumulating nutrients needed for mitosis and duplicating its DNA and t mitosis (M) phase, during which the cell splits itself into two distinct cells, often called "daughter cells." The cell cycle includes four distinct phases: $G_1$ phase (interphase or growth phase), S phase (DNA synthesis, chromosome replication), $G_2$ phase (growth phase) and M phase (mitosis, including karyokinesis and cytokines). In karyokinesis the cell's chromosomes are divided between the two daughter cells, and during cytokinesis the cell's cytoplasm divides in half forming distinct cells. Activation of each phase is dependent on the proper progression and completion of the previous one. Cells that have temporarily or reversibly stopped dividing are said to have entered a state of quiescence called $G_0$ phase. Cells in a population that are "synchronized" are at the same phase of the cell cycle, such as $G_1$, S, $G_2$ or M.

Conditions sufficient to form an immune complex: Conditions which allow an antibody or antigen binding fragment thereof to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane, supra, for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Conjugate: A complex of two molecules linked together, for example, linked together by a covalent bond. In one embodiment, an antibody is linked to an effector molecule; for example, an antibody that specifically binds to pT1989 ATR covalently linked to an effector molecule such as a detectable label. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative variants: "Conservative" amino acid substitutions are those substitutions that do not substantially decrease the binding affinity of an antibody for an antigen (for example, the binding affinity of an antibody for pT1989 ATR). For example, an antibody that specifically binds pT1989 ATR can include at most about 1, at most about 2, at most about 5, at most about 10, or at most about 15 conservative substitutions and specifically bind the pT1989 ATR polypeptide. The term conservative variation also includes the use of a substituted amino acid in place of an unsubstituted parent amino acid, provided that antibody retains binding affinity for pT1989 ATR. Non-conservative substitutions are those that reduce an activity or binding to pT1989 ATR.

Conservative amino acid substitution tables providing functionally similar amino acids are well known to one of ordinary skill in the art. The following six groups are examples of amino acids that are considered to be conservative substitutions for one another:
  1) Alanine (A), Serine (S), Threonine (T);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V); and
  6) Phenylalanine (F), Tyrosine (Y), Tryptophan (W).

Contacting: Placement in direct physical association, for example solid, liquid or gaseous forms. Contacting includes, for example, direct physical association of fully- and partially-solvated molecules.

Control: A reference standard. In some embodiments, the control is a negative control, such as tissue sample obtained from a patient that does not have cancer, or a tissue sample from a tissue that is non-cancerous. In other embodiments, the control is a positive control, such as a tissue sample obtained from a patient diagnosed with cancer, or a tissue sample from a cancerous tissue. In still other embodiments, the control is a historical control or standard reference value or range of values (such as a previously tested control sample, such as a group of cancer patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Decrease or Reduce: To reduce the quality, amount, or strength of something; for example phosphorylation at position 1989 of ATR. In one example, an agent reduces phosphorylation at position 1989 of ATR, for example as compared to phosphorylation in the absence of the agent. In a particular example, a therapy decreases the phosphorylation at position 1989 of ATR at least about 10%, at least about 20%, at least about 30%, at least about 40%, at least about 50%, at least about 60%, at least about 70%, at least about 80%, at least about 90%, or at least about 100%. Such decreases can be measured using the methods disclosed herein.

Degenerate variant: In the context of the present disclosure, a "degenerate variant" refers to a polynucleotide encoding a protein (for example, an antibody that specifically binds pT1989 ATR) that includes a sequence that is degenerate as a result of the genetic code. There are twenty natural amino acids, most of which are specified by more than one codon. Therefore, all degenerate nucleotide sequences are included as long as the amino acid sequence of the antibody that binds pT1989 ATR encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, Cold Spring Harbor, N.Y., 2012) and Ausubel et al. (In Current Protocols in Molecular Biology, John Wiley & Sons, New York, 1998).

Detecting: To identify the existence, presence, or fact of something. General methods of detecting are known to the skilled artisan and may be supplemented with the protocols and reagents disclosed herein. For example, included herein are methods of detecting a cell that expresses pT1989 ATR in a subject.

Effective amount: The amount of an agent (such as a pT1989 ATR specific antibody or a conjugate including a pT1989 ATR specific antibody) that alone, or together with one or more additional agents, induces the desired response, such as, for example formation of a detectable immune complex with pT1989 ATR.

Effector molecule: A molecule intended to have or produce a desired effect; for example, a desired effect on a cell to which the effector molecule is targeted. Effector molecules include such molecules as polypeptides, radioisotopes and small molecules. Non-limiting examples of effector molecules include detectable labels, toxins, chemotherapeutic agents and anti-angiogenic agents. The skilled artisan will understand that some effector molecules may have or produce more than one desired effect. In one example, an effector molecule is the portion of a chimeric molecule, for example a chimeric molecule that includes a disclosed antibody or fragment thereof, that is intended to have a desired effect on a cell to which the chimeric molecule is targeted.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope present on ATR phosphorylated at position 1989, but not to ATR that in not phosphorylated at position 1989.

Framework Region: Amino acid sequences interposed between CDRs in a heavy or light variable region of an antibody. Includes variable light and variable heavy framework regions. The framework regions serve to hold the CDRs in an appropriate orientation.

IgA: A polypeptide belonging to the class of antibodies that are substantially encoded by a recognized immunoglobulin alpha gene. In humans, this class or isotype includes $IgA_1$ and $IgA_2$. IgA antibodies can exist as monomers, polymers (referred to as pIgA) of predominantly dimeric form, and secretory IgA. The constant chain of wild-type IgA contains an 18-amino-acid extension at its C-terminus called the tail piece (tp). Polymeric IgA is secreted by plasma cells with a 15-kDa peptide called the J chain linking two monomers of IgA through the conserved cysteine residue in the tail piece.

IgG: A polypeptide belonging to the class or isotype of antibodies that are substantially encoded by a recognized immunoglobulin gamma gene. In humans, this class includes $IgG_1$, $IgG_2$, $IgG_3$, and $IgG_4$. In mice, this class includes $IgG_1$, $IgG_{2a}$, $IgG_{2b}$, and $IgG_3$.

Immune complex: The binding of antibody to a soluble antigen forms an immune complex. The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Increase: To increase the quality, amount, or strength of something; for example phosphorylation at position 1989 of ATR. In one example, an agent increase phosphorylation at position 1989 of ATR, for example as compared to phosphorylation in the absence of the agent.

In a particular example, a therapy increase the phosphorylation at position 1989 of ATR at least about 10%, at least about 20%, at least about 30%, at least about 40%, at least about 50%, at least about 60%, at least about 70%, at least about 80%, at least about 90%, or at least about 100%. Such increase can be measured using the methods disclosed herein.

Inhibiting or Treating a Disease: A therapeutic intervention (for example, a pharmaceutical compound) that reduces a sign or symptom of a disease or pathological condition related to a disease (such as a tumor). Treatment can also induce remission or cure of a condition, such as a tumor. In particular examples, treatment includes preventing a tumor, for example by inhibiting the full development of a tumor, such as preventing development of a metastasis or the development of a primary tumor. Prevention does not require a total absence of a tumor.

Reducing a sign or symptom of a disease or pathological condition related to a disease, refers to any observable beneficial effect of the treatment. Reducing a sign or symptom associated with a tumor (such as pathological angiogenesis) can be evidenced, for example, by a delayed onset of clinical symptoms of the disease in a susceptible subject (such as a subject having a tumor which has not yet metastasized), a reduction in severity of some or all clinical symptoms of the disease, a slower progression of the disease (for example by prolonging the life of a subject having tumor), a reduction in the number of relapses of the disease, an improvement in the overall health or well-being of the subject, or by other parameters well known in the art that are specific to the particular tumor. A "prophylactic" treatment is a treatment administered to a subject who does not exhibit signs of a disease or exhibits only early signs for the purpose of decreasing the risk of developing pathology.

Isolated and Purified: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. A isolated or purified nucleic acid, peptide or protein, for example an antibody or ATR, can be at least 50%, at least 60%, at least 70%, at least 80%, at least 90%, at least 95%, at least 96%, at least 97%, at least 98%, or at least 99% pure.

Linker: A bi-functional molecule that can be used to link two molecules into one contiguous molecule, for example, to link an effector molecule or a detectable marker to an antibody. In some embodiments, the provided conjugates include a linker between the effector molecule or detectable marker and an antibody. In some embodiments, the linker is cleavable under intracellular conditions, such that cleavage of the linker releases the effector molecule or detectable marker from the antibody in the intracellular environment. In yet other embodiments, the linker is not cleavable and the effector molecule or detectable marker can be released, for example, by antibody degradation. In some cases, a linker is a peptide within an antibody binding fragment (such as an Fv fragment) which serves to indirectly bond the variable heavy chain to the variable light chain.

The terms "conjugating," "joining," "bonding," or "linking" refer to making two molecules into one contiguous molecule; for example, linking two polypeptides into one contiguous polypeptide, or covalently attaching an effector molecule or detectable marker radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors including an amplified or assembled nucleic acid which can be used to transform a suitable host cell. A host cell that includes the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers provided herein are conventional. *Remington's Pharmaceutical Sciences*, by E. W. Martin, Mack Publishing Co., Easton, Pa., 15th Edition (1975), describes compositions and formulations suitable for pharmaceutical delivery.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced. A polypeptide has an amino terminal (N-terminal) end and a carboxy-terminal end. In some embodiments, the polypeptide is a disclosed antibody or a fragment thereof.

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci.* USA 89:10915, 1989). An oligonucleotide is a linear polynucleotide sequence of up to about 100 nucleotide bases in length.

Specifically bind: When referring to an antibody, refers to a binding reaction which determines the presence of a target protein, peptide, or polysaccharide in the presence of a heterogeneous population of proteins and other biologics. Thus, under designated conditions, an antibody binds preferentially to a particular target protein or peptide (such as an epitope of ATR that includes T1989 and is phosphorylated at position 1989) and does not bind in a significant amount to other proteins or peptides (such as an epitope of ATR that includes T1989 but that is not phosphorylated at position 1989). Specific binding can be determined by methods known in the art. With reference to an antibody antigen complex, specific binding of the antigen and antibody has a $K_d$ of less than about $10^{-7}$ Molar (M), such as less than about $10^{-8}$ M, $10^{-9}$ M, $10^{-10}$ M, or even less than about $10^{-11}$ M.

The antibodies disclosed herein specifically bind only to a defined target (or multiple targets, in the case of a bispecific antibody). Thus, an antibody that specifically binds to pT1989 ATR is an antibody that binds substantially to only pT1989 ATR, including cells or tissue expressing pT1989 ATR, a substrate to which the pT1989 ATR is attached, or pT1989 ATR in a biological specimen. It is, of course, recognized that a very small degree of non-specific interaction may occur between an antibody or conjugate including an antibody (such as an antibody that specifically binds pT1989 ATR or conjugate including such antibody) and a non-target (such as a cell that does not express pT1989 ATR or ATR not phosphorylated at T1989). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Subject: Any mammal, such as humans, non-human primates, pigs, sheep, cows, rodents, and the like. In two non-limiting examples, a subject is a human subject or a murine subject. Thus, the term "subject" includes both human and veterinary subjects.

Therapeutically effective amount or Effective Amount: The amount of an agent (such as a pharmaceutical compound, antibody, antigen binding fragment or conjugate) that alone, or together with one or more additional agents, induces the desired response, such as, for example treatment of a tumor or identification of a specific protein. Ideally, a therapeutically effective amount provides a therapeutic effect without causing a substantial cytotoxic effect in the subject. In one example, a desired response is to decrease the size, volume, or number (such as metastases) of a tumor in a subject.

Several preparations disclosed herein are administered in therapeutically effective amounts. A therapeutically effective amount of an agent, such as, but not limited to, a chemotherapeutic agent, that is administered to a human or veterinary subject will vary depending upon a number of factors associated with that subject, for example the overall health of the subject. A therapeutically effective amount can be determined by varying the dosage and measuring the resulting therapeutic response, such as the regression of a tumor. Therapeutically effective amounts also can be determined through various in vitro, in vivo or in situ immunoassays. The disclosed agents can be administered in a single dose, or in several doses, as needed to obtain the desired response. However, the therapeutically effective amount can be dependent on the source applied, the subject being treated, the severity and type of the condition being treated, and the manner of administration.

Tumor: An abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharygioma, ependymoma, pinealoma, hemangioblastoma, acoustic neuroma, oligodendroglioma, meningioma, melanoma, neuroblastoma and retinoblastoma).

Under conditions sufficient for: A phrase that is used to describe any environment that permits a desired activity. In one example the desired activity is formation of an immune complex. In particular examples the desired activity is treatment of a tumor.

II. Description of Several Embodiments

A. Monoclonal Antibodies

The threonine at position 1989 of ATR (T1989) is a DNA damage-regulated phosphorylation site; activation of ATR in vivo results in phosphorylation of this threonine (pT1989). Selective inhibition of ATR prevents phosphorylation at T1989.

Isolated monoclonal antibodies that specifically bind to pT1989 ATR, antigen binding fragments of such antibodies, conjugates thereof, and methods of using these molecules, are provided herein. The antibodies can be chimeric or humanized. Also disclosed herein are compositions including these monoclonal antibodies and a pharmaceutically acceptable carrier. Nucleic acids encoding these antibodies, expression vectors comprising these nucleic acids, and isolated host cells that express the nucleic acids are also provided. These antibodies have a high sensitivity and specificity, and can be used to detect pT1989 in biological samples.

Compositions comprising the monoclonal antibodies specific for pT1989 ATR can be used for drug screening and diagnostic purposes. These monoclonal antibodies can also be used to determine if a pharmacologic agent, such as a chemotherapeutic agent, is of use for treating a subject, and/or to determine the dose of the agent that is effective for treating a subject.

In several embodiments, the monoclonal antibodies include a heavy chain comprising a heavy chain complementarity determining region (HCDR)1, a HCDR2 and an HCDR3, and a light chain comprising a light chain complementarity determining region (LCDR) 1, LCDR2 and LCDR3. The disclosed antibodies specifically bind to pT1989 ATR. In some embodiments, the pT1989 ATR specific antibodies include a variable heavy ($V_H$) and a variable light ($V_L$) chain and specifically bind pT1989 ATR. In several embodiments, the antibody or antigen binding fragment thereof includes heavy and light chain variable regions including the HCDR1, HCDR2 and HCDR3 of the amino acid sequence set forth as SEQ ID NO: 6 and LCDR1, LCDR2, and LCDR3 of the amino acid sequence set forth as SEQ ID NO: 7. These sequences are shown below

```
                                               (SEQ ID NO: 6)
ETGLRWLLLVAVLKGVQCQSVEESGGRLVAPGTPLTLTCTVSGIDLMYNA

MNWVRQAPGKGLEFIGMIGSGGNTVYASWAKGRFTISKTSTTVGLKMTSL

TQEDTATYFCAREGSGGSMDFWGPGTLVTVSSGQPKAPSVFPLAPCCGDT

PSSTVTLGCLVKGYLPEPVTVTWNSGTLTNGVRTFPSVRQSSGLYSLSSV

VSVTSSSQPVTCNVAHPATNTKVDKTVAPSTCSKPTCPPPELLGGPSVFI

FPPKPKDTLMISRTPEVTCVVVDVSQDDPEVQFTWYINNEQVRTARPPLR

EQQFNSTIRVVSTLPIAHQDWLRGKEFKCKVHNKALPAPIEKTISKARGQ

PLEPKVYTMGPPREELSSRSVSLTCMINGFYPSDISVEWEKNGKAEDNYK

TTPAVLDSDGSYFLYSKLSVPTSEWQRGDVFTCSVMHEALHNHYTQKSIS

RSPGK (SEQ ID NO: 7)
DTRAPTQLLGLLLLWLPGATFALVMTQSPSSVSAAVGGTVTITCQASQSL

YNNNYLAWFQQKPGQRPKLLIYKASTLASGVPSRFKGSGSGTQFTLTISD

LECEDAATYYCLGEYKDNVDDGNAFGGGTEVVVEGDPVAPTVLIFPPAAD

QVATGTVTIVCVANKYFPDVTVTWEVDGTTQTTGIENSKTPQNSADCTYN

LSSTLTLTSTQYNSHKEYTCKVTQGTTSVVQSFNRGDC
```

The discussion of monoclonal antibodies below refers to isolated monoclonal antibodies that include heavy and light chain variable domains including at least one complementarity determining region (CDR), such as a CDR1, CDR2 and CDR3. The person of ordinary skill in the art will understand that various CDR numbering schemes (such as the Kabat, Chothia or IMGT numbering schemes) can be used to determine CDR positions. The person of skill in the art will readily understand use of various CDR numbering schemes when referencing particular amino acids of the antibodies disclosed herein.

Figure 13B:
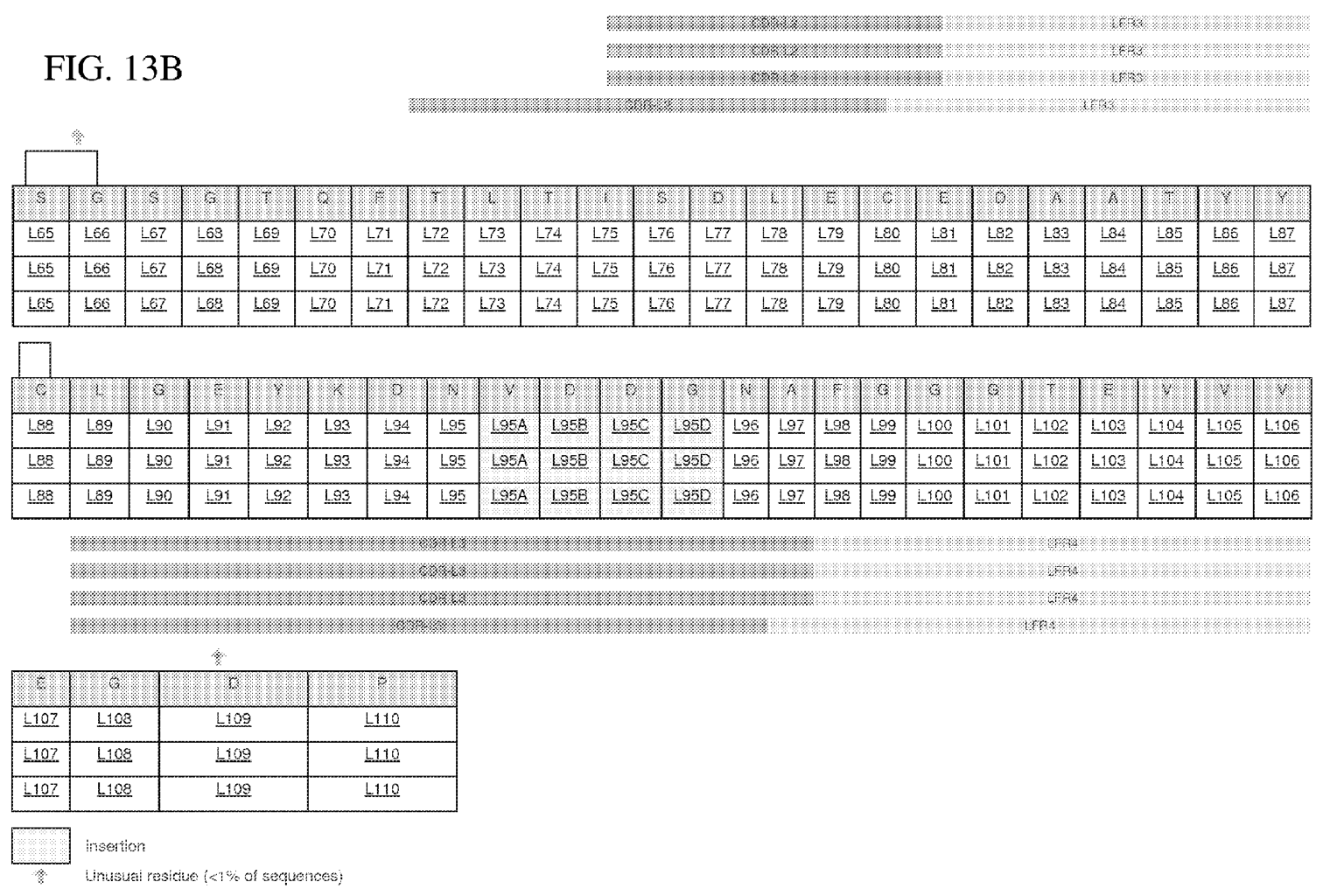
Figure 13C:
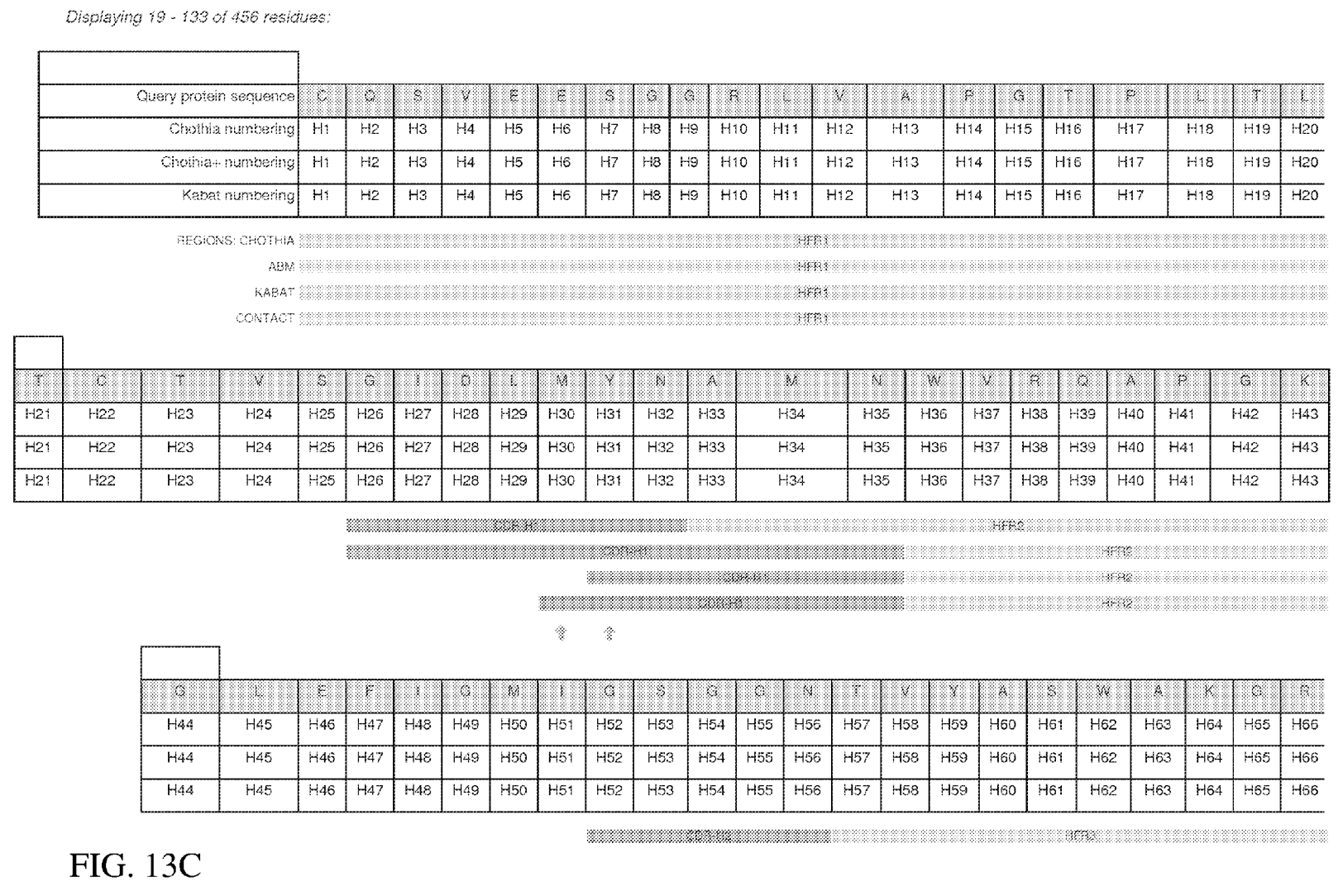
Figure 13D:
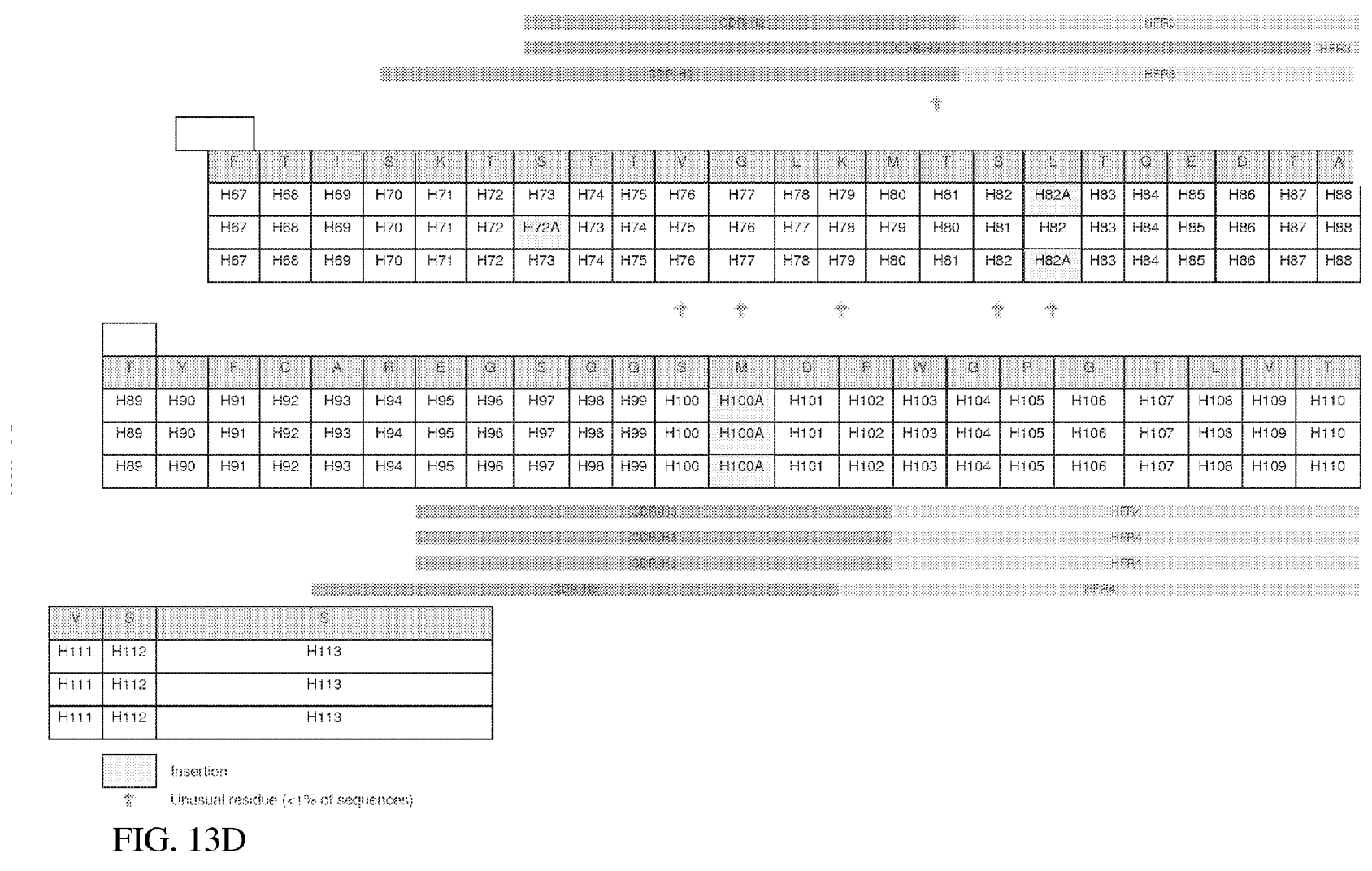

The antibody, or an antigen binding fragment thereof, can include the HCDR1, HCDR2, and/or HCDR3 of SEQ ID NO: 6, and the LCDR1, LCDR2, and/or LCDR3 of SEQ ID NO: 7, and specifically bind pT1989 ATR. In specific, non-liming examples, both the heavy and light chain CDRs are identified by Kabat, Chothia or IMGT numbering. Thus, the antibody or an antigen binding fragment thereof can include the HCDR1, HCDR2, and HCDR3 of SEQ ID NO: 6, and the LCDR1, LCDR2, and LCDR3 of SEQ ID NO: 7, and specifically bind pT1989 ATR. In specific non-limiting examples, the heavy and light chain CDRs are identified by Kabat, Chothia or IMGT numbering. It should be noted that the CDRs can be identified using other methods known to those of skill in the art, for example, Contact and Enhanced Chothia (also called Chothia+, see FIG. 13).

In some embodiments, the antibody or antigen binding fragment includes a heavy chain variable region including a HCDR1, HCDR2, and/or HCDR3 including amino acids 48-52, 67-82, and 113-121 (H31-H35, H50-H65 and H95-H102 using Kabat numbering) of SEQ ID NO: 6, respectively. In further embodiments, the antibody or antigen binding fragment includes a heavy chain variable region including a HCDR1, HCDR2, and/or HCDR3 including amino acids 43-49, 69-73, and/or 113-121 (H26-H32, H52-H56 and H95-H102 using Chothia numbering) of SEQ ID NO: 6, respectively. In other embodiments, the antibody or antigen binding fragment includes a heavy chain variable region including a HCDR1, HCDR2, and HCDR3 including amino acids 48-52, 67-82, and 113-121 (H31-H35, H50-H65 and H95-H102 using Kabat numbering) of SEQ ID NO: 6, respectively. In additional embodiments, the antibody or antigen binding fragment includes a heavy chain variable region including a HCDR1, HCDR2, and HCDR3 including amino acids 43-49, 69-73, and 113-121 (H26-H32, H52-H56 and H95-H102 using Chothia numbering) of SEQ ID NO: 6, respectively.

In some embodiments, the antibody or antigen binding fragment includes a light chain variable region including a LCDR1, LCDR2, and/or LCDR3 including amino acids 45-57, 73-79 and/or 112-124 (L24-L34, L50-L56, and L89-L97 using Kabat numbering and L24-L34, L50-L56, and L89-L97 using Chothia numbering) of SEQ ID NO: 7, respectively. In other embodiments, the antibody or antigen binding fragment includes a light chain variable region including a LCDR1, LCDR2, and LCDR3 including amino acids 45-57, 73-79 and/or 112-124 (L24-L34, L50-L56, and L89-L97 using Kabat numbering and L24-L34, L50-L56, and L89-L97 using Chothia numbering) of SEQ ID NO: 7, respectively.

In specific non-limiting examples, the antibody or antigen binding fragment includes a heavy chain variable region including a HCDR1, HCDR2, and HCDR3 including amino acids 48-52, 67-82, and 113-121 (H31-H35, H50-H65 and H95-H102 using Kabat numbering) of SEQ ID NO: 6. The antibody or antigen binding fragment also includes a light chain variable region including a LCDR1, LCDR2, and LCDR3 including amino acids 45-57, 73-79 and/or 112-124 (L24-L34, L50-L56, and L89-L97 using Kabat numbering and L24-L34, L50-L56, and L89-L97 using Chothia numbering) of SEQ ID NO: 7.

In additional non-limiting examples, the antibody or antigen binding fragment includes a heavy chain variable region including a HCDR1, HCDR2, and HCDR3 including amino acids 43-49, 69-73, and 113-121 (H26-H32, H52-H56 and H95-H102 using Chothia numbering) of SEQ ID NO: 6. The antibody or antigen binding fragment also includes a light chain variable region including a LCDR1, LCDR2, and LCDR3 including amino acids 45-57, 73-79 and/or 112-124 (L24-L34, L50-L56, and L89-L97 using Kabat numbering and L24-L34, L50-L56, and L89-L97 using Chothia numbering) of SEQ ID NO: 7.

In some embodiments, the antibody includes a heavy chain variable region including an amino acid sequence at least 95%, 96%, 97%, 98%, or 99% identical to the amino acid sequence set forth as SEQ ID NO: 6. In more embodiments, the antibody includes a light chain variable region including an amino acid sequence at least 95%, 96%, 97%, 98%, or 99% identical to the amino acid sequence set forth as SEQ ID NO: 7. In additional embodiments, the antibody includes a heavy chain variable region including an amino acid sequence at least 95%, 96%, 97%, 98%, or 99% identical to the amino acid sequence set forth as SEQ ID NO: 6, and a light chain variable region including an amino acid sequence at least 95%, 96%, 97%, 98%, or 99% identical to the amino acid sequence set forth as SEQ ID NO: 7.

In additional embodiments, the antibody includes a heavy chain variable region including, or consisting of, the amino acid sequence set forth as SEQ ID NO: 6. In more embodiments, the antibody includes a light chain variable region including, or consisting of, the amino acid sequence set forth as SEQ ID NO: 7. In yet other embodiments, the antibody includes a heavy chain variable domain including, or consisting of, the amino acid sequence set forth as SEQ ID NO: 6 and a light chain variable domain including, or consisting of, the amino acid sequence set forth as SEQ ID NO: 7.

In several embodiments, the disclosed antibodies can specifically bind pT1989 ATR with an affinity of at least about $1.0 \times 10^{-8}$M, at least about $5.0 \times 10^{-8}$M, at least about $1.0 \times 10^{-9}$M, at least about $5.0 \times 10^{-9}$M, at least about $1.0 \times 10^{-10}$ M, at least about $5.0 \times 10^{-10}$ M, or at least about $1.0 \times 10^{-11}$M. In additional embodiments, the antibody does not significantly bind ATR that is not phosphorylated at position 1989 (T1989 ATR). In additional embodiments, the disclosed antibodies specifically bind the amino acid sequence set forth as SEQ ID NO: 2 and/or the amino acid sequence set forth as SEQ ID NO: 3 with an affinity of at least about $1.0 \times 10^{-9}$M, at least about $5.0 \times 10^{-9}$M, at least about $1.0 \times 10^{-10}$ M, at least about $5.0 \times 10^{-10}$ M, or at least about $1.0 \times 10^{-11}$M. In specific non-liming examples, the disclosed antibodies specifically bind the amino acid sequence set forth as SEQ ID NO: 2 and/or the amino acid sequence set forth as SEQ ID NO: 3 with an affinity of at least about at least about $1.0 \times 10^{-10}$ M.

The monoclonal antibodies can be rabbit monoclonal antibodies. Chimeric antibodies are also provided. The antibodies can include any suitable framework region, such as (but not limited to) a human, mouse, rat, goat, sheep, or a rabbit framework region. Human framework regions, and mutations that can be made in a human antibody framework regions, are known in the art (see, for example, in U.S. Pat. No. 5,585,089, which is incorporated herein by reference). Alternatively, a heterologous framework region, such as, but not limited to a mouse framework region, can be included in the heavy or light chain of the antibodies. (See, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993.)

In some embodiments, an antibody that specifically binds pT1989 ATR as disclosed herein includes up to 10 amino acid substitutions (such as up to 1, 2, 3, 4, 5, 6, 7, 8, or up to 9 amino acid substitutions) in the framework regions of the heavy chain of the antibody, or the light chain of the antibody, or the heavy and light chains of the antibody.

The antibodies or antigen binding fragments disclosed herein can be derivatized or linked to another molecule (such as another peptide or protein). In general, the antibodies or portion thereof is derivatized such that the binding to pT1989 ATR is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detectable marker, an effector molecule, or a protein or peptide that can mediate association of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

The monoclonal antibodies disclosed herein can be of any isotype. The monoclonal antibody can be, for example, an IgM or an IgG antibody, such as IgG$_1$, IgG$_2$, IgG$_3$ or an IgG$_4$. The class of an antibody that specifically binds pT1989 ATR can be switched with another (for example, IgG can be switched to IgM), according to well-known procedures. For example, a nucleic acid molecule encoding the V$_L$ or V$_H$ of a disclosed antibody can be operatively linked to a nucleic acid sequence encoding a C$_L$ or C$_H$ from a different class of immunoglobulin molecule. This can be achieved using a vector or nucleic acid molecule that comprises a C$_L$ or C$_H$ chain, as known in the art. For example, an antibody that specifically binds pT1989 ATR, that was originally IgG may be class switched to an IgM. Class switching can be used to convert one IgG subclass to another, such as from IgG$_1$ to IgG$_2$, IgG$_3$, or IgG$_4$.

In some examples, the disclosed antibodies are oligomers of antibodies, such as dimers, trimers, tetramers, pentamers, hexamers, septamers, octomers and so on. In some examples, the antibodies are pentamers.

B. Conjugates

Human monoclonal antibodies specific for pT1989 ATR, or antigen binding fragments thereof, can be conjugated to an agent, such as an effector molecule or detectable marker, using any number of means known to those of skill in the art. Both covalent and non-covalent attachment means may be used. Conjugates include, but are not limited to, molecules in which there is a covalent linkage of an effector molecule or a detectable marker to an antibody or antigen binding fragment that specifically binds pT1989 ATR. One of skill in the art will appreciate that various effector molecules and detectable markers can be used, including (but not limited to) chemotherapeutic agents, toxins, radioactive agents such as $^{125}$I, $^{32}$P, $^{14}$C, $^{3}$H and $^{35}$S and other labels, target moieties and ligands, etc.

A monoclonal antibody that specifically binds pT1989 ATR (or antigen binding fragment thereof) can be conjugated with a detectable marker; for example, a detectable marker capable of detection by ELISA, spectrophotometry, flow cytometry, microscopy or diagnostic imaging techniques. The detectable marker may be synthetic markers that are non-naturally occurring. Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

An antibody or antigen binding fragment can be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

An antibody or antigen binding fragment can be conjugated with a radiolabeled amino acid. The radiolabel may be used for both diagnostic and therapeutic purposes. For instance, the radiolabel may be used to detect pT1989 ATR and pT1989 ATR-expressing cells by x-ray, emission spectra, or other diagnostic techniques. Examples of labels for polypeptides include, but are not limited to, the following radioisotopes or radionucleotides: $^{3}$H, $^{14}$C, $^{15}$N, $^{35}$S, $^{90}$Y, $^{99}$Tc, $^{111}$In, $^{125}$I, $^{131}$I.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The choice of a particular detectable marker (or effector molecule) depends, amongst other things, on the particular cell, the desired biological effect, and/or the detection method. Thus, for example, the effector molecule can be a cytotoxin that is used to bring about the death of a particular target cell, or a fluorescent molecule can be used if visualization will use fluorescent light. Any effector molecule that can be detected, such as by using another antibody, can be utilized in the detection methods disclosed herein. This includes proteins, particles and other agents.

Effector molecules and detectable markers can be linked to an antibody or antigen binding fragment of interest using any number of means known to those of skill in the art. Both covalent and noncovalent attachment means may be used. The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody, or antigen binding fragment, and to the effector molecule or detectable label. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

Additionally, in several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. No. 7,964,5667, 498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference in its entirety.

Thus, in several embodiments, the conjugate includes a linker that connects the effector molecule or detectable marker to the pT1989 ATR-specific antibody or antigen binding fragment thereof. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15, amino acids long. In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker not released.

The antibodies or antigen binding fragments disclosed herein can be derivatized, for example, by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

In view of the large number of methods that have been reported for attaching a variety of radiodiagnostic compounds, radiotherapeutic compounds, labels (such as enzymes or fluorescent molecules), toxins, and other agents to antibodies one skilled in the art will be able to determine a suitable method for attaching a given agent to an antibody or antigen binding fragment or other polypeptide. For example, the antibody or antigen binding fragment can be conjugated with small molecular weight drugs such as Monomethyl Auristatin E (MMAE), Monomethyl Auristatin F (MMAF), maytansine, maytansine derivatives, including the derivative of maytansine known as DM1 (also known as mertansine), or other agents.

The average number of effector molecule or detectable marker moieties per antibody or antigen binding fragment in a conjugate can range, for example, from 1 to 20 moieties per antibody or antigen binding fragment. For some conjugates, the average number of effector molecule or detectable marker moieties per antibody or antigen binding fragment may be limited by the number of attachment sites on the antibody or antigen binding fragment. For example, where the attachment is a cysteine thiol, an antibody or antigen binding fragment may have only one or several cysteine thiol groups, or may have only one or several sufficiently reactive thiol groups through which a linker may be attached. In certain embodiments, the average number of effector molecule or detectable marker moieties per antibody or antigen binding fragment in a conjugate range from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. See, for example, U.S. Pat. No. 7,498,298, incorporated by reference herein in its entirety. The average number of effector molecule or detectable marker moieties per antibody or antigen binding fragment in preparations of conjugates may be characterized by conventional means such as mass spectroscopy and, ELISA assay.

The loading (for example, effector molecule (such as a detectable marker)/antibody ratio) of an conjugate may be controlled in different ways, for example, by: (i) limiting the molar excess of effector molecule-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number or position of linker-effector molecule attachments (such as thioMab or thioFab prepared as disclosed in WO2006/03448, incorporated by reference herein in its entirety.

C. Nucleotides, Expression Vectors and Host Cells

Nucleic acids encoding the amino acid sequences of antibodies that specifically bind pT1989 ATR are provided. Nucleic acid molecules encoding these antibodies can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same effector molecule, detectable marker or antibody or antigen binding fragment sequence.

Nucleic acid sequences encoding the antibodies that specifically bind pT1989 ATR can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template.

Exemplary nucleic acids including sequences encoding an antibody that specifically binds pT1989 ATR (or antigen binding fragment thereof) can be prepared by cloning techniques.

In some embodiments, the heavy chain is encoded by the nucleic acid sequence set forth as:

(SEQ ID NO: 8)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCGCCCCTGGGA

```
-continued
CACCCCTGACACTCACCTGTACCGTCTCTGGAATCGACCTCATGTACAAT

GCAATGAACTGGGTCCGCCAGGCTCCAGGGAAGGGCCTGGAATTCATCGG

AATGATTGGTAGTGGTGGTAATACAGTCTATGCGAGCTGGGCGAAAGGCC

GATTCACCATCTCCAAAACCTCGACCACGGTGGGTCTGAAGATGACCAGT

CTGACACAGGAGGACACGGCCACCTATTTCTGTGCCAGAGAGGGTAGTGG

TGGCAGTATGGACTTCTGGGGCCCAGGCACCCTGGTCACCGTCTCCTCAG

GGCAACCTAAGGCTCCATCAGTCTTCCCACTGGCCCCCTGCTGCGGGAC

ACACCCAGCTCCACGGTGACCCTGGGCTGCCTGGTCAAAGGGTACCTCCC

GGAGCCAGTGACCGTGACCTGGAACTCGGGCACCCTCACCAATGGGGTAC

GCACCTTCCCGTCCGTCCGGCAGTCCTCAGGCCTCTACTCGCTGAGCAGC

GTGGTGAGCGTGACCTCAAGCAGCCAGCCCGTCACCTGCAACGTGGCCCA

CCCAGCCACCAACACCAAAGTGGACAAGACCGTTGCGCCCTCGACATGCA

GCAAGCCCACGTGCCCACCCCCTGAACTCCTGGGGGACCGTCTGTCTTC

ATCTTCCCCCCAAAACCCAAGGACACCCTCATGATCTCACGCACCCCCGA

GGTCACATGCGTGGTGGTGGACGTGAGCCAGGATGACCCCGAGGTGCAGT

TCACATGGTACATAAACAACGAGCAGGTGCGCACCGCCCGGCCGCCGCTA

CGGGAGCAGCAGTTCAACAGCACGATCCGCGTGGTCAGCACCCTCCCCAT

CGCGCACCAGGACTGGCTGAGGGGCAAGGAGTTCAAGTGCAAAGTCCACA

ACAAGGCACTCCCGGCCCCCATCGAGAAAACCATCTCCAAAGCCAGAGGG

CAGCCCCTGGAGCCGAAGGTCTACACCATGGGCCCTCCCCGGGAGGAGCT

GAGCAGCAGGTCGGTCAGCCTGACCTGCATGATCAACGGCTTCTACCCTT

CCGACATCTCGGTGGAGTGGGAGAAGAACGGGAAGGCAGAGGACAACTAC

AAGACCACGCCGGCCGTGCTGGACAGCGACGGCTCCTACTTCCTCTACAG

CAAGCTCTCAGTGCCCACGAGTGAGTGGCAGCGGGGCGACGTCTTCACCT

GCTCCGTGATGCACGAGGCCTTGCACAACCACTACACGCAGAAGTCCATC

TCCCGCTCTCCGGGTAAATGA.
```

In additional embodiments, the light chain is encoded by the nucleic acid sequence set forth as:

```
                                             (SEQ ID NO: 9)
ATGGACACGAGGGCCCCCACTCAGCTGCTGGGGCTCCTGCTGCTCTGGCT

CCCAGGTGCCACATTTGCCCTGGTGATGACCCAGTCTCCATCCTCCGTGT

CTGCAGCTGTGGGAGGCACAGTCACCATCACTTGCCAGGCCAGTCAGAGT

CTTTATAATAACAACTACTTAGCCTGGTTTCAGCAGAAACCAGGGCAGCG

TCCCAAGCTCCTGATCTACAAGGCATCCACTCTGGCAAGTGGGGTCCCAT

CGCGCTTCAAAGGCAGTGGATCTGGGACACAGTTCACTCTCACCATCAGC

GACCTGGAGTGTGAAGATGCTGCCACTTACTACTGCCTAGGCGAATATAA

GGATAATGTAGATGATGGTAATGCTTTCGGCGGAGGGACCGAGGTGGTGG

TCGAAGGTGATCCAGTTGCACCTACTGTCCTCATCTTCCCACCAGCTGCT

GATCAGGTGGCAACTGGAACAGTCACCATCGTGTGTGTGGCGAATAAATA

CTTTCCCGATGTCACCGTCACCTGGGAGGTGGATGGCACCACCCAAACAA

CTGGCATCGAGAACAGTAAAACACCGCAGAATTCTGCAGATTGTACCTAC
```

```
-continued
AACCTCAGCAGCACTCTGACACTGACCAGCACACAGTACAACAGCCACAA

AGAGTACACCTGCAAGGTGACCCAGGGCACGACCTCAGTCGTCCAGAGCT

TCAATAGGGGTGACTGTTAG
```

SEQ ID NO: 8 and SEQ ID NO: 9 include an ATG encoding the N terminal methionine. In some embodiments, this ATG is deleted. Examples of appropriate cloning and sequencing techniques, and instructions sufficient to direct persons of skill through cloning are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one example, an antibody or antigen binding fragment of use is prepared by inserting the cDNA which encodes a variable region from an antibody into a vector which includes the cDNA encoding an effector molecule or detectable marker, such as an enzyme or label. The insertion is made so that the variable region and the effector molecule or detectable marker are read in frame so that one continuous polypeptide is produced. Thus, the encoded polypeptide contains a functional Fv region and a functional effector molecule or detectable marker region. In one embodiment, cDNA encoding an enzyme is ligated to a scFv so that the enzyme is located at the carboxyl terminus of the scFv. In several examples, cDNA encoding a horseradish peroxidase or alkaline phosphatase, or a polypeptide marker of interest is ligated to a scFv so that the enzyme (or polypeptide marker) is located at the amino terminus of the scFv. In another example, the label is located at the amino terminus of the scFv. In a further example, cDNA encoding the protein or polypeptide marker is ligated to a heavy chain variable region of an antibody or antigen binding fragment, so that the enzyme or polypeptide marker is located at the carboxyl terminus of the heavy chain variable region. The heavy chain-variable region can subsequently be ligated to a light chain variable region of the antibody or antigen binding fragment using disulfide bonds. In a yet another example, cDNA encoding an enzyme or a polypeptide marker is ligated to a light chain variable region of an antibody or antigen binding fragment, so that the enzyme or polypeptide marker is located at the carboxyl terminus of the light chain variable region. The light chain-variable region can subsequently be ligated to a heavy chain variable region of the antibody or antigen binding fragment using disulfide bonds.

Once the nucleic acids encoding the conjugate, antibody, or antigen binding fragment thereof, are isolated and cloned, the protein can be expressed in a recombinantly engineered cell such as bacteria, plant, yeast, insect and mammalian cells using a suitable expression vector. One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding the antibody or antigen binding fragment or conjugate thereof, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding the antibody, or antigen binding fragment or conjugate thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or antigen binding fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use expression systems such as plasmids and vectors of use in producing proteins in cells including higher eukaryotic cells such as the COS, CHO, HeLa and myeloma cell lines.

Isolation and purification of recombinantly expressed polypeptide can be carried out by conventional means including preparative chromatography and immunological separations. Once expressed, the conjugate, antibody, or antigen binding fragment thereof, can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of single chain antibodies and refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989, all incorporated by reference herein. Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry*, 9: 5015-5021, 1970, incorporated by reference herein, and especially as described by Buchner et al., supra. Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

D. Compositions

Compositions are provided that include one or more of the disclosed conjugates, antibodies, or antigen binding fragments, that specifically bind pT1989 ATR, in a carrier (such as a pharmaceutically acceptable carrier). The compositions can be prepared in unit dosage forms for detection methods.

The compositions for administration can include a solution of the conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody or antigen binding fragment or conjugate in these formulations can vary with the particular method of use selected and the subject's needs. Actual methods of preparing such forms are known, or will be apparent, to those skilled in the art.

Antibodies, antigen binding fragments, or conjugates may be provided in lyophilized form and rehydrated with sterile water before administration, although they are also provided in sterile solutions of known concentration. The antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the reconstitution of antibody or antigen binding fragment and conjugate drugs. Additional agents, including preservatives can be added.

E. Kits

Kits are also provided. For example, kits for detecting a cell that expresses pT1989 ATR in a subject, or determining the dose of a chemotherapeutic agent for administration to a subject. The kits will typically include an antibody or antigen binding fragment that specifically binds pT1989 ATR and/or a conjugate thereof.

More than one of the conjugates or antibodies or antigen binding fragments that specifically bind pT1989 ATR can be included in the kit. Thus, in several non-limiting examples, the kit can include two or more antibodies that specifically bind pT1989 ATR, or an antibody or antigen binding fragment that specifically binds pT1989 ATR and a conjugate thereof, or a combination thereof. In some embodiments, an antigen binding fragment or conjugate including an antigen binding fragment, such as an Fv fragment, is included in the kit. In one example, such as for in vivo uses, the antibody can be a scFv fragment.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed pT1989 ATR specific antibodies, antigen binding fragments, or conjugates. In several embodiments the container may have a sterile access port (for example the container may be an intravenous solution bag or a vial having a stopper pierceable by a hypodermic injection needle).

A label or package insert indicates that the composition is used for detecting pT1989 ATR. The label or package insert typically will further include instructions for use of a disclosed pT1989 ATR specific antibodies or fragments thereof, or conjugates thereof, for example. The package insert typically includes instructions customarily included in commercial packages of products that contain information about the indications, usage, contraindications and/or warnings concerning the use of such products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

F. Methods of Detection

The antibodies disclose herein specifically bind pT1989 and can be used to identify ATR phosphorylated at position 1989 (pT1989 ATR). Methods are provided for detecting the presence of a pT1989 ATR in a cell extract or biological sample, for example detecting a tumor that expresses pT1989 ATR. In some embodiments, the methods include contacting a biological sample or cell extract, such as samples that include tumor cells, or an extract thereof, with one or more of the antibodies that specifically bind pT1989 ATR to form an immune complex. The amount of pT1989 ATR can be quantitated.

A biological sample can be obtained from a mammalian subject of interest, such as human. The biological sample can be cells, bodily fluids, such as blood, derivatives and fractions of blood (such as purified B and/or T cell populations), cerebrospinal fluid; as well as biopsied or surgically removed tissue, for example tissues that are unfixed, frozen, or fixed in formalin or paraffin. The biological sample can be from any organ, including any solid tissue that can be biopsied and blood. The sample can be tissue autopsies and pathology specimens. In specific non-limiting examples, the biological sample is peripheral blood mononuclear cells, cerebral spinal fluid, sputum, or bronchial lavage fluid. In additional non-limiting examples, the biological sample includes circulating tumor cells or circulating cancer stem cells. In additional non-liming examples, the biological sample is ascites fluid, a bone marrow aspirate, a skin punch biopsy or a buccal swab. In further non-liming examples, the sample includes hair follicles. The sample can include circulating endothelial cells.

Thus, methods are provided for detecting a cell that expresses pT1989 ATR, for example, a tumor cell that expresses pT1989ATR, or the amount of pT1989 in a biological sample. In a specific non-limiting example, the cell is a tumor cell. In some embodiments, the tumor is a hematological tumor such as a leukemia, for example an acute leukemia (such as 11q23-positive acute leukemia, acute lymphocytic leukemia, acute myelocytic leukemia, acute myelogenous leukemia and myeloblastic, promyelocytic, myelomonocytic, monocytic and erythroleukemia), or a chronic leukemia (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. In other embodiments, the tumor is a solid tumor, such as a sarcoma or carcinoma, such as a fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancer, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, or a tumor of the central nervous system (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma).

Without being bound by theory, DNA damage, such as, but not limited to, DNA damage caused by ultraviolet light, chemotherapeutic agents, hydroxyurea and replication stress activate ATR. These agents cause polymerases to stall during replication at damage sites on DNA, such that helicases continue to unwind the DNA, leading to long stretches of single-stranded DNA (ssDNA) that result from the continued activity of helicases after replication forks are stalled. These effects activate the ATR pathway. In this pathway, ATR (together with the Rad9-Hus1-Rad1 complex) activates Chk1, which phosphorylates Cdc25A and Cdc25C. Ultimately, the cells arrest in S or G2 (see Wagner and Kaufmann, (2010), *Pharmaceuticals* 3: 1311-1334). Thus, in some embodiments, Cdc25A, Cdc25C, and/or Chk1 activation can be assayed. In additional embodiments, cells are assayed to determine if they are in S or G2 arrest. Assays for Cdc25A, Cdc25C, and/or Chk1 activation are known in the art. Methods for determining cell cycle phase are also known in the art.

In one embodiment, a sample is obtained from a subject, and the presence of pT1989 ATR is assessed in vitro. In additional embodiments, the sample is cells, such as from a cell line, that are cultured in vitro.

These methods can include contacting the sample of interest, or an extract thereof, with an antibody, antigen binding fragment or conjugate provided herein that specifically bind pT1989 ATR to form an immune complex. The presence (or absence) of the immune complex is then detected. The presence of the immune complex indicates the presence of pT1989 ATR. In some non-limiting examples, the amount of pT1989 ATR is quantified. In additional non-limiting examples, the amount of pT1989 ATR is compared to a control. An increase in the presence of this immune complex in the sample, compared to the presence of the immune complex in a control sample, such as a sample not contacted with the antibody or antigen binding fragment, a sample contacted with an unrelated antibody, or a reference standard, detects the presence of cells that express pT1989 ATR in the biological sample. For example, an increase in the presence of the immune complex in the sample as compared to formation of the immune complex in a control sample can indicate the presence of pT1989 in the sample from the subject, or in the cell cultured in vitro.

In some embodiments, the antibody that specifically binds pT1989 ATR or antigen binding fragment is conjugated to a detectable marker. In additional embodiments, the methods include contacting a second antibody that specifically binds the antibody that specifically binds pT1989 ATR, antigen binding fragment thereof, or a conjugate including these molecules, for a sufficient amount of time to form an immune complex, and then detecting the presence of this immune complex. An increase in the presence of this immune complex in a biological sample (as described above) compared to the presence of the immune complex in a control sample, such as a sample not contacted with the antibody or antigen binding fragment, a sample contacted with an unrelated antibody, or a reference standard, detects the presence of cells that express pT1989 ATR in the biological sample. In some examples, the second antibody is conjugated to a detectable marker.

Suitable detectable markers for the antibody, antigen binding fragment, or secondary antibody are described and known to the skilled artisan. For example, various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^{3}H$. Additional examples are disclosed above.

In some embodiments, the assay is an enzyme-linked immunosorbant assay (ELISA) or a radioimmunoassay (RIA). In other embodiments the assay is a Western blot. The antibodies that specifically bind pT1989 ATR and conjugates thereof can be used in immunohistochemical assays. These assays are well known to one of skill in the art (see Harlow & Lane, *Antibodies, A Laboratory Manual*, Cold Spring Harbor Publications, New York (1988), for a description of immunoassay formats.

G. Determining the Effectiveness of Treatment and/or Dose Determination

Methods are disclosed for determining if a tumor can be treated with an ATR inhibitor. As disclosed above, pT1989 ATR is detected in a sample from a subject using the methods disclosed herein. The sample can be any biological sample that includes tumor cells. The presence of pT1989 in the sample indicates that the subject can be treated with an ATR inhibitor.

In some embodiments, methods are provided to determine if a tumor can be treated using an ataxia telangiectasia-mutated and RAD3-related kinase (ATR) inhibitor. The methods include contacting a sample comprising cells from the tumor with an effective amount of the monoclonal antibody or antigen binding fragment that specifically binds ataxia telangiectasia-mutated and RAD3-related kinase phosphorylated at position 1989, under conditions sufficient to form an immune complex; and detecting the presence of the immune complex. In specific non-limiting examples, the presence of the immune complex indicates that the tumor can be treated with the ATR inhibitor. In additional non-limiting examples, absence of the immune complex indicates that the tumor cannot be treated with the ATR inhibitor. In further non-limiting examples, a cut-off value is determined. The presence of an amount the immune complex greater than the cut-off value indicates that the tumor can be treated with the ATR inhibitor. In additional non-limiting examples, the presence of an amount of the immune complex lower than the cut-off value indicates that the tumor cannot be treated with the ATR inhibitor.

Methods are also disclosed herein for determining the effectiveness of a dose, or the duration of a dose, of a therapeutic agent, such as a chemotherapeutic agent. The therapeutic agent can be an ATR inhibitor or a chemotherapeutic agent. The method can determine if a therapeutic agent of interest is of use for treating the subject, or if the therapeutic agent has been administered for a sufficient period of time to treat the subject. In some embodiments, the subject has cancer. The methods can be used to determine the lowest effective therapeutic dose of an agent for the treatment of a subject. These methods include detecting pT1989 ATR in a biological sample from the subject administered the therapeutic agent. In some embodiments, the methods include administering the therapeutic agent to the subject.

In some embodiments, the quantity and molar fraction of phosphorylated ATR is measured as a consequence of drug administration. This fraction may be either increased or decreased. The fraction may be represented as the level of phosphorylation per ATR molecule (such as the ratio of P:ATR ratio) or simply the quantity of pT1989ATR in the specimen.

In some embodiments, the methods can be used to determine the effectiveness of a treatment, for example a treatment for a tumor that expresses pT1989. As disclosed above, pT1989 ATR is detected in a sample from a subject using the methods disclosed herein. The sample can be any biological sample that includes tumor cells.

In some embodiments, the presence and/or amount of pT1989 ATR is determined in a sample from a subject administered a dose of a therapeutic agent of interest. The method includes contacting a biological sample from a subject administered the dose of the therapeutic agent, such as a sample that includes tumor cells, or an extract thereof, with an antibody, or antigen binding fragment thereof, that specifically binds pT1989 ATR, in order to form an immune complex. The presence (or absence) of the immune complex indicates the effectiveness of the treatment. The amount of the immune complex can be quantitated.

In additional embodiments, the amount of the immune complex can be compared to a control, such as the amount of pT1989 ATR in a sample taken prior to the treatment. In some embodiments, a decrease in the amount of pT1989 ATR in the sample, indicates that the first dose of the therapeutic agent is effective for the treatment, and/or that the therapeutic agent has been administered for a sufficient duration of time to treat the subject. In other embodiments, an increase or no change in the amount of the immune complex, as compared to a control, indicates that the first dose of the therapeutic agent is not effective for the treatment and/or that the therapeutic agent has not been administered for a sufficient duration of time to treat the subject.

The biological sample can be any biological sample of interest, such as blood or a fraction thereof (for example, peripheral blood mononuclear cells), an extract from a biopsy or any tissue sample, such as platelets, white blood cell, kidney cells, muscle cells, heart cells, breast cells, brain cells, lung cells, and liver cells, hair follicle cells amongst others. The biological sample can be urine or cerebrospinal fluid. In specific non-limiting examples, the biological sample is peripheral blood mononuclear cells, sputum, or bronchial lavage fluid. In additional non-limiting examples, the biological sample includes circulating tumor cells, circulating blast cells or circulating cancer stem cells. In additional non-liming examples, the biological sample is ascites fluid, a bone marrow aspirate, a skin punch biopsy or a buccal swab. In further non-liming examples, the sample includes hair follicles.

In some embodiments, the sample includes tumor cell. In some embodiments, the tumor is a hematological tumor such as a leukemia, for example an acute leukemia (such as 11q23-positive acute leukemia, acute lymphocytic leukemia, acute myelocytic leukemia, acute myelogenous leukemia and myeloblastic, promyelocytic, myelomonocytic, monocytic and erythroleukemia), or a chronic leukemia (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. In other embodiments, the tumor is a solid tumor, such as a sarcoma or carcinoma, such as a fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancer, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, or a tumor of the central nervous system (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma).

In certain aspects, these assays are performed at a diagnostic laboratory, and the information is then provided to the subject or a physician or other healthcare provider. The methods can further include administration of the therapeutic agent of interest, such as a chemotherapeutic agent, such as an ATR inhibitor.

In some embodiments, the dose of the therapeutic agent is decreased based on the results of the assay, and a second lower dose of the therapeutic agent is administered to the subject. In additional embodiments, these methods can be used to determine the lowest effective dose of the therapeutic agent of use to treat the subject. In yet other embodiments, the dose of the therapeutic is increased based on the results of the assay and administered to the subject. In other examples, and additional dose of the therapeutic agent is administered to the subject.

Thus, in additional embodiments, the method can include administering to the subject a second dose of the therapeutic agent, wherein the second dose is the same, greater, or less than the first dose of the therapeutic agent. The presence (or absence) of pT1989 ATR is then detected in a second biological sample obtained from the subject after administration of the second dose of the therapeutic agent. The biological sample is then contacted with an antibody or antigen binding fragment thereof, that specifically bind pT1989 ATR to form an immune complex. The amount of the immune complex can be quantitated. The presence (or absence) of the immune complex indicates the effectiveness of the treatment.

The amount of the immune complex can be compared to a control, such as the amount of pT1989 ATR in a sample taken from the subject after the first dose of the therapeutic agent, or a standard value. In some embodiments, a decrease or no change in the amount of pT1989 ATR in the sample, as compared to the control, indicates that the second dose of the therapeutic agent is effective for the treatment, and/or that the therapeutic agent has been administered for a sufficient duration of time to treat the subject. In additional embodiments, an increase in the amount of the immune complex, as compared to the control, indicates that the second dose of the therapeutic agent is less effective for the treatment and/or that the therapeutic agent has not been administered for a sufficient duration of time to treat the subject. Thus, in some embodiments, the methods disclosed herein can be repeated to determine the lowest dose of an agent that is effective for the treatment of the subject.

The methods can be repeated 1, 2, 3, 4, 5, 6, 7, 8, 9, 10 or more times to determine the lowest dose of a therapeutic agent that is effective for treating the subject, and/or the shortest duration of administration that is effective for treating the subject. The methods can also be used over the course of a therapeutic regimen to monitor the efficacy of a therapeutic agent for the treatment of the subject. In some embodiments, the lowest amount of a therapeutic agent is determined that inhibits activation of ATR in the subject.

The therapeutic agent can be any ATR kinase inhibitor of interest. In some embodiments, the ATR inhibitor is VE-821

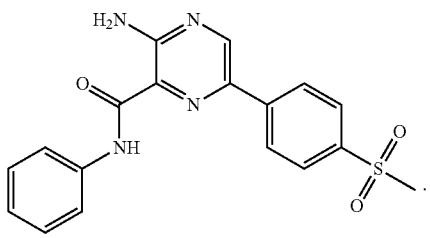 [SMILES: CS(=O)(=O)c1ccc(-c2cnc(N)c(C(=O)Nc3ccccc3)n2)cc1]

In other embodiments, the ATR kinase inhibitor is NU6027

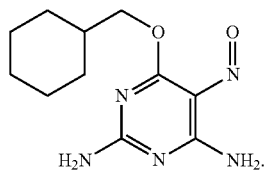 [SMILES: Nc1nc(N)c(N=O)c(OCC2CCCCC2)n1]

In another embodiment, the therapeutic agent is VX-970 (also referred to as VE-822, see Fokas et al., Cell Death & Disease 3: e441, 2012, see also Hall et al., Oncotarget 5: 5674-5685, 2014).

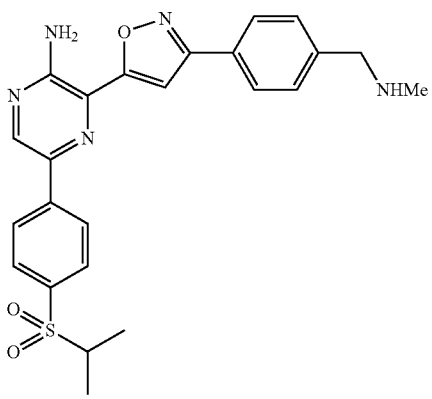 [SMILES: CNCc1ccc(-c2cc(-c3nc(-c4ccc(S(=O)(=O)C(C)C)cc4)cnc3N)on2)cc1]

See also U.S. Published Patent Application No. 20130089626, which is incorporated herein by reference.

The methods disclosed herein can also be used to evaluate the effectiveness of a combination of therapeutic moieties, such as a combination of an ATR inhibitor and another chemotherapeutic compound, ionizing radiation, and DNA damaging agents. The method can also be used to evaluate the effectiveness of a chemotherapeutic agent, ionizing radiation, DNA damaging agent or any other agent of interest. The chemotherapeutic agent can be, for example, an antimetabolite (for example, gemcitabine or cytarabine (cytosine arabinoside), or 5-fluorouracil), a Chk1 inhibitor (for example, XL9844, Exelixis, Inc.), a platinating agent (for example, cisplatin, carboplatin, oxaliplatin), an alkylating agent (for example, mitomycin C, temozolomide, and nitrogen mustards), or a topoisomerase inhibitor (for example camptothecin or etoposide). Suitable agents for combination with an ATR inhibitor can include, but are not limited to, those disclosed for example, in Wagner and Kaufman, 2010, op. cit.

As noted above, the subject can be administered an ATR inhibitor in conjunction with another moiety, such as a chemotherapeutic agent. As noted above, the subject can be administered an ATR inhibitor in conjunction with additional chemotherapeutic agent is a cytotoxic agent such as but not limited to an antimetabolite, a platinating agent, an alkylating agent, or DNA cross-linkers or a targeted agent such as a PARP inhibitor or a checkpoint kinase inhibitor, or ionizing radiation or any other therapeutic that damages DNA either by design or happenstance.

h. Assays for Modulators of ATR

Modulation of ATR can be assessed using a variety of in vitro and in vivo assays, including cell-based models. Such assays can be used to test for inhibitors and activators of ATR. In some embodiments, the assays use any cell that expresses ATR.

In one embodiment, the methods include contacting a biological sample, such as a cell that expresses ATR with the agent of interest. The phosphorylation of T1989 is then detected using the methods disclosed herein. The methods include contacting the cell, or an extract thereof with an antibody, antigen binding fragment or conjugate provided herein that specifically bind pT1989 ATR to form an immune complex. The presence (or absence) of the immune complex is then detected and compared to a control. The control can be the binding of the antibody, antigen binding fragment or conjugate thereof to the cell, or extract thereof, wherein the cell is not contacted with the agent of interest. The control can be a standard value.

An increase in the presence of the immune complex in the sample as compared to formation of the immune complex in a control sample indicates that the agent increases phosphorylation of ATR, and activates ATR. A decrease in the presence of the immune complex in the sample as compared to formation of the immune complex in a control sample indicates that the agent decreases phosphorylation of ATR, and inhibits ATR. In some non-limiting examples, the amount of pT1989 ATR is quantified.

In some examples of the disclosed methods, the antibody that specifically binds pT1989 ATR or antigen binding fragment is conjugated to a detectable marker. In some examples, the methods include contacting a second antibody that specifically binds the antibody that specifically binds pT1989 ATR, antigen binding fragment thereof, or a conjugate including these molecules, for a sufficient amount of time to form an immune complex, and then detecting the presence of this immune complex. In some examples, the second antibody is conjugated to a detectable marker.

In one embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *I Amer. Chem. Soc.* 116:2661 (1994)), oligocarbamates (Cho et al., *Science* 261:1303 (1993)), and/or peptidyl phosphonates (Campbell et al., *I Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996)), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

The compounds tested as modulators of ATR can be any small organic molecule, or a biological entity, such as a protein, e.g., an antibody or peptide, a sugar, a nucleic acid, e.g., an antisense oligonucleotide or a ribozyme or siRNA, or a lipid. Typically, test compounds will be small organic molecules, peptides, circular peptides, siRNA, antisense molecules, ribozymes, and lipids.

Essentially any chemical compound can be used as a potential modulator, although most often compounds can be dissolved in aqueous or organic (especially DMSO-based) solutions. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Any of the assays disclosed herein can be adapted for high throughput screening. In high throughput assays, either soluble or solid state, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

EXAMPLES

The following examples are provided to illustrate particular features of certain embodiments, but the scope of the claims should not be limited to those features exemplified.

Example I

Development of Monoclonal Antibodies

A. Antigen

Design and synthesis of a phospho-peptide comprising of the sequence of amino acids surrounding and including (phospho) threonine 1989 of the ATR protein pT1989-ATR (NP_001175.2) that will produce a suitable immunogen. The peptide included the sequence of amino acids surrounding and including phospho-threonine 1989 of the ATR protein (pT1989-ATR) and be conjugated to C-term and N-term via a terminal Cys. Sequences are shown in FIG. 2. The peptides were then conjugated to KLH and OVA for immunization, and to BSA for ELISA screening. Corresponding non-phospho peptides were made for screening (conjugated to BSA).

B. Immunization

Two three-month old New Zealand white rabbits (ID: E5571 and E5572) were immunized using a protocol of five injections and two test bleeds per rabbit. At the time of each injection, aliquots of peptide mixture (SAIC-1011ap and bp) were thawed and combined with Complete Freund's Adjuvant (CFA) (for the first injection) or with incomplete Freund's Adjuvant (IFA) for the subsequent injections. The injection route was subcutaneous. Immunization details are summarized in Table 1.

TABLE 1

Immunization and Bleed Schedule

| Rabbit ID | Date | Type | immunization/ bleed # | amount | Immunogen |
|---|---|---|---|---|---|
| E5571 | May 15, 2012 | Bleed | 0 | 5 ml | |
| | May 16, 2012 | Injection | 1 | 0.5 mg | mix ap, bp KLH peptides |
| | Jun. 6, 2012 | Injection | 2 | 0.25 mg | mix ap, bp KLH peptides |
| | Jun. 20, 2012 | Injection | 3 | 0.25 mg | mix ap, bp KLH peptides |
| | Jul. 4, 2012 | Injection | 4 | 0.25 mg | mix ap, bp OVA peptides |
| | Jul. 16, 2012 | Bleed | 1 | 5 ml | |
| | Jul. 18, 2012 | Injection | 5 | 0.25 mg | mix ap, bp OVA peptides |
| | Jul. 30, 2012 | Bleed | 2 | 5 ml | |
| E5572 | May 15, 2012 | Bleed | 0 | 5 ml | |
| | May 16, 2012 | Injection | 1 | 0.5 mg | mix ap, bp KLH peptides |
| | Jun. 6, 2012 | Injection | 2 | 0.25 mg | mix ap, bp KLH peptides |
| | Jun. 20, 2012 | Injection | 3 | 0.25 mg | mix ap, bp KLH peptides |
| | Jul. 4, 2012 | Injection | 4 | 0.25 mg | mix ap, bp OVA peptides |
| | Jul. 16, 2012 | Bleed | 1 | 5 ml | |
| | Jul. 18, 2012 | Injection | 5 | 0.25 mg | mix ap, bp OVA peptides |
| | Jul. 30, 2012 | Bleed | 2 | 5 ml | |

KLH: Keyhole limpet hemocyanin, carrier protein for conjugation to antigenic peptide to make them more immunogenic,
OVA: ovalbumin, carrier protein,
ap: peptide a,
bp: peptide b

C. Blood Screening

The titer results from the pair of rabbits for each peptide antigen were determined in a colorimetric ELISA against BSA-conjugated peptides. Plates were coated with 50ng/well peptide-BSA conjugate in bicarbonate buffer pH 9.6 and incubated at 4° C. overnight, then and blocked with 1% BSA in TBS. Diluted (1:250-1:256,000) rabbit anti-sera (50 ul/well) were added and incubated at room temperature. Plates were washed with Tris-buffered saline with 0.05% Tween (TBST). Anti-rabbit secondary conjugated to alkaline phosphatase was used for detection with p-nitrophenyl phosphate (PNPP) substrate. Plates were read at 405 nm with a plate reader. The results are shown in Table 2.

TABLE 2

Bleed Screening Data from Direct ELISA with ATR peptides

| | Peptide - BSA conjugates | | | | | | | |
|---|---|---|---|---|---|---|---|---|
| | ap-BSA | | anp-BSA | | bp-BSA | | bnp-BSA | |
| Bleed # | B1 | B2 | B1 | B2 | B1 | B2 | B1 | B2 |
| | Rabbit ID E5571 | | | | | | | |
| 1:0.25K | 1.23 | 1.22 | 1.14 | 1.14 | 1 | 0.96 | 0.94 | 0.99 |
| 1:1K | 1.3 | 1.26 | 1.25 | 1.21 | 1.09 | 1.05 | 1.07 | 1.05 |
| 1:4K | 1.2 | 1.23 | 1.07 | 1.01 | 1.1 | 0.93 | 0.93 | 0.97 |
| 1:16K | 0.91 | 0.87 | 0.68 | 0.66 | 0.77 | 0.63 | 0.56 | 0.53 |
| 1:64K | 0.47 | 0.43 | 0.32 | 0.31 | 0.4 | 0.33 | 0.28 | 0.29 |
| 1:256K | 0.21 | 0.2 | 0.17 | 0.15 | 0.17 | 0.16 | 0.13 | 0.13 |
| 0 | 0.08 | 0.08 | 0.08 | 0.1 | 0.07 | 0.07 | 0.06 | 0.07 |
| Pre-Bleed | 0.07 | 0.07 | 0.06 | 0.07 | 0.07 | 0.06 | 0.06 | 0.07 |
| | Rabbit ID E5572 | | | | | | | |
| 1:0.25K | 1.17 | 1.13 | 1.19 | 1.18 | 1.03 | 0.98 | 0.94 | 1.07 |
| 1:1K | 1.28 | 1.22 | 1.19 | 1.19 | 1.05 | 0.97 | 1.03 | 1 |
| 1:4K | 1.16 | 1 | 0.96 | 0.96 | 1.04 | 0.87 | 0.89 | 0.9 |
| 1:16K | 0.79 | 0.63 | 0.53 | 0.5 | 0.66 | 0.6 | 0.52 | 0.48 |
| 1:64K | 0.39 | 0.28 | 0.25 | 0.26 | 0.34 | 0.26 | 0.26 | 0.24 |
| 1:256K | 0.18 | 0.13 | 0.13 | 0.13 | 0.16 | 0.13 | 0.13 | 0.12 |
| 0 | 0.07 | 0.06 | 0.09 | 0.09 | 0.07 | 0.08 | 0.07 | 0.07 |
| Pre-Bleed | 0.07 | 0.06 | 0.07 | 0.07 | 0.06 | 0.06 | 0.06 | 0.07 |

Dilution of pre-bleed was 1:60K. Peptide sequences shown in FIG. 2.

Independent screening of blood was conducted. Flat bottom, black, high binding 360 μL plates with clear bottom (VWR catalog #29444-037) were coated with 100 ng/well peptide-BSA conjugate in bicarbonate buffer pH 9.6 (Sigma, catalog # C3041-100CAP) and incubated at 4° C. overnight, then and blocked with ODYSSEY® blocking buffer (LiCor, catalog #927-40010). Diluted (1:250-1:1,000,000) rabbit anti-sera (100 ul/well) were added and incubated at 24 C. Plates were washed with phosphate-buffered saline with 0.05% tween-20 (PBS-T). Anti-rabbit secondary conjugated to IR680 fluorescent dye (LiCor, catalog #926-68021) was used for detection. Plates were read at 700 nm with a Licor ODYSSEY® scanner. Images were quantified using Licor ODYSSEY® application software v3.0 (FIGS. 3 and 4).

Results from both sites indicated Rabbit E5571 had good titers against both phospho-peptides while E5572 has lower titers against the two phospho-peptides. Rabbit E5571 was selected for splenectomy and fusion.

D. Fusion

A final i.v. boost was given and splenectomy was performed. Splenocytes were isolated. Four hundred million lymphocyte cells from each spleen were fused with 200 million fusion partner cells and plated on 40 96-well plates. The plates were kept in tissue culture incubators under standard conditions. Fusion data is shown in Table 3.

TABLE 3

Fusion data

| Rabbit ID | Tissue Type | Weight (g) | Size (cm) | Cell Viability (%) | Total Cells (M) |
|---|---|---|---|---|---|
| E5571 | spleen | 4.06 | 7 | 92 | 2300 |

E. Hybridoma Screening

Figure 5A:
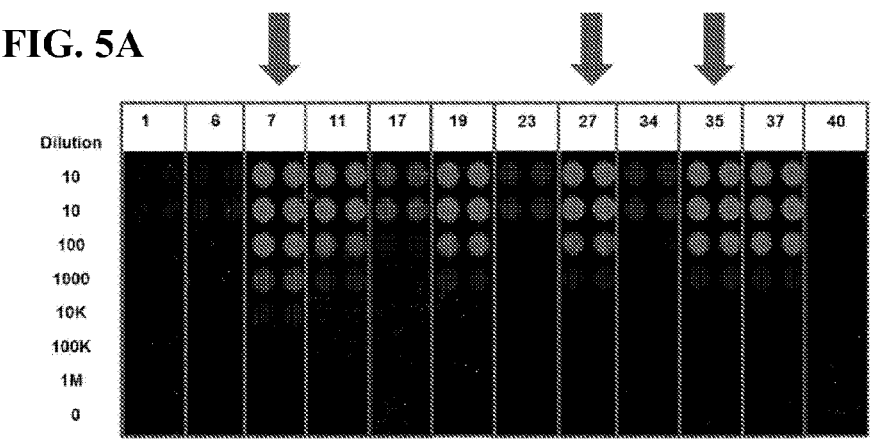
FIGS. 5A-5C. Direct ELISA for dilution of hybridomas against (A) phospho-peptide A (ap). (B) non-phospho-peptide A (anp). Arrows indicate hybridomas that detected pT1989-ATR peptide but did not cross react with unphosphorylated peptide. (C) ATR pT1989 clone 7A7 titers for BSA conjugated phosphorylated and non-phosphorylated peptides. The antibody is specific for the phosphorylated polypeptides.
Figure 5B:
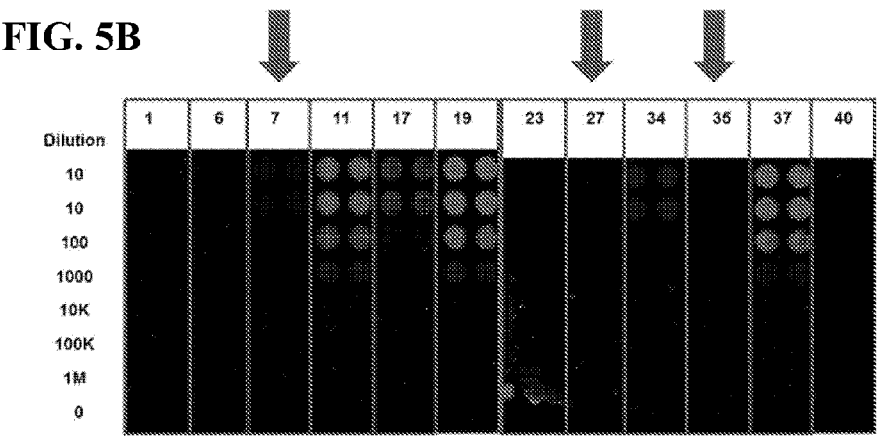
Figure 5C:
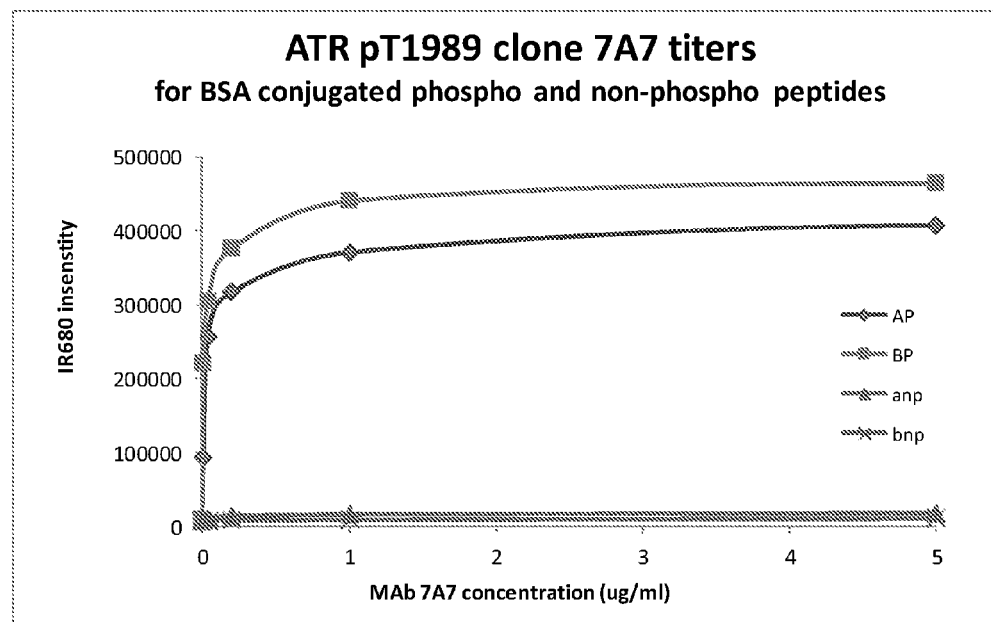
Figure 6:
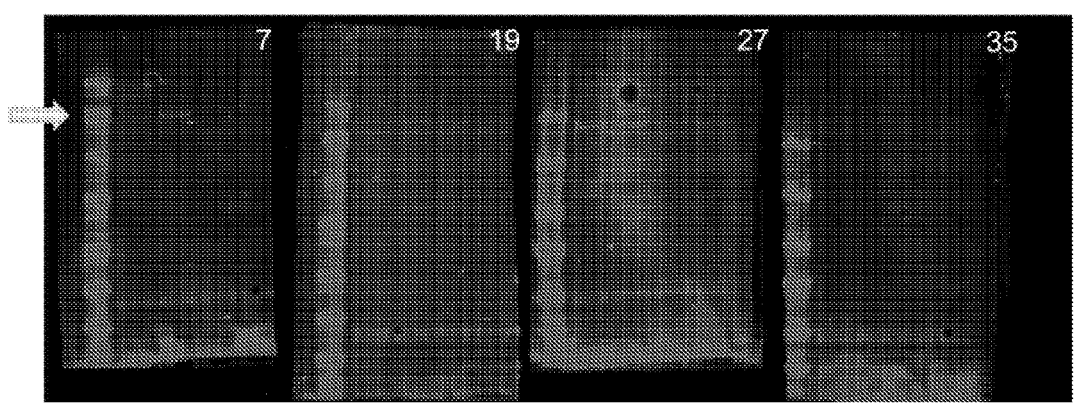
FIG. 6. Western blotting of hybridomas (7, 19, 27 and 35). Lane 1, Molecular weight markers; lane 2, DLD-1 untreated; lane 3 DLD-1 treated with 100 nM gemcitabine for 4 h; lane 4 Seckel cell untreated; lane 5 Seckel cell treated with 100 nM gemcitabine for 4 h. Arrow indicates ATR pT1989 band observed at 250 kDa, corresponding to predicted molecular weight of ATR.

Cell growth was monitored 2-3 weeks after fusion. Hybridoma supernatants were screened by standard colorimetric ELISA against BSA-conjugated peptides as described in section C. The screening process consisted of a Primary screen on 40 plates (using bleed 2 of E5571 at 1:100 dilution as a Positive control) clones (44) with O.D. greater than 0.5 were considered putatively positive and were further expanded to 24-well plate. Confirmatory screen was performed and 6 clones were confirmed positive against phospho-specific peptides (Table 4). Additional screening was performed by ELISA using the same assay as for bleed screening (FIG. 5). Western blotting was done on selected clones #7, 27 and 35 for subcloning (FIG. 6). DLD-1 cells and DLD-1 Seckel cells with and without gemcitabine treatment (100 nM for 4 h) were lysed with cell extraction buffer (Invitrogen, catalog # FNN0011). Lysates were run on NUPAGE® NOVEX® 3-8% gels (Invitrogen, catalog # EA0378BOX) and transferred to nitrocellulose membranes (Invitrogen catalog # IB3010-01) using the IBLOT® apparatus from Invitrogen. Blots were blocked with Licor ODYSSEY® blocking buffer (LiCor, catalog #927-40010) and incubated overnight with hybridoma supernatants (1:30). Blots were then washed with PBS-T (0.05% TWEEN®) and incubated with Licor goat anti-rabbit IR-680 antibody for 1 h at room temperature. Blots were then washed with phosphate-buffered saline with 0.05% TWEEN®-20 (PBS-T) and scanned at 700 nm on Licor ODYSSEY® scanner.

TABLE 4

Hybridoma Screening Data

| Hybridoma | Peptide | | | | | | AVG |
|---|---|---|---|---|---|---|---|
| | ap | bp | anp | bnp | ap/anp | bp/bnp | p/np |
| 35 | 2.38 | 2.15 | 0.08 | 0.08 | 30.9 | 25.6 | 28.3 |
| 27 | 2.27 | 2.39 | 0.10 | 0.08 | 23.9 | 28.8 | 26.4 |
| 23 | 1.11 | 1.21 | 0.08 | 0.08 | 14.8 | 15.9 | 15.4 |
| 7 | 2.26 | 2.20 | 0.24 | 0.12 | 9.3 | 18.8 | 14.1 |
| 1 | 1.03 | 0.93 | 0.09 | 0.07 | 11.4 | 13.3 | 12.4 |
| 17 | 1.99 | 1.12 | 1.80 | 0.07 | 1.1 | 16.0 | 8.6 |
| 6 | 0.85 | 0.36 | 0.07 | 0.08 | 11.5 | 4.4 | 8.0 |
| 40 | 0.13 | 1.73 | 0.08 | 1.99 | 1.7 | 0.9 | 1.3 |
| 11 | 0.63 | 0.09 | 0.45 | 0.10 | 1.4 | 1.0 | 1.2 |
| 34 | 1.54 | 1.50 | 1.29 | 1.61 | 1.2 | 0.9 | 1.1 |
| 19 | 2.25 | 2.11 | 2.11 | 2.18 | 1.1 | 1.0 | 1.0 |
| 37 | 1.77 | 1.98 | 1.88 | 1.90 | 0.9 | 1.0 | 1.0 |
| 29 | 0.82 | 0.75 | 0.82 | 0.80 | 1.0 | 0.9 | 1.0 |
| 8 | 2.10 | 1.91 | 2.22 | 1.96 | 0.9 | 1.0 | 1.0 |
| 16 | 1.63 | 1.68 | 1.72 | 1.90 | 1.0 | 0.9 | 0.9 |
| 20 | 1.93 | 1.96 | 2.29 | 2.07 | 0.8 | 0.9 | 0.9 |

Hybridoma screening data from direct ELISA against peptide antigens. Table shows analysis of raw data. Hybridomas were ranked by average ratio of signal from ATR pT1989 phospho peptide:corresponding unphosphorylated peptide (p/np). Peptide sequences shown in FIG. 2.

F. Subcloning

Subcloning was done using limited cell dilution method using standard methods. Positive subclones were selected for screening.

G. Subclone Screening

Subclones were screened by several assays. Screening was performed by enzyme-linked immunosorbant assay (ELISA) and Western blot for subclones of clones #7, 27 and 35 for subcloning. Subclones of clone #7 were then tested in an immunofluroescent (IFA) assay. Clone #7 was then tested in IFA assay. Formalin fixed paraffin embedded (FFPE) blocks were prepared from DLD-1 cells and DLD-1 Seckel cells treated with and without gemcitabine treatment (100 nM for 4 h). Slides were stained using neat hybridomas supernatants and imaged at 20×.

Subclones (7 of 7 tested) were positive for specific detection of pT1989ATR foci in cell nuclei in IFA assay demonstrating stability, specificity and clonality of the subclones.

H. Cloning of cDNA

The cDNA was cloned to generate a recombinant antibody. Briefly the cDNAs of IgG heavy and light chains were polymerase chain reaction (PCR) amplified and cloned into a mammalian expression vector. The recombinant monoclonal antibody was then transiently expressed using a HEK293 cell system. The expressed recombinant antibody was then tested and confirmed in standard ELISA against specific antigen. The cDNA was sequenced.

I. Purification of Recombinant Antibody

Recombinant antibodies were produced in serum-free medium and purified by protein-A. Briefly, protein A was pre-wash with dH2O until OD280<0.05, then re-equilibrated extensively with 1×PBS. Protein A was incubated with antibody containing supernatant and binding buffer (Pierce, Cat#21007, pH8.0) (Vol. Ratio: 1:1) with rotation, for overnight, at 4° C. The column was packed with the protein A gel, and flow-through collected. Gel was washed with 1 X PBS until OD280<0.05. Antibody was eluted with elution buffer (Pierce, Cat#21009, pH2.8) elute with 10 ml, and collect the elute in 1 ml fractions into the glass tubes containing 100 ul Neutralizing Buffer (1M Tris hydrochloride solution, pH8.0). Absorbance at 280 nm of each eluted fraction was measured. Fraction with positive OD280 were pooled and dialyzed against 1×PBS (at least 2× changes, for overnight at 4° C.). The antibody was then concentrated to desired concentration by filtration (Amicon, Millipore).

Example II

Specificity of Monoclonal Antibodies and Use in Immunoassays

A. Use and Specificity Via ELISA

The specificity of the pT1989 epitope was demonstrated by direct ELISA with corresponding phospho and non phospho peptide conjugated at N- or C terminal to BSA as described in Example I, section C (FIG. 5). Clone 7A7 bound the phosphopeptide conjugated at either C term or N-term and did not cross-react with the corresponding non-phospho peptide-BSA conjugates.

B. Use and Specificity for Western Blot

Figure 7:
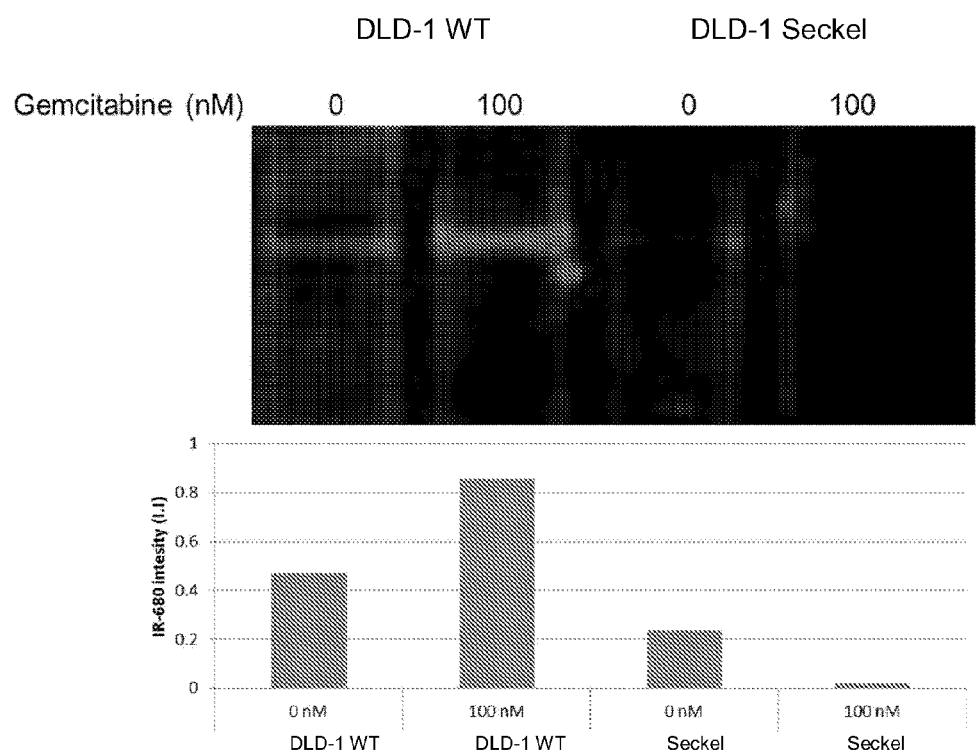
FIG. 7. Relative quantification of ATR band in Western blot of hybridoma #7.
Figure 8:
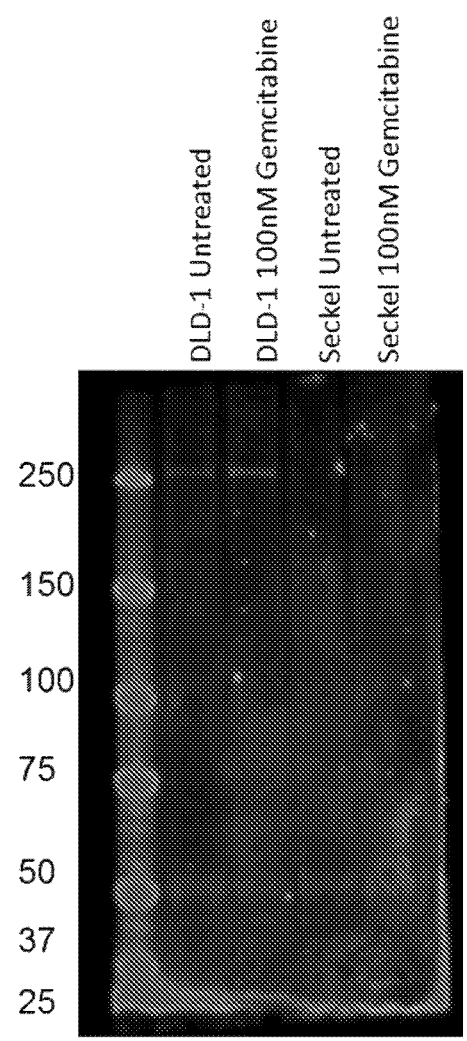
FIG. 8. Western blot of subclone 7A7. Lane 1, molecular weight marker; lane 2, DLD-1 untreated; lane 3 DLD1 treated with 100 nm gemcitabine for 4 h; lane 4 Seckel cell untreated; lane 5 Seckel cell treated with 100 nM gemcitabine for 4 h.

Additional specificity was demonstrated by Western blotting (shown in FIGS. 6-8) of lysates from cells expressing ATR (HT-29, LoVo and DLD-1). Details for lysate preparation and Western blotting are given in Example I, section E. The antibody detected a single band at about 250 kDa consistent with the predicted molecular weight (MW) for ATR. The antibody also detected an increase in phospho-ATR (pT1989) upon gemcitabine (SIGMA) treatment which is known to increase ATR activity (*Mol. Pharmacol.* (2005), 68, 1636-1644). Finally, an isogenic pair of DLD-1 cells was used. The antibody showed greatly decreased ATR level in the ATR pathway deficient Seckel cells (Oncogene (2007) 26, 2535-2542) compared to the parental DLD-1 cell lysate.

C. Use and Specificity for IFA

Figure 9:
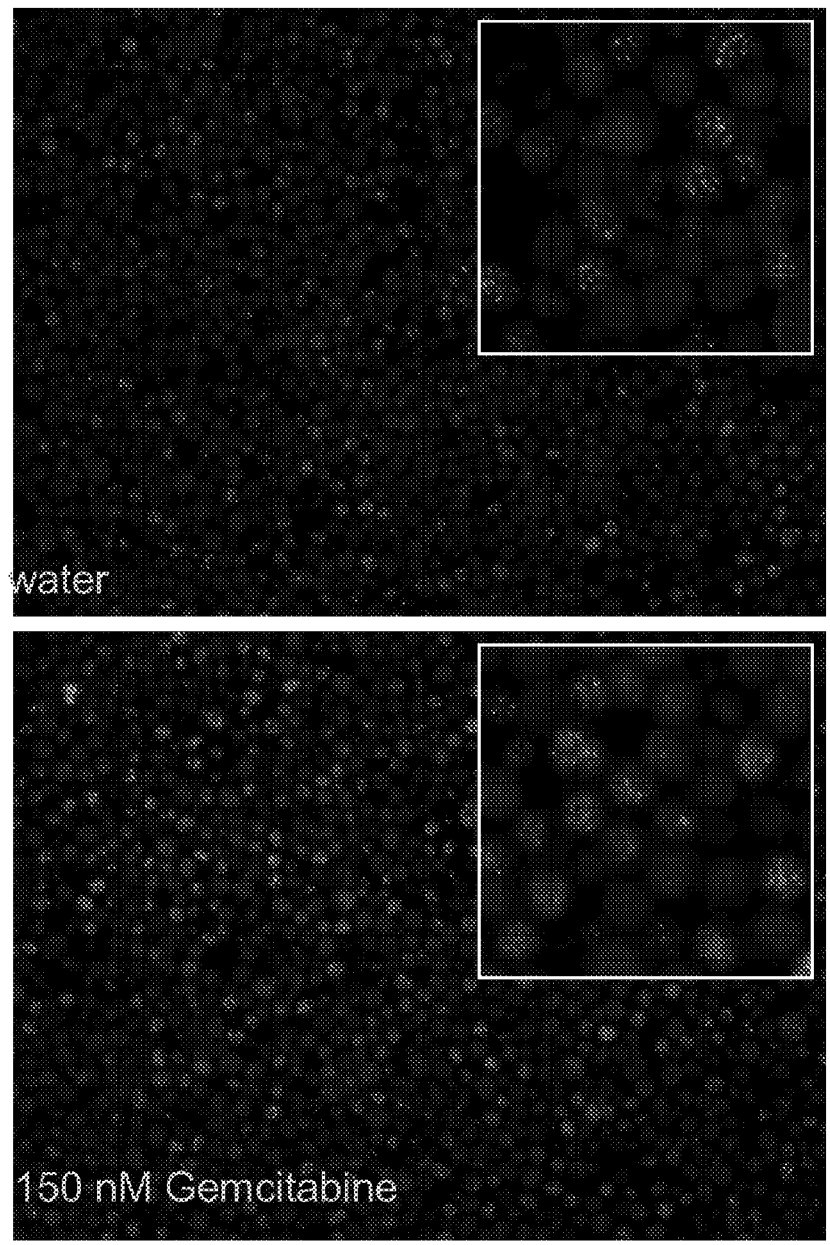
FIG. 9. ATR-pT1989 immunofluoresence (IFA) assay for formalin fixed paraffin embedded (FFPE) HT-29 cells treated with water and 150 nM gemcitabine, constant exposure, 20×. 4',6-diamidino-2-phenylindole (DAPI) signal and ATR-pT1989 signal is shown.
Figure 10:
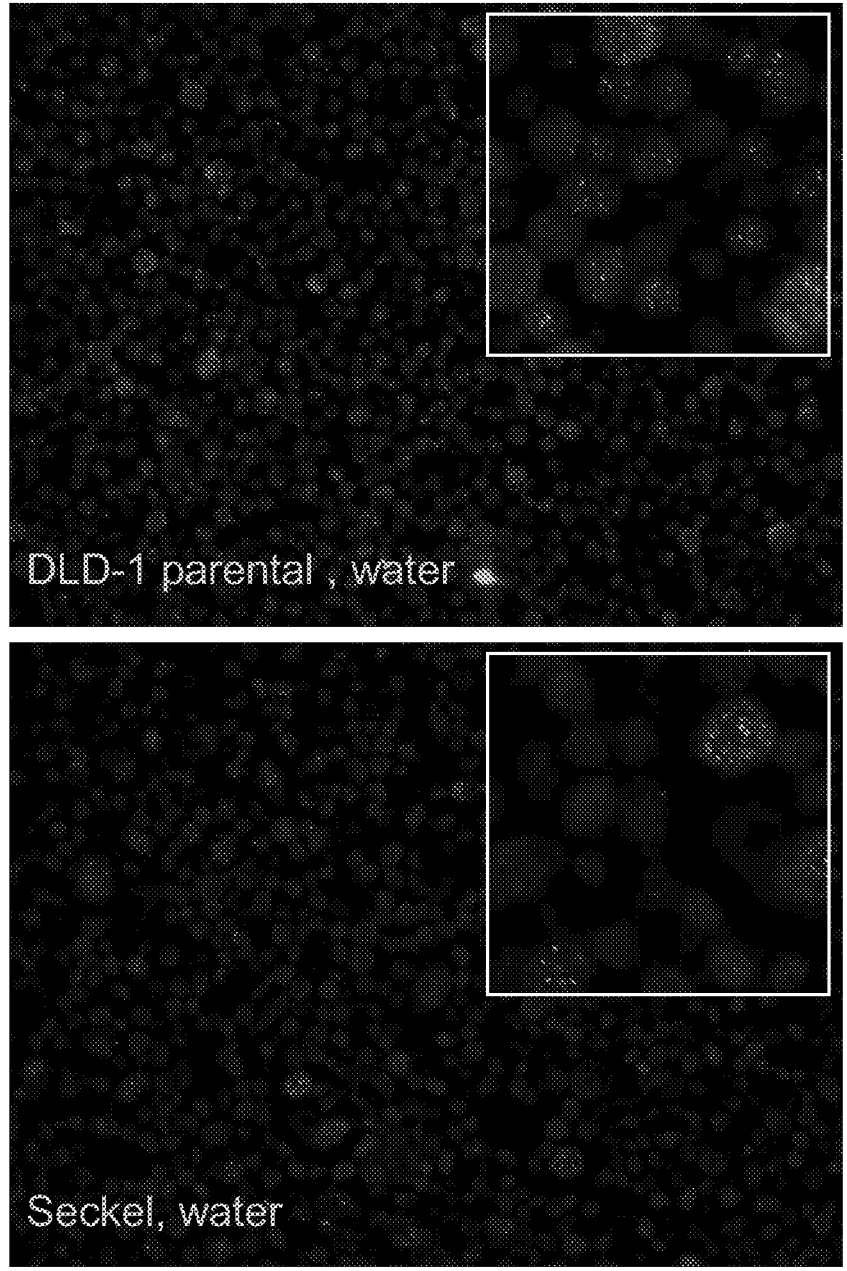
FIG. 10. ATR-pT1989 IFA assay for FFPE (10A) DLD-1 cells treated with water and (10B) DLD-1 Seckel cells treated with water, constant exposure, 20×. DAPI signal and ATR-pT1989 signal are shown.

Clone 7A7 was demonstrated to work in a slide based immunofluorescent assay (IFA, shown in FIGS. 9 and 10). Formalin fixed paraffin embedded (FFPE) pellets were generated using cells expressing WT ATR (HT29, DLD-1 Parental) or mutated ATR (DLD-1 Seckel (Horizon)), with and without gemcitabine (SIGMA) treatment to induce ATR phosphorylation at pT1989 (Mol. Pharmacol. 2005, 68, 1636-1644). Cells were harvested by trypsinization, transferred into a sterile 50 ml conical centrifuge tubes with media containing 10% serum and pelleted at 1000×g for 5 minutes. Medium was replaced with fresh serum containing medium and centrifuged again at 1000×g, 5 minutes. All but 1 ml (approximately) of medium was removed and the pellet was re-suspended by flicking the tube. Suspended cells were transferred using a 2 ml pipette into a clean 1.5 ml conical Eppendorf tube. Cells were pelleted for 30 seconds at 8,000 rpm in an Eppendorf micro centrifuge. The supernatant was discarded leaving approximately 100-200 ul behind. The cell pellet was loosened by gently flicking the tube and Thrombin stock (8 ul of 1 unit/ul water, Sigma #T-7009) was added. The cells were mixed briefly by gently flicking the tube then held on ice for 2-5 minutes. Fibrinogen stock (5 ul of at 10 mg/ml water, Sigma #F-3879) was added, and the tube was incubated for 2-5 minutes at room temperature. Clotted cells were pelleted by a brief centrifuge for 20 seconds at 10K. The supernatant was discarded and 1.0 ml of room temperature 10% neutral buffered formalin (Sigma) was added. The cells were fixed at room temperature for 8-16 hours. Following fixation, cells were centrifuged 30 seconds at 8,000 rpm in an Eppendorf micro centrifuge. The supernatant (fixative) was removed, and 1 ml of 70% ethanol in nuclease free water was added. Paraffin processing was next performed within 3 days. Slides were generated and stained with clone 7A7 and DAPI.

The gemcitabine treated cells had higher signal intensity for pT1989 staining compared to untreated cells and the Seckel cells had lower signal intensity, as compared to the parental line.

Example III

Use of Monoclonal Antibodies for PD Applications of ATR Inhibitors//Modulators

A. Use and Specificity for Western Blot

Figure 11:
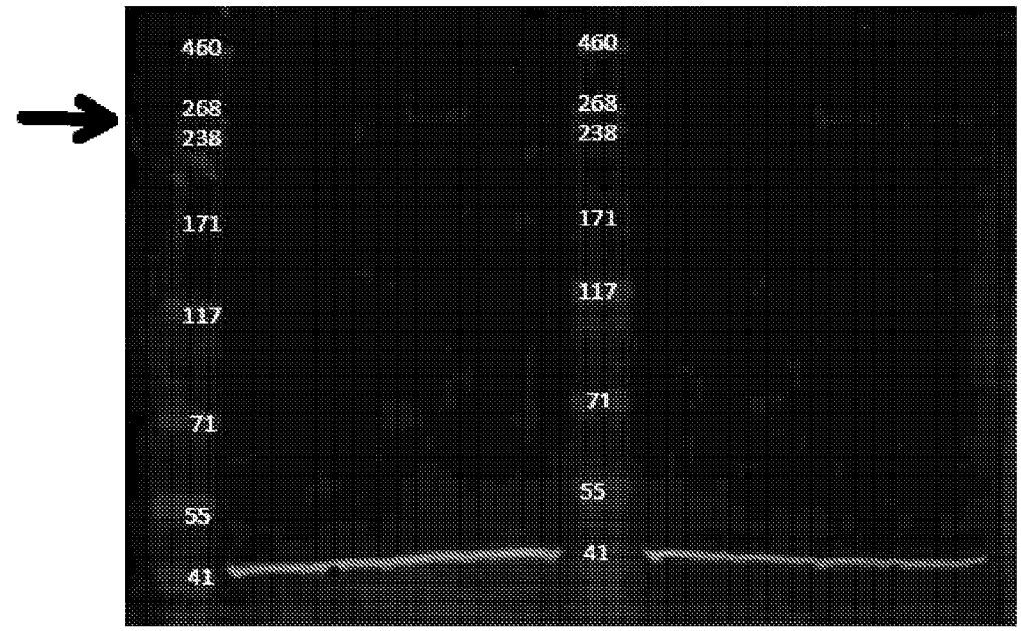
FIG. 11. Western blot of Hybridoma 7, ATR expressing colon cancer cell lines (LoVo, HT29). Lane 1, molecular weight marker; lane 2, LoVo vehicle; lane 3, LoVo VE-821, 1 uM 4 hours (hr); lane 4, LoVo gemcitabine, 150 nM 4 h; lane 5, LoVo VE-821 plus gemcitabine, lane 6, MW marker; lane 7, HT29 vehicle; lane 8, HT29 VE-821, 1 uM 4 hr; lane 9, HT29 gemcitabine, 150 nM 4 h; lane 10, HT29 VE-821 plus gemcitabine 34 ug protein per well.

Additional specificity was demonstrated by Western blotting (FIG. 11) of lysates from cells expressing ATR (HT-29 and LoVo), that were treated with an ATR inhibitor. Cells were treated for 4 hours with either vehicle (DMSO, 0.01%), 150 nM Gemcitabine (Sigma), 1 uM ATR inhibitor VE-821 or combination of drugs. The antibody detected a single band at about 250 kDa consistent with the predicted MW for ATR. The antibody also detected an increase in phospho-ATR (pT1989) upon Gemcitabine treatment, which is known to increase ATR activity (Molecular Pharmacology (2005) 68, 1636-1644). Treatment with the ATR inhibitor VE-821 alone did not affect phospho-ATR (pT1989) compared to vehicle, but combined treatment of gemcitabine and VE-821 had reduced phospho-ATR (pT1989) compared to gemcitabine alone. Lysates were prepared in buffer as follows: 0.94 ml RIPA buffer, 40 μl Protease Inhibitor Cocktail (25× stock, Roche Cat#11697498001), 10 μl Phosphatase Inhibitor (Roche Cat#04906845001) and 10 μl PMSF (Sigma cat#93482). Lysates were sonicated prior to use. Lysates were run on 3-8% Tris-Acetate gels from NOVEX® (Invitrogen, Cat# EA0378BOX) and transferred to nitrocellulose membranes using the IBLOT® transfer apparatus, program setting P3, 20V, 13 min. Blots were blocked with Licor ODYSSEY® blocking buffer and incubated overnight with Clone 7 hybridoma supernatant (1:30). B lots were then washed with PBS-T (0.05% Tween) and incubated with Licor goat anti-rabbit IR-680 antibody for 1 h at room temperature. Mouse anti-β-actin was used as a loading control, probed with Licor goat anti-mouse IR-800 antibody for 1 h at room temperature. Blots were washed with PBS-T (0.05% TWEEN®) and scanned at 700 nm and 800 nm on Licor ODYSSEY® scanner.

B. Use and Specificity for IFA

Figure 12:
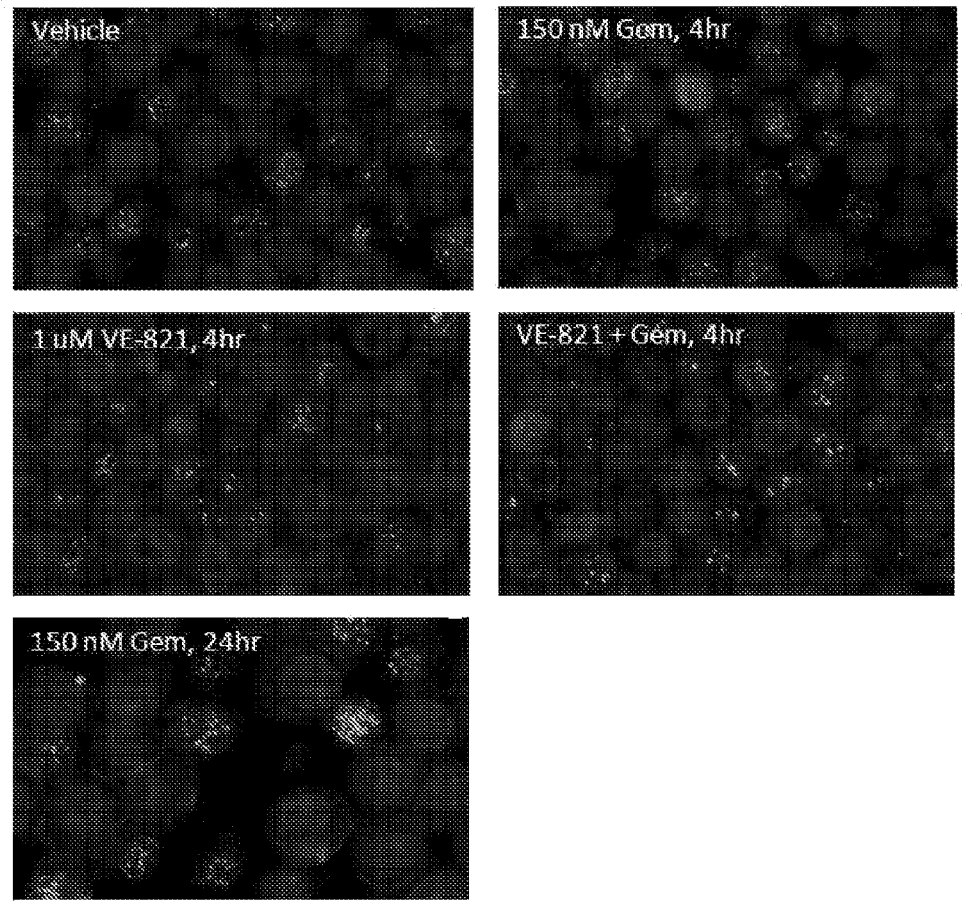
FIG. 12. ATR-pT1989 IFA assay using purified recombinant 7A7, 4 ug/ml. HT29 cells treated with vehicle (DMSO), ATR inhibitor VE-821, gemcitabine or the combination for 4 hrs, gemcitabine as a single agent for 24 hrs. Constant exposure, 40×. DAPI signal in blue, ATR-pT1989 in green. Nuclear foci were counted using DEFINIENS® software.

Clone 7A7 was demonstrated to work in a slide based IFA (FIG. 12). Formalin fixed paraffin embedded (FFPE) pellets were generated (see example II, part C).

Treatment Protocol: HT29 cells were treated for 4 hrs with either vehicle, 150 nM Gemcitabine, 1 uM ATR inhibitor VE-821 or combination of drugs to monitor induction of ATR phosphorylation at pT1989. A 24 hrs exposure to 150 nM Gemcitabine was also included. Slides were then generated and stained with clone 7A7. The gemcitabine treated cells had higher signal intensity for pT1989 staining compared to untreated cells.

Example IV

Effect of VE-281

VE-281 was chosen for molecular analysis because it targets ATR (Charrier et al., Journal Med. Chem. 2011; 54(7):2320-30; Reaper et al., Nature Chem. Biol. 2011; 7(7):428-30) upstream from Chk1. The structure of VE-281 is shown below:

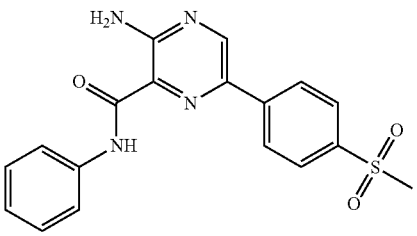 [SMILES: CS(=O)(=O)c1ccc(-c2cnc(N)c(C(=O)Nc3ccccc3)n2)cc1]

For these studies, auto-phosphorylation of ATR on threonine 1989, a DNA damage activation site (Nam et al., J Biol Chem 2011; 286(33):28707-14; Liu et al., Molecular cell 2011; 43(2):192-202), was determined, as well as Chk1 phosphorylation on serine 345, which is mediated by ATR. Histone H2AX phosphorylation was also determined on serine 139 (γH2AX), a validated pharmacodynamic biomarker for DNA damage and apoptosis (Bonner et al., Nat Rev Cancer 2008; 8(12):957-67; Kinders et al., Clin Cancer Res 2010; 16(22):5447-57; Solier et al., Mol Cell Biol 2009; 29(1):68-82).

Figure 14A:
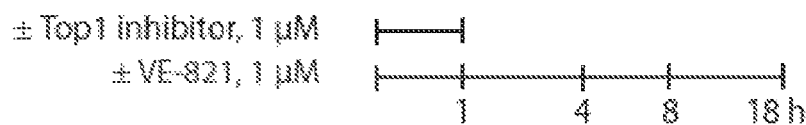
FIGS. 14A-C show that VE-821 inhibits the ATR-Chk1 response. (14A) Experimental protocol. Cells were treated with Top1 inhibitors without or with VE-821 as indicated. Samples were harvested at 0, 4, 8 and 18 h after Top1 inhibitor removal. (14B) Kinetics of ATR activation (phosphorylation on threonine 1989), Chk1 activation (phosphorylation on serine 345), Chk2 activation (phosphorylation on threonine 68) and γH2AX analyzed by immunoblotting. GAPDH was used as loading control. (14C) Same as panel B for LMP-400 instead of CPT.

The protocol is shown in FIG. 14A. Briefly, cell lysates were electrophoresed on 4-20% Tris-glycine or 3-8% Tris-acetate polyacrylamide gels, and transferred onto nitrocellulose membranes. Antibodies against GAPDH, ATR and pS345-Chk1 were obtained from Cell Signaling Technologies, γH2AX and pT68-Chk2 from Abcam and Top1 from BD Biosciences. The antibody against pT1989-ATR is disclosed above. After incubation with secondary antibody, signals were detected by enhanced chemiluminescence (Pierce).

Figure 14B:
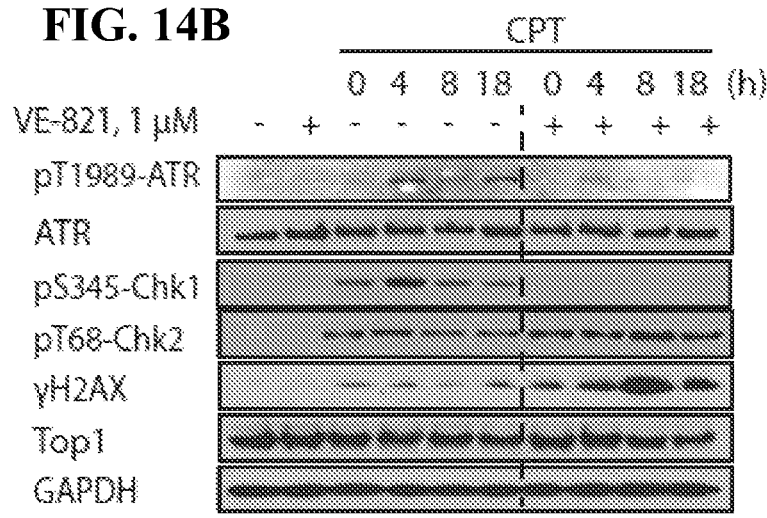
Figure 14C:
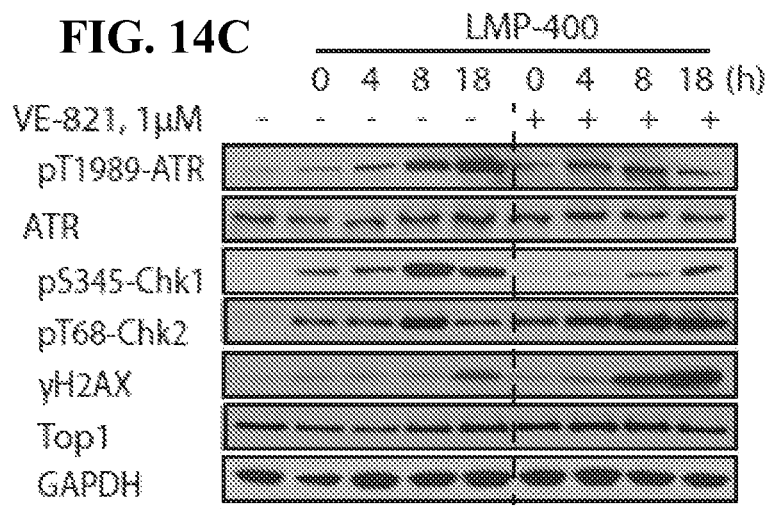

CPT and LMP-400 quickly induced the rapid phosphorylation of Chk1, Chk2 and H2AX, while phosphorylation of AIR was delayed and best detectable after drug removal. Chk1 and AIR remained phosphorylated for 18 hours after drug removal, consistent with the persistent checkpoint activation for hours after Top1 inhibitor removal (Seiler et al., Mol. Cell. Biol. 2007; 27(16):5806-18; Shao et al., EMBO J 1999; 18:1397-406). VE-821 inhibited the phosphorylation of both ATR and Chk1 without reducing Chk2 phosphorylation, confirming the specificity of VE-821 for ATR. Notably, VE-821 strongly induced γH2AX: over time (FIGS. 14B and 14C). LMP-400 showed more pronounced effects than CPT, consistent with the enhanced Top1 inhibitory potency of LMP-400 (Antony et al., Cancer Res 2007; 67(21):10397-405). See also Josse et al., "The ATR inhibitors VE-821 and VX-970 sensitize cancer cells to topoisomerase I inhibitors by disabling DNA replication initiation and fork elongation responses," Cancer Res., Pub. Online-First Sep. 30, 2014; doi: 10.115810008-5472.CAN-13-3369, which is incorporated herein by reference.

Example V

A2780 Xenografts

In vivo studies were performed. A2780 xenografts were evaluated in mice treated with 1.2 mg/kg cisplatin or 6.0 mg/kg cisplatin for 4, 7 and 24 hours. The immunofluoresecnce assay with the ATR-pT1989 antibody detected an increase in ATR foci in the treated samples compared to vehicle in both a dose and time dependent manner (FIG. 15A-15D). The following methods were used in these studies:

Xenograft Samples and In Vivo Quantitation: Athymic nu/nu mice were implanted with A2780 cells as previously described (Kinders et al., Clin Cancer Res 2010:16(22): 5447-57). Xenograft quadrants were collected and flash frozen from mice following exposure to vehicle (0.9% saline) or various doses (1.2, 6.0 mg/kg) of cisplatin administered intraperitoneally. The samples were fixed in neutral-buffered formalin and paraffin-embedded as previously described (Kinders et al., Clin Cancer Res 2010; 16(22): 5447-57). Animal care was provided in accordance with the procedures outlined in the "Guide for Care and Use of Laboratory Animals" (National Research Council; 1996; National Academy Press; Washington, D.C.), and all studies were conducted under an approved Animal Care and Use Committee protocol.

Immunofluorescence Staining: The method used for staining tissue sections was carried out using a BOND-MAX™ Autostainer Staining protocol. The AIR 1989-P antibody was run at a 10 ug/ml dilution and ALEXA FLUOR® 546 goat anti-rabbit (Invitrogen) was used as the reporter. After completion of the staining, PROLONG® Gold Antifade Reagent (Invitrogen) was dropped onto the slides and coverslips; slides were cured overnight in the dark and imaged the following day. Image capture of the tissue sections was carried out using a Nikon 90i Microscope with an A1 confocal head with a 20× objective.

Quantitative Marker Analysis: The DEFINIENS TISSUE STUDIO® (Version 2.0.3; Build 2057) software program was used for analysis of foci count/nucleus. For the analysis, fields were scored first for the number of nuclei and then individual counts of the number of foci count/per nucleus were performed. An average of 10 representative fields was taken per xenograft quadrant, with, a total of 5 mice per treatment group.

Example VI

Detection of ATR Foci in Human Clinical Samples

Figure 16:
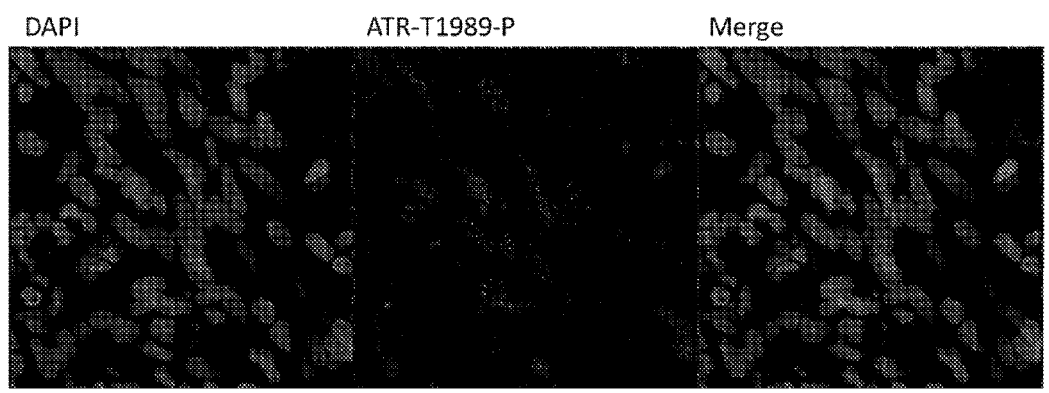
FIG. 16 shows detection of ATR foci in a human clinical sample. A human tumor biopsy sample from NCI Cancer Therapy Evaluation Program (CTEP) trial 9350 was prepared into an FFPE block and slides were sectioned to 5 um. A Backup-1 slide was used to stain with DAPI as a nuclear marker (left) and pATR T1989 (center). A merge of the two channels is shown on the right. pATR is visualized as discreet foci specifically localized to the nuclear region of the cells.

ATR foci were also detected in human clinical samples (FIG. 16). Human clinical biopsy samples (Cancer Therapy Evaluation Program (CTEP) trial 9350) were prepared as FFPE blocks following the Tumor Frozen Needle Biopsy Preparation for Immunofluorescence Assay (IFA) on Tumor Biopsies protocol (LHTP003.07.01). The biopsy samples were stained using the BOND-MAX™ autostainer and a modified staining protocol, as outlined above in Example V. All patients gave written informed consent for study inclusion and were enrolled on institutional review board-approved protocols.

Example VII

Comparison of 7A7 and Commercially Available Antibodies

Figures 17A, 17B, 17C:
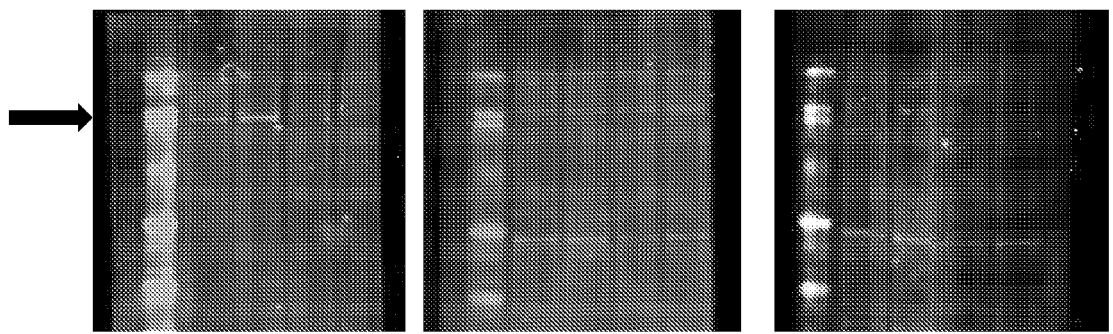
FIGS. 17A-17C are digital images of a Western Blots of colon cell lysates probed with anti-ATR-pT1989 antibodies. (17A) Rabbit Hybridoma clone 7-7 (7A7)1:50, (17B) Kerafast pT1989 1:25 and (17C) Kerafast pT1989 1:100. GAR-IR-680 was used at 0.1 ug/ml. In each blot, Lane 1: MW markers, lane 2: DLD1 parental untreated, lane 3: DLD1 parental 100 nM Gemcitabine 4 hour, lane 4: DLD-1 seckel untreated, lane: DLD-1 seckel 100 nM Gemcitabine 4 hours. Clone 7A7 was specific to pATR, and detected pATR specifically at a dilution of 1:50. However, the commercially available antibody (Kerafast) provided weak detection of pATR in gemcitabine treated DLD-1 cells at a dilution of 1:25, but not at a dilution of 1:100. Thus, the commercially available antibody had poor specificity and sensitivity, and would be unsuitable for immunoassay applications such as pharmacodynamic immunofluorescence assay. The detection of cross-reactive proteins also indicated that the commercially available (Kerafast) antibody cannot be used for quantitation in unpurified samples.

Clone 7A7 was compared with other clones and commercial antibodies including the Kerafast monoclonal antibody on identical replicate Western blots of crude cell lysates. Clone 7 detected pT1989 ATR specific bands while the Kerafast monoclonal antibody did not detect pT1989 ATR (see FIGS. 17A-17C). The result shows that 7A7 is specific for pT1989 ATR, and that it is far more effective than a commercially available antibody.

For these studies, DLD-1 parental and DLD-1 Seckel (Horizon) cells were treated with gemcitabine for 4 hours. Clone 7A7 detected ATR in the parental DLD-1 cell lysate by Western blotting and detects an increase in pT1989-ATR with gemcitabine treatment as expected. In contrast, the level of pT-1989 detected by clone 7A7 was much lower in the DLD-1 Seckel cells which have suppressed ATR expression.

The commercially available (Kerafast) pT1989 antibody was very weak and non-specific (highly cross-reactive), since multiple bands were seen in a Western blot. The commercially available (Kerafast) antibody was determined to be unsuitable for many immunoassay applications such as pharmacodynamic immunofluorescence assays (IFAs) or other techniques wherein ATR is not present in a purified form. In contrast, Clone 7A7 was successfully used in pharmacodynamic IFA assay applications.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. An isolated monoclonal antibody, or antigen binding fragment thereof, comprising a heavy chain variable region and a light chain variable region,
   wherein the heavy chain variable region comprises a heavy chain complementarity determining region (H-CDR)1, a H-CDR2, and a H-CDR3 of the heavy chain variable region set forth as SEQ ID NO: 6, and
   wherein the light chain variable region comprises a light chain complementarity determining region (L-CDR)1, a L-CDR2, and a L-CDR3 of the light chain variable region set forth as SEQ ID NO: 7,
   wherein the heavy chain complementarity determining regions and the light chain complementarity determining regions are determined using the methods of Kabat, Chothia or IMGT, and
   wherein the monoclonal antibody or antigen binding fragment specifically binds to an epitope comprising a phosphorylated threonine at amino acid position 1989 of SEQ ID NO: 1.

2. The isolated monoclonal antibody or antigen binding fragment of claim 1, wherein
   (a) the H-CDR1, H-CDR2, and H-CDR3, comprise amino acids 48-52, 67-82, and 113-121 of SEQ ID NO: 6, respectively, and the L-CDR1, L-CDR2, and L-CDR3 comprise amino acids 45-57, 73-79 and 112-124 of SEQ ID NO: 7, respectively; or
   (b) the H-CDR1, H-CDR2, and H-CDR3, comprise amino acids 43-49, 69-73, and 113-121 of SEQ ID NO: 6, respectively, and the L-CDR1, L-CDR2, and L-CDR3 comprise amino acids 45-57, 73-79 and 112-124 of SEQ ID NO: 7, respectively.

3. The isolated monoclonal antibody or antigen binding fragment of claim 1, wherein the heavy chain variable region comprises the amino acid sequence set forth as SEQ ID NO: 6.

4. The isolated monoclonal antibody or antigen binding fragment of claim 1, wherein the light chain variable region comprising the amino acid sequence set forth as SEQ ID NO: 7.

5. The isolated monoclonal antibody or antigen binding fragment of claim 1, wherein the heavy and light chain variable regions comprise the amino acid sequences set forth as SEQ ID NO: 6 and SEQ ID NO: 7, respectively.

6. The isolated monoclonal antibody of claim 1, wherein the antibody is an IgG.

7. The antigen binding fragment of claim 1.

8. The antigen binding fragment of claim 7, wherein the antigen binding fragment is a Fv, Fab, F(ab')$_2$, scFV or a scFV$_2$ fragment.

9. The isolated monoclonal antibody or antigen binding fragment of claim 1, conjugated to a detectable label.

10. The isolated monoclonal antibody or antigen binding fragment of claim 9, wherein the detectable marker is a fluorescent, enzymatic, heavy metal or radioactive marker.

11. An isolated nucleic acid molecule encoding the monoclonal antibody or antigen binding fragment of claim 1.

12. The isolated nucleic acid molecule of claim 11, operably linked to a promoter.

13. An expression vector comprising the nucleic acid molecule of claim 11.

14. A host cell, comprising the expression vector of claim 13.

15. A composition, comprising an effective amount of the isolated monoclonal antibody or antigen binding fragment of claim 1, a nucleic acid molecule encoding the monoclonal antibody or antigen binding fragment, or an expression vector comprising the nucleic acid molecule, and a pharmaceutically acceptable carrier.

16. A kit for detecting the presence of ataxia telangiectasia-mutated and RAD3-related kinase phosphorylated at position 1989 in a cell, comprising
   a container comprising the isolated monoclonal antibody or antigen binding fragment of claim 1, a nucleic acid molecule encoding the monoclonal antibody or antigen binding fragment, or an expression vector comprising the nucleic acid molecule, and
   instructions for using the kit.

17. A method of detecting the presence of ataxia telangiectasia-mutated and RAD3-related kinase phosphorylated at position 1989, comprising:
   contacting a sample comprising a cell or an extract thereof with an effective amount of the monoclonal antibody or antigen binding fragment of claim 1 that specifically binds ataxia telangiectasia-mutated and RAD3-related kinase phosphorylated at position 1989, under conditions sufficient to form an immune complex; and
   detecting the presence of the immune complex, wherein the presence of the immune complex indicates the presence of ataxia telangiectasia-mutated and RAD3-related kinase phosphorylated at position 1989 in the sample.

18. The method of claim 17, wherein the cell is cultured in vitro.

19. The method of claim 17, wherein the sample is a biological sample obtained from a subject of interest.

20. The method of claim 19, wherein the subject of interest has cancer and wherein the cell is a cancer cell.

21. The method of claim 19, wherein the presence of the immune complex indicates that the subject can be treated with an ataxia telangiectasia-mutated and RAD3-related kinase inhibitor.

22. The method of claim 17, further comprising comparing the amount of the immune complex to a control.

23. The method of claim 17, further comprising
   contacting the sample with a second antibody, wherein the second antibody specifically binds the monoclonal antibody or antigen binding fragment that specifically binds ataxia telangiectasia-mutated and RAD3-related kinase phosphorylated at position 1989.

24. The method of claim 23, wherein the second antibody is labeled.

25. A method of determining the effectiveness of a dose of a therapeutic agent for treatment of a subject, comprising
   contacting a test sample from the subject comprising a cell or an extract thereof with an effective amount of the monoclonal antibody or antigen binding fragment of claim 1, under conditions sufficient to form an immune complex, wherein the test sample is obtained following administration of the therapeutic agent to the subject; and measuring the binding of the monoclonal antibody or antigen binding fragment to an epitope comprising a phosphorylated threonine at amino acid position 1989 of SEQ ID NO: 1 present in the test sample, wherein a decrease in the amount of binding of the monoclonal antibody or antigen binding fragment thereof to the epitope in the test sample as compared to a control indicates that the dose is effective for treating the subject, wherein the control is the binding of the monoclonal antibody or antigen binding fragment to an epitope comprising a phosphorylated threonine at amino acid position 1989 of SEQ ID NO: 1 present in a control sample obtained from the subject prior to administration of the therapeutic agent to the subject.

26. The method of claim 25, further comprising
administering to the subject an additional dose of the therapeutic agent, contacting an additional sample from the subject comprising a cell or an extract thereof with an effective amount of the monoclonal antibody or antigen binding fragment of claim 1, under conditions sufficient to form an immune complex; and measuring the binding of the monoclonal antibody or antigen binding fragment to an epitope comprising a phosphorylated threonine at amino acid position 1989 of SEQ ID NO: 1 present in the additional sample, wherein a decrease or no change in the amount of binding of the monoclonal antibody or antigen binding fragment thereof to the epitope as compared to binding of the monoclonal antibody or antigen binding to the epitope present in the test sample indicates that the additional dose is effective for treating the subject.

27. The method of claim 25, wherein the subject has cancer, and wherein the cell is a cancer cell.

28. The method of claim 26, wherein the test sample and the additional sample comprise circulating tumor cells or a bodily fluid.

29. The method of claim 25, wherein the therapeutic agent comprises an ataxia telangiectasia-mutated and RAD3-related kinase modulator.

30. The method of claim 29, wherein the therapeutic agent further comprises an additional chemotherapeutic agent.

31. The method of claim 30, wherein the additional chemotherapeutic agent is a cytotoxic agent such as but not limited to an antimetabolite, a platinating agent, an alkylating agent, or DNA cross-linkers or a targeted agent such as a poly (ADP-ribose) polymerase (PARP) inhibitor or a checkpoint kinase inhibitor, ionizing radiation or a DNA damaging agent.

32. A method for determining if an agent inhibits ataxia telangiectasia-mutated and RAD3-related kinase activity, comprising contacting a test sample comprising a cell contacted with the agent, or an extract of the cell, with an effective amount of the monoclonal antibody or antigen binding fragment of claim 1 under conditions sufficient to form an immune complex;

detecting the presence of the immune complex in the test sample;

contacting a control sample comprising a cell not contacted with the test agent, or an extract of the cell, with an effective amount of the monoclonal antibody or antigen binding fragment of claim 1 under conditions sufficient to form an immune complex;

detecting the presence of the immune complex in the control sample; and comparing the amount of the immune complex in the test sample to the amount of the immune complex in the control sample;

wherein a difference in the amount of the immune complex in the test sample as compared to the control sample indicates that the agent affects ataxia telangiectasia-mutated and RAD3-related kinase activity.

33. The method of claim 32, wherein the cell is a cell from a cell line.

34. The method of claim 32, wherein the cell is a cancer cell.

35. The method of claim 34, wherein the cancer cell is in a tissue section.

36. A method to determine if a tumor can be treated using an ataxia telangiectasia-mutated and RAD3-related kinase (ATR) inhibitor, comprising contacting a sample comprising cells from the tumor with an effective amount of the monoclonal antibody or antigen binding fragment of claim 1 that specifically binds ataxia telangiectasia-mutated and RAD3-related kinase phosphorylated at position 1989, under conditions sufficient to form an immune complex; and detecting the presence of the immune complex, wherein the presence of the immune complex indicates that the tumor can be treated with the ATR inhibitor.

37. The method of claim 36, wherein the absence of the immune complex indicates that the tumor cannot be treated with the ATR inhibitor.

38. The method of claim 17, wherein the cell is in a biopsy, surgical specimen or fine needle aspirate.

39. The method of claim 17, wherein the cell is a breast cancer cell or a bone marrow cell.

40. The method of claim 17, wherein the cell is a peripheral blood mononuclear cell or a hair follicle cell.

* * * * *